US007186506B1

(12) United States Patent
Parkin et al.

(10) Patent No.: US 7,186,506 B1
(45) Date of Patent: Mar. 6, 2007

(54) MEANS AND METHODS FOR MONITORING PROTEASE INHIBITOR ANTIRETROVIRAL THERAPY AND GUIDING THERAPEUTIC DECISIONS IN THE TREATMENT OF HIV/AIDS

(75) Inventors: Neil T. Parkin, Belmont, CA (US); Rainer A. Ziermann, San Mateo, CA (US)

(73) Assignee: Monogram Biosciences, Inc., South San Franisco, CA (US)

( * ) Notice: Subject to any disclaimer, the term of this patent is extended or adjusted under 35 U.S.C. 154(b) by 0 days.

(21) Appl. No.: 09/663,458

(22) Filed: Sep. 15, 2000

Related U.S. Application Data

(63) Continuation-in-part of application No. PCT/US00/17178, filed on Jun. 22, 2000, and a continuation-in-part of application No. 09/591,899, filed on Jun. 12, 2000, now Pat. No. 6,869,759.

(51) Int. Cl.
*C12Q 1/68* (2006.01)
(52) U.S. Cl. .................. 435/6; 435/369; 435/320.1; 435/235.1
(58) Field of Classification Search .............. 435/5, 435/6, 369, 320.1, 235.1
See application file for complete search history.

(56) References Cited

U.S. PATENT DOCUMENTS

| 5,436,131 | A | | 7/1995 | Condra et al. |
| 5,766,842 | A | | 6/1998 | Melnick et al. |
| 5,837,464 | A | * | 11/1998 | Capon et al. ............... 435/6 |
| 6,033,902 | A | | 3/2000 | Haseltine et al. |
| 6,103,462 | A | | 8/2000 | Paulous et al. |
| 6,242,187 | B1 | | 6/2001 | Capon et al. |
| 2003/0108857 | A1 | | 6/2003 | Parkin et al. |
| 2004/0106106 | A1 | | 6/2004 | Parkin et al. |

FOREIGN PATENT DOCUMENTS

| WO | WO99/67427 | 6/1999 |
| WO | PCT/US00/17178 | 12/2000 |
| WO | WO00/78996 | 12/2000 |
| WO | PCT/US01/28754 | 3/2002 |
| WO | WO02/22076 | 3/2002 |
| WO | WO02/068618 | 9/2002 |
| WO | WO02/099387 | 12/2002 |
| WO | PCT/US02/18684 | 1/2003 |
| WO | WO03/070700 | 8/2003 |
| WO | WO04/003512 | 1/2004 |
| WO | WO04/003514 | 1/2004 |
| WO | PCT/US03/21335 | 5/2004 |
| WO | PCT/US03/21355 | 5/2004 |
| WO | PCT/US03/21023 | 7/2004 |
| WO | PCT/US03/04362 | 12/2004 |

OTHER PUBLICATIONS

Patick et al. Antimicrobial Agents and Chemotherapy. 1998; 42 (10): 2637-2644.*
Hazuda et al. Science. Jan. 2000; 287: 646-650.*
Craig et al. AIDS. 1998; 12: 1611-1618.*
Young, B. et al., Resistance Mutations in Protease and Reverse Transcriptase Genes of Human Immunodeficiency Virus Type 1 Isolates From Patients With Combination Antiretroviral Therapy Failure, *Journal of Infectious Diseases*, vol. 178, No. 5, pp. 1497-1501 (Nov. 1998).
Hertogs et al., A Rapid Method for Simultaneous Detection of Phenotypic Resistance to Inhibitors of Protease and Reverse Transcriptase in Recombinant Human Immunodeficiency Drugs. *Antimicrobial Agents and Chemotherapy*, vol. 42, No. 2, pp. 269-276 (Feb. 1998).
Ziermann et al., "A Mutation in Human Immunodeficiency Virus Type 1 Protease, N88S, That Causes in Vitro Hypersensitivity to Amprenavir," (2000), Journal of Virology, 74:4414-4419.
Dreyer GB, et al."A Symmetric Inhibitor Binds HIV-1 Protease Asymmetrically" *Biochemistry* (1993) 32:937-947.
J. Eron, et al., Preliminary Assessment of 141 W94 in Combination with Other Protease Inhibitors, *5th Conference on Retroviruses and Opportunistic Infections*: (1995) 6.
Hill, A. et al. (1998) "Low frequency of genotypic mutations associated with resistance to AZT and 3TC after combination treatment with indinavar," Int. Conf. *AIDS* 12:812, (Abstract No. 6).
E. E. Kim, (1995) "Crystal Structure of HIV-1 Protease in Complex with VX-478, a Potent and Orally Bioavailable Inhibitor of the Enzyme," J. AM. Chem. Soc., 117: 1181-1182.
Lambert DM, et al. (1992) "Human Immunodeficiency Virus Type 1 Protease Inhibitors Irreversibly Block Infectivity of Purified Virions From Chronically Infected Cells" *Anit Microb Agents Chem* 36:982-98.
Brendan A. Larder, et al., (1995) "Potential Mechanism for; Sustained Antiretroviral Efficacy of AZT-3TC Combination Therapy,"*Science*, 269; 696-699.
Janis K. Lazdins, et al., (1997) "In Vitro Effect of al-Acid Glycoprotein on the Anti-Human Immunodeficiency Virus (HIV) Activity of the Inhibitor CGP 61775: A Comparative Study wits Other Relevant HIV Protease Inhibitors," *J Infec. Dis.*, 175: 1063-1070.
David J. Livingston, et al., (1995) "Weak Binding of VX-478 tc Human Plasma Proteins and Implications for Anti-Humar Immunodeficiency Virus Therapy," *J Infec. Dis.*, 172:1. 238-124.
Bhuvaneshwari Mahalingam, et al., (1999) "Structural and Kinetic Analysis of Drug Resistant Mutants of HIV Protease," *Biochem.*, 263: 1-9.

(Continued)

*Primary Examiner*—Jeffrey Stucker
*Assistant Examiner*—Bo Peng
(74) *Attorney, Agent, or Firm*—Jones Day

(57) ABSTRACT

This invention relates to antiviral drug susceptibility and resistance tests to be used in identifying effective drug regimens for the treatment of human immunodeficiency virus (HIV) infection and acquired immunodeficiency syndrome (AIDS), particularly treatment regimens including a protease inhibitor. The invention further relates to the means and methods of monitoring the clinical progression of HIV infection and its response to antiretroviral therapy using phenotypic or genotypic susceptibility assays.

8 Claims, 28 Drawing Sheets

OTHER PUBLICATIONS

Miller M, et al. (1989) Structure of Complex of Synthetic HIV-1j Protease with a SubstrateBased Inhibitor at 2.3 A Resolution, *Science* 246: 1149-1152.

Mohri H, et al. (1993) "Quantitation of Zidovudine-Resistant Human Immunodeficiency Virus Type 1 in the Blood of Treated and Untreated Patients," *PNAS* 90:25-29.

Robert L. Murphy, et al., (1999) "Treatment with Amprenavir Alone or Amprenavir with Zidovudine and Lamivudine in Adults with Human Immunodeficiency Virus Infection" *J. Infec. Dis.*, 179: 808-81 E.

Najera I, et al. (1994) "Natural Occurrence of Drug ResistancE Mutations in the Reverse Transcriptase of Human Immunodeficiency Virus Type 1 Isolates," *Aids Res Hum Retroviruses* 10:1479-1488.

Najera l, et al. (1995) "pol Gene Quasispecies of Humar Immunodeficiency Virus: Mutations Associated with Drug ResistancE in Virus From Patients Undergoing No Drug Therapy," *J Virol* 69:23-31.

Sarah Palmer, et al., (1999) "Highly Drug-resistant HIV-1 Clinical Isolates Are Cross-resistant to Many Antiretroviral Compunds in Current Clinical Development," *AIDS*, 13:661-667.

Neil T. Parkin, et al., (1999) "Phenotypic changes in Drug Susceptibility Associated with Failure of Human Immunodeficiency Virus Type 1 (HIV-1) Triple Combination Therapy," *J Infec. Dis.*, 180: 865-870.

Judith A. Partaledis, et al., (1995) "In Vitro Selection and Characterization of Human Immunodeficiency Virus Type 1 (HIV-1) Isolates with Reduced Sensitivity to Hydroxyethylamino Sulfonamide Inhibitors of HIV-1 Aspartyl Protease," *Journal of Virology*. 69: 5228-5235.

Petit SC, et al. (1993) "The Specificity of the HIV-1 Protease" *Drug Discov Des* 1:69-83.

Roberts NA, et al. (1990) "Rational Design of Peptide-Based HIV Proteinase" *Science* 248:358361.

Roberts, N. A., (1995) "Drug-resistance patterns of saquinavir and other HIV proteinase inhibitors," *AIDS.9* (supp 2) S27-S32.

Brian M. Sadler, et al., (1999) "Safety and Pharmacokinetics of Amprenavir (141W94), a Human Immunodeficiency Virus (HIV) Type 1 Protease Inhibitor, Following oral Administration of Single Doses to HIV-Infected Adults," *Antimicrobial Agents and Chemtherapy*, 43: 1686-1692.

Sarkar G. and Sommer SS., (1990) "The"Megaprimer"Method of Site-Directed Mutagenesis," *Bio Tech* 8(4):404-407.

Mary L. Smidt, et al., (1996) "A Mutation in Human Immunodeficiency Virus Type 1 Protease at Position 88, Located Outside the Active Site, Confers Resistance to the Hydroxyethylurea Inhibitor SC-55389A," *Antimicrobial Agents and Chemotherapy*, 41: 515-522.

M. H. St. Clair, et al., (1996) "In Vitro Antiviral Activity of 141 W94 (VX-478) in Combination with Other Antiretroviral Agents," *Antiviral Research* 29: 53-56.

H. Tian, et al., (1998) "Zidovudine/Lamivudine Co-resistance Is Preceded by a Transient Period of Zidovudine Hypersensitivity, " 2nd International Workshop on HIV Drug Resistance and Treatment Strategies, Abstract 30.

Tisdale, M. et al. (1998): "Genotypic and phenotypic analysis of HIV from patients on ZDV/3TC/amprenavir combination therapy, " *Int. Conf AIDS* 12:583 (Abstract No. 32312).

Simon P. Tucker, et al., (1998) "Estimate of the Frequency of Human Immunodeficiency Virus Type 1 Protease Inhibitor Resistance Within Unselected Virus Populations In Vitro," *Antimicrobial Agents and Chemotherapy*, 42: 478-480.

Craig et al., 1998 "HIV Protease Genotype and Viral Sensitivity to HIV Protease Inhibitors Following Saquinavir Therapy", *AIDS*, 12: 1611-1618.

Carrillo et al., (1998), "In Vitro Selection and Characterization of Human Immunodefciency Virus Type 1 Variants With Increased Resistance to ABT-378, a Novel Protease Inhibitor," *Journal of Virology*, 72(9): 7532-41.

Condra et al., (1996), "Genetic Correlates of In Vivo Resistance to Indinavir, a Human Immunodeficiency Virus Type 1 Protease Inhibitor," *Journal of Virology*, 70(12): 8270-76.

Genbank Accession No. P12497 POL Polyprotein (2004).

Genbank Accession No. AF324493 HIV-1 vector pNL4. . . [gi:12831134] (2001).

Gervaix, et al., (1997), "A New Reporter Cell Line to Monitor HIV Infection and Drug Susceptibility in Vitro," *Proc. Natl. Acad. Sci. USA*, 94: 4653-4658.

Gong et al., (2000), In Vitro Resistance Profile of the Human Immonodeficiency Virus Type 1 Protease Inhibitor BMS-232632, *Antimicrobial Agents and Chemotherapy*, 44(9): 2319-26.

Gunthard, et al., (1998), "Comparative Performance of High-Density Oligonucleotide Sequencing and Dideoxynucleotide Sequencing of HIV Type 1 polFrom Clinical Sample," *Aids Research and Human Retroviruses*. 14(10): 869-876.

Haubrich et al., (2001), "CCTG 575: A Randomized. Prospective Study of Phenotype Testing Versus Standard of Care for Patients Failing Antiretroviral Therapy," *Antiviral Therapy*, 6(Supplement 1): 63.

Herrmann, et al., (1997), "A Working Hypotheses-Virus Resistance Development As An Indicator of Specific Antiviral Activity," *Ann. NY Acad Sciences*, 284: 632-637.

Hirsch, et al., (2000), "Antiretroviral Drug Resistance Testing in Adult HIV-1 Infection" *JAMA*, 283(18): 2417-26.

Katzenstein et al., (2002), "Baseline Phenotypic Susceptibility and Virologic failure over 144 weeks Among Nucleoside RT Inhibitor Experienced Subjects in ACTG 364," Antiretroviral Drug Resistance Testing in Adult HIV-1 Infection,*2002 9th Conference on Retroviruses and Opportunistic Infections*, Session 77 Poster Session 591-T.

Katzenstein et al., (2002), "The Inhibitory Quotient (IQ) for Saquinavir (SQV) Predicts Virologic Reponse to Salvage Therapy," *2002 9th Conference on Retroviruses and Opportunistic Infections*, Session 28 Poster Session 129.

Kempf et al., (2001), "Identification of Genotypic Changes in Human Immunodeficiency Virus Protease that Correlate With Reduced Susceptibility to the Protease Inhibitor Lopinavir Among Viral Isolates From Protease Inhibitor-Experienced Patients," *Journal of Virology*, 75(16): 7462-69.

Maguire et al., (2002), "Emergence of Resistance to Protease Inhibitor Amprenavir in Human Immondeficiency Virus Type 1-Infected Patients: Selection of Four Alternative Viral Protease Genotypes and Influence of Viral Susceptibilty to Coadministered Reverse Transcriptase Nucleoside Inhibitors," *Antimicrobial Agents and Chemotherapy*, 46(3): 731-738.

Petropoulos, et al., (2000), "A Novel Phenotypic Drug Susceptibilty Assay for Human Immunodeficiency Virus Type 1," *Antimicrobial Agents and Chemotherapy*,44(4): 920-928.

Race, et al., (1999), "Analysis of HIV Cross-Resistance to Protease Inhibitors Using a Rapid Single-Cycle Recombinant Virus Assay for Patients Failing on Combination Therapies," *AIDS*, 13(15): 2061-2068.

Rusconi, Stefano. et al. (2000): "Susceptibility to PNU-140690(Tipranavir) of Human Immunodeficiency Virus Type 1 Isolates Derived From Patients with Multidrug Resistance to Other Protease Inhibitors," *Antimicrobial Agents and Chemotherapy*, 44(5): 1328-32.

Schuurman, et al., (1999), "Worldwide Evaluation of DNA Sequencing Approaches for Identification of Drug Resistance Mutations in the Human Immunodeficiency Virus Type 1 Reverse Transcriptase," *Journal of Clinical Microbiology*, 37(7): 2291-2296.

Shi, et al., (1997), "A Recombinant Retroviral System for Rapid In Vivo Analysis of Human Immunodeficiency Virus Type 1 Susceptibilty to reverse Transcriptase Inhibitors," *Antimicrobial Agents and Chemotherapy*, 41(12): 2781-85.

Tisdale, M. et al. (1995): "Cross-Resistance Analysis of Human Immunodeficiency Virus Type 1 Variants Individually Selected for Resistance to Five Different Protease Inhibitors," *Antimicrobial Agents and Chemotherapy* 39(8):1704-10.

* cited by examiner

*Fitness Assay*

*Luciferase Activity in Infected Cells*

*Replication Fitness, PR Processing, and RT Activity*

*Site Directed RT Mutants (G190 Series)*

*Site Directed PR Mutants*

Phenotypic Drug Susceptibility, Replication Fitness and PR/RT Function

*Relation of PI Resistance to Replication Capacity*

*Relation of NRTI and NNRTI Resistance to Replication Capacity*

Low Replication Capacity
is Associated with High
Numbers of Mutations
in Protease and L90M

*Low Replication Capacity is Associated With Specific Protease Mutations*

*Relation of NFV Phenotypic Drug Susceptibility, Gag Processing and Replication Fitness*

Mutations in PR Associated with Gag Processing Defects

|  | NRTI | | | | NNRTI | | | PI | | | | |
|---|---|---|---|---|---|---|---|---|---|---|---|---|
| WEEK | AZT | 3TC | D4T | ABC | NVP | DLV | EFV | SQV | IDV | RTV | NFV | AMP |
| day 0 | 3.7 | >100 | 2.8 | 19 | >300 | 88 | 115 | 85 | 72 | 73 | 74 | 16 |
| 1 | 4.5 | >100 | 3.3 | 20 | >300 | 78 | 134 | 95 | 74 | 59 | 80 | 21 |
| 2 | 5.8 | >100 | 3.2 | 14 | >300 | 75 | 142 | 89 | 77 | 49 | 59 | 19 |
| 3 | 6.5 | >100 | 2.7 | 15 | >300 | 96 | 183 | 59 | 75 | 52 | 51 | 15 |
| 4 | 6.3 | >100 | 3.1 | 15 | >300 | 94 | 174 | 59 | 68 | 50 | 49 | 15 |
| 5 | 6.4 | >100 | 3.0 | 17 | >300 | 76 | 119 | 59 | 60 | 54 | 36 | 10 |
| 6 | 5.0 | >100 | 2.8 | 19 | >300 | 93 | 168 | 89 | 39 | 80 | 40 | 18 |
| 7 | 9.1 | >100 | 4.1 | 12 | >300 | 89 | 154 | 85 | 78 | 53 | 53 | 19 |
| 9 | 2.8 | 8.1 | 1.9 | 5.0 | 22 | 15 | 10 | 1.8 | 3.5 | 4.7 | 4.0 | 2.0 |
| 10 | 1.5 | 1.7 | 1.1 | 1.3 | 1.7 | 2.0 | 1.6 | 0.9 | 1.6 | 1.9 | 1.8 | 1.6 |
| 11 | 0.9 | 1.2 | 1.0 | 1.2 | 0.8 | 1.1 | 0.9 | 1.0 | 1.1 | 1.1 | 1.1 | 1.0 |
| 12 | 0.8 | 1.3 | 0.8 | 1.2 | 0.5 | 1.0 | 0.8 | 0.8 | 0.8 | 0.9 | 1.1 | 0.8 |
| 23 | 0.7 | 1.1 | 1.0 | 0.6 | 0.8 | 1.1 | 0.8 | 0.8 | 0.8 | 1.0 | 0.9 | 0.6 |

FIG. 18
*Patient Virus Reversion to Drug Susceptibility After Treatment Interruption*

Patient Virus Reversion
to Normal Replication Fitness
After Treatment Interruption To Measure Replication Capacity of
Patient-Derived Recombinant Viruses

*To Measure Replication Capacity of Patient-Derived Recombinant Viruses*

MEANS AND METHODS FOR MONITORING PROTEASE INHIBITOR ANTIRETROVIRAL THERAPY AND GUIDING THERAPEUTIC DECISIONS IN THE TREATMENT OF HIV/AIDS

This application is a continuation in part of U.S. application Ser. No. 09/591,899, filed Jun. 12, 2000, now U.S. Pat. No. 6,869,759, and is also a continuation in part of PCT International Application No. PCT/US00/17178, filed Jun. 22, 2000, the contents of each of which are hereby incorporated by reference into this application.

Throughout this application, various references are referred to within parenthesis. Disclosures of these publications in their entireties are hereby incorporated by reference into this application to more fully describe the state of the art to which this invention pertains.

TECHNICAL FIELD

This invention relates to antiretroviral drug susceptibility and resistance tests to be used in identifying effective drug regimens for the treatment of human immunodeficiency virus (HIV) infection and acquired immunodeficiency syndrome (AIDS). The invention further relates to the means and methods of monitoring the clinical progression of HIV infection and its response to antiretroviral therapy using phenotypic or genotypic susceptibility assays. The invention also relates to novel vectors, host cells and compositions for carrying out phenotypic susceptibility tests. The invention further relates to the use of various genotypic methodologies to identify patients who do not respond to a particular antiretroviral drug regimen. This invention also relates to the screening of candidate antiretroviral drugs for their capacity to inhibit viral replication, selected viral sequences and/or viral proteins. More particularly, this invention relates to the determination of protease inhibitor (PRI) susceptibility using phenotypic or genotypic susceptibility tests. This invention also relates to a means and method for accurately and reproducibly measuring viral replication fitness.

BACKGROUND OF THE INVENTION

HIV infection is characterized by high rates of viral turnover throughout the disease process, eventually leading to CD4 depletion and disease progression. Wei X, Ghosh S K, Taylor M E, et al. (1995) Nature 343, 117–122 and Ho D D, Naumann A U, Perelson A S, et al. (1995) Nature 373, 123–126. The aim of antiretroviral therapy is to achieve substantial and prolonged suppression of viral replication. Achieving sustained viral control is likely to involve the use of sequential therapies, generally each therapy comprising combinations of three or more antiretroviral drugs. Choice of initial and subsequent therapy should, therefore, be made on a rational basis, with knowledge of resistance and cross-resistance patterns being vital to guiding those decisions. The primary rationale of combination therapy relates to synergistic or additive activity to achieve greater inhibition of viral replication. The tolerability of drug regimens will remain critical, however, as therapy will need to be maintained over many years.

In an untreated patient, some $10^{10}$ new viral particles are produced per day. Coupled with the failure of HIV reverse transcriptase (RT) to correct transcription errors by exonucleolytic proofreading, this high level of viral turnover results in $10^4$ to $10^5$ mutations per day at each position in the HIV genome. The result is the rapid establishment of extensive genotypic variation. While some template positions or base pair substitutions may be more error prone (Mansky L M, Temin H M (1995) J Virol 69, 5087–5094) (Schinazi R F, Lloyd R M, Ramanathan C S, et al. (1994) Antimicrob Agents Chemother 38, 268–274), mathematical modeling suggests that, at every possible single point, mutation may occur up to 10,000 times per day in infected individuals.

For antiretroviral drug resistance to occur, the target enzyme must be modified while preserving its function in the presence of the inhibitor. Point mutations leading to an amino acid substitution may result in changes in shape, size or charge of the active site, substrate binding site or in positions surrounding the active site of the enzyme. Mutants resistant to antiretroviral agents have been detected at low levels before the initiation of therapy. (Mohri H, Singh M K, Ching W T W, et al. (1993) Proc Natl Acad Sci USA 90, 25–29) (Nájera I, Richman D D, Olivares I, et al. (1994) AIDS Res Hum Retroviruses 10, 1479–1488) (Nájera I, Holguin A, Quiñones-Mateu E, et al. (1995) J Virol 69, 23–31). However, these mutant strains represent only a small proportion of the total viral load and may have a replication or competitive disadvantage compared with wild-type virus. (Coffin J M (1995) Science 267, 483–489). The selective pressure of antiretroviral therapy provides these drug-resistant mutants with a competitive advantage and thus they come to represent the dominant quasi species (Frost S D W, McLean A R (1994) AIDS 8, 323–332) (Kellam P, Boucher C A B, Tijnagal J M G H (1994) J Gen Virol 75, 341–351) ultimately leading to a rebound in viral load in the patient.

Early development of antiretroviral therapy focused on inhibitors of reverse transcriptase. Both nucleoside and non-nucleoside inhibitors of this enzyme showed significant antiviral activity (DeClerq, E. (1992) AIDS Res. Hum. Retrovir. 8:119–134). However, the clinical benefit of these drugs had been limited due to drug resistance, limited potency, and host cellular factors (Richman, D. D. (1993) Ann. Rev. Pharm. Tox. 32:149–164). Thus inhibitors targeted against a second essential enzyme of HIV were urgently needed.

In 1988, the protease enzyme of HIV was crystallized and its three-dimensional structure was determined, (Navia M A, Fitzgerald P M D, McKeever B M, Leu C T, Heimbach J C, Herber W K, Sigal I S, Darke P L, Springer J P (1989) Nature 337:615–620 and Winters M A, Schapiro J M, Lawrence J, Merigan T C (1997) In Abstracts of the International Workshop on HIV Drug Resistance, Treatment Strategies and Eradication, St. Petersburg, Fla.) allowing for the rapid development of protease inhibitors. Initially, it was hypothesized that HIV protease, unlike reverse transcriptase, would be unable to accommodate mutations leading to drug resistance. This is not the case, and to date over 20 amino acid substitutions in the HIV protease have been observed during treatment with the currently available protease inhibitors. The genetic pattern of mutations conferring resistance to these protease inhibitors is complex, and cross-resistance between structurally different compounds occurs.

Protease Inhibitors

HIV protease was classified as an aspartic proteinase on the basis of putative active-site homology (Toh H, Ono M, Saigo K, Miyata T (1985) Nature 315:691), its inhibition by peptastin (Richards A D, Roberts R, Dunn B M, Graves M C, Kay J (1989) FEBS Lett 247:113), and its crystal structure (Navia M A, Fitzgerald P M D, McKeever B M, Lau C T, Heimbach J C, Herber W K, Sigal I S, Darke P L, Springer J P (1989) Nature 337:615–620). The enzyme functions as a homodimer composed of two identical 99-amino acid chains (Debouck C, Navia M A, Fitzgerald P M D, McKeever B M, Leu C T, Heimbach J C, Herber W K, Sigal I S, Darke P L, Springer J P (1988) Proc. Natl. Acad. Sci. USA 84:8903–8906), with each chain containing the characteristic Asp-Thr-Gly active-site sequence at positions 25 to 27 (Toh H, Ono M, Saigo K, Miyata T (1985) Nature 315:691).

HIV protease processes gag (p55) and gag-pol (p160) polyprotein products into functional core proteins and viral enzymes (Kohl N E, Diehl R E, Rands E, Davis L J, Hanobik M G, Wolanski B, Dixon R A (1991) J. Virol. 65:3007–3014 and Kramer R A, Schaber M D, Skalka A M, Ganguly K, Wong-Staal F, Reddy E P (1986) Science 231:1580–1584). During or immediately after budding, the polyproteins are cleaved by the enzyme at nine different cleavage sites to yield the structural proteins (p17, p24, p7, and p6) as well as the viral enzymes reverse transcriptase, integrase, and protease (Pettit S C, Michael S F, Swanstrom R (1993) Drug Discov. Des. 1:69–83).

An asparagine replacement for aspartic acid at active-site residue 25 results in the production of noninfectious viral particles with immature, defective cores (Huff J R (1991) AIDS J. Med. Chem. 34:2305–2314, Kaplan A H, Zack J A, Knigge M, Paul D A, Kempf D J, Norbeck D W, Swanstrom R (1993) J. Virol. 67:4050–4055, Kohl N E, Emini E A, Schleif W A, Davis L J, Heimbach J C, Dixon R A, Scolnik E M, Sigal I S (1988) Proc. Natl. Acad. Sci. USA 85:4686–4690, Peng C, Ho B K, Chang T W, Chang N T (1989) J. Virol. 63:2550–2556). Similarly, wild-type virus particles produced by infected cells treated with protease inhibitors contain unprocessed precursors and are noninfectious (Crawford S, Goff S P (1985) J. Virol. 53:899–907, Gottlinger H G, Sodroski J G, Haseltine W A (1989) Proc. Natl. Acad. Sci. USA 86:5781–5785, Katoh I Y, Yoshinaka Y, Rein A, Shibuya M, Odaka T, Oroszlan S (1985) Virology 145:280–292, Kohl N E, Emini E A, Schleif W A, Davis L J, Heimbach J C, Dixon R A, Scolnik E M, Sigal I S (1988) Proc. Natl. Acad. Sci. USA 85:4686–4690, Peng C, Ho B K, Chang T W, Chang N T (1989) J. Virol. 63:2550–2556, Stewart L, Schatz G, Wogt V M (1990) J. Virol. 64:5076–5092). Unlike reverse transcriptase inhibitors, protease inhibitors block the production of infectious virus from chronically infected cells (Lambert D M, Petteway, Jr. S R, McDanal C E, Hart T K, Leary J J, Dreyer G B, Meek T D, Bugelski P J, Bolognesi D P, Metcalf B W, Matthews T J (1992) Antimicrob. Agents Chemother. 36:982–988). Although the viral protease is a symmetric dimer, it binds its natural substrates or inhibitors asymmetrically (Dreyer, G B, Boehm J C, Chenera B, DesJarlais R L, Hassell A M, Meek T D, Tomaszek T A J, Lewis M (1993) Biochemistry 32:937–947, Miller M J, Schneider J, Sathyanarayana B K, Toth M V, Marshall G R, Clawson L, Selk L, Kent S B, Wlodawer A (1989) Science 246:1149–1152). These findings together with the knowledge that amide bonds of proline residues are not susceptible to cleavage by mammalian endopeptidases gave rise to the first class of HIV-1 protease inhibitors based on the transition state mimetic concept, with the phenylalanine-proline cleavage site being the critical nonscissile bond (Roberts N A, Martin J A, Kinchington D, Broadhurst A V, Craig J C, Duncan I B, Galpin S A, Handa B K, Kay J, Krohn A, Lambert R W, Merett J H, Mills J S, Parkes K E B, Redshaw S, Ritchie A J, Taylor D L, Thomas G J, Machin P J (1990) Science 248:358–361).

Amino Acids Implicated in Resistance to Protease Inhibitors.

As new protease inhibitors are developed, the ability of certain amino acid substitutions to confer resistance to the inhibitor is usually determined by several methods, including selection of resistant strains in vitro, site-directed mutagenesis, and determination of amino acid changes that are selected during early phase clinical trials in infected patients. While some amino acid substitutions are specifically correlated with resistance to certain protease inhibitors (see below), there is considerable overlap between sets of mutations implicated in resistance to all approved protease inhibitors. Many investigators have attempted to classify these mutations as either being "primary" or "secondary", with varying definitions. For example, some investigators classify as primary mutations which are predicted, based on X-ray crystallographic data, to be in the enzyme active site with the potential for direct contact with the inhibitor. (e.g. D3ON, G48V, I50V, V82A/F/S/T, I84V, N88S, L90M). Secondary mutations are usually considered as being compensatory for defects in enzyme activity imposed by primary mutations, or as having enhancing effects on the magnitude of resistance imparted by the primary mutations (e.g. L10I/F/R/V, K20I/M/R/T, L24I, V32I, L33F/V, M36I/L/V, M46I/L/V, I47V, I54L/V, L63X, A71T/V, G73A/S/T, V77I, N88D). Lists of mutations and corresponding inhibitors are maintained by several organizations, for example: Schinazi et al., Mutations in retroviral genes associated with drug resistance, *Intl. Antiviral News* 1999,7:46–69 and Shafer et al., Human Immunodeficiency Virus Reverse Transcriptase and Protease Sequence Database, Nucleic Acids Research 1999, 27(1), 348–352.

Saquinavir

Saquinavir, developed by Hoffmann-La Roche, was the first protease inhibitor to undergo clinical evaluation, demonstrating that HIV-1 protease was a valid target for the treatment of HIV infection (Jacobsen H, Brun-Vezinet F, Duncan I, Hanggi M, Ott M, Vella S, Weber J, Mous J (1994) J. Virol. 68:2016–2020). Saquinavir is a highly active peptidomimetic protease inhibitor with a 90% inhibitory concentration (IC90) of 6 nM (id). In vitro, saquinavir can select for variants with one or both of two amino acid substitutions in the HIV-1 protease gene, a valine-for-glycine substitution at position 48 (G48V), a methionine-for-leucine substitution at residue 90 (L90M), and the double substitution G48V-L90M (Eberle J, Bechowsky B, Rose D, Hauser U, vonder Helm K, Guertler L, Nitschko H (1995) AIDS Res. Hum. Retroviruses 11:671–676, Jacobsen H, Yasargil K, Winslow D L, Craig J C, Kroehn A, Duncan I B, Mous J (1995) Virology 206:527–534, Turriziani O, Antonelli G, Jacobsen H, Mous J, Riva E, Pistello M, Dianzani F (1994) Acta Virol. 38:297–298). In most cases, G48V is the first mutation to appear, and continued selection results in highly resistant double-mutant variants. A substitution at either residue results in a 3- to 10-fold decreased susceptibility to the inhibitor, whereas the simultaneous occurrence of both substitutions causes a more severe loss of susceptibility of >100-fold (id).

In vivo, saquinavir therapy appears to select almost exclusively for mutations at codons 90 and 48 (id, Jacobsen H, Hangi M, Ott M, Duncan I B, Owen S, Andreoni M, Vella S, Mous J (1996) J. Infect. Dis. 173:1379–1387, Vella S, Galluzzo C, Giannini G, Pirillo M F, Duncan I, Jacobsen H, Andreoni M, Sarmati L, Ercoli L (1996) Antiviral Res. 29:91–93). Saquinavir-resistant variants emerge in approximately 45% of patients after 1 year of monotherapy with 1,800 mg daily (Craig I C, Duncan I B, Roberts N A, Whittaker L (1993) In Abstracts of the 9th International Conference on AIDS, Berlin, Germany, Duncan I B, Jacobsen H, Owen S, Roberts N A (1996) In Abstracts of the 3rd Conference of Retroviruses and Opportunistic Infections, Washington, D. D., id, Mous J, Brun-Vezinet F, Duncan I B, Haenggi M, Jacobsen H, Vella S (1994) In Abstracts of the 10th International Conference on AIDS, Yokohama, Japan). The frequency of resistance is lower (22%) in patients receiving combination therapy with zidovudine, zalcitabine, and saquinavir (Collier A C, Coombs R, Schoenfeld D A, Bassett R L, Joseph Timpone M S, Baruch A, Jones M, Facey K, Whitacre C, McAuliffe V J, Friedman H M, Merigan T C, Reichmann R C, Hooper C, Corey L (1996) N. Engl. J. Med. 334:1011–1017). In contrast to in vitro-selected virus, where the G48V mutation is the first step to resistance, the L90M exchange is the predominant mutation selected in vivo while the G48V (2%) or the double mutant (<2%) is rarely found (id). In another recent study of in vivo resistance during saquinavir monotherapy no patient was found to harbor a G48V mutant virus (Ives K J, Jacobsen H, Galpin S A, Garaev M M, Dorrell L, Mous J, Bragman K, Weber J N (1997 J. Antimicrob. Chemother. 39:771–779). Interestingly, Winters et al. (id) observed a higher frequency of the G48V mutation in patients receiving higher saquinavir doses as monotherapy. All patients (six of six) who initially developed G48V also acquired a V82A mutation either during saquinavir treatment or after switching to either indinavir or nelfinavir. An identical mutational pattern was found in another study during saquinavir monotherapy (Eastman P S, Duncan I B, Gee C, Race E (1997) In Abstracts of the International Workshop on HIV Drug Resistance, Treatment Strategies and Eradication, St. Petersburg, Fla.). Some residues represent sites of natural polymorphism of the HIV-1 protease (positions 10, 36, 63, and 71) and appear to be correlated to the L90M mutation (id). Another substitution, G73S, has been recently identified and may play a role in saquinavir resistance in vivo. Isolates from five patients with early saquinavir resistance and those from two patients with induced saquinavir resistance after a switch of therapy to indinavir carried the G73S and the L90M substitutions Dulioust A, Paulous S, Guillemot L, Boue F, Galanaud P, Clavel F (1997) In Abstracts of the International Workshop on HIV Drug Resistance, Treatment Strategies and Eradication, St. Petersburg, Fla.).

Ritonavir

Ritonavir, developed by Abbott Laboratories, was the second HIV protease inhibitor to be licensed in the United States. Ritonavir is a potent and selective inhibitor of HIV protease that is derived from a C2-symmetric, peptidomimetic inhibitor (Ho D D, Toyoshima T, Mo H, Kempf D J, Norbeck D, Chen C M, Wideburg N E, Burt S K, Erickson J W, Singh M K (1994) J. Virol. 68:2016–2020). In vitro activity has been demonstrated against a variety of laboratory strains and clinical isolates of HIV-1 with IC90s of 70 to 200 nM (Kuroda M J, El-Farrash M A, Cloudhury S, Harada S (1995) Virology 210:212–216.

Resistant virus generated by serial, in vitro passages is associated with specific mutations at positions 84, 82, 71, 63, and 46 (Markowitz M, Mo H, Kempf D J, Norbeck D W, Bhat T N, Erickson J W, Ho D D (1995) J. Virol. 69:701–706). The I84V substitution appeared to be the major determinant of resistance, resulting in a 10-fold reduction in sensitivity to ritonavir. Addition of the V82F mutation confers an even greater level of resistance, up to 20-fold. The substitutions M46I, L63P, and A71V, when introduced into the protease coding region of wild-type NL4-3, did not result in significant changes in drug susceptibility. Based on replication kinetics experiments, these changes are likely to be compensatory for active-site mutations, restoring the impaired replicative capacity of the combined V82F and I84V mutations.

Indinavir

Indinavir, developed by Merck & Co., is the third HIV protease inhibitor licensed in the United States. Indinavir is a potent and selective inhibitor of HIV-1 and HIV-2 proteases with Ki values of 0.34 and 3.3 nM, respectively (Vacca J p, Dorsey B D, Schleif W A, Levin R B, McDaniel S L, Darke P L, Zugay J, Quintero J C, Blahy O M, Roth E, Sardana V V, Schlabach A J, Graham P I, Condra J H, Gotlib L, Holloway M K, Lin J, Chen L-w, Vastag K, Ostobich D, Anderson PS, Emini E A, Huff J R (1994) Proc. Natl. Acad. Sci. USA 91:4096–4100). The drug acts as peptidomimetic transition state analogue and belongs to the class of protease inhibitors known as HAPA (hydroxyaminopentane amide) compounds (ibid). Indinavir provides enhanced aqueous solubility and oral bioavailability and in cell culture exhibits an IC95 of 50 to 100 nM (Emini E A, Schleif W A, Deutsch P, Condra J H (1996) Antiviral Chemother. 4:327–331.

Despite early reports of a lack of in vitro resistance by selection with indinavir (id), Tisdale et al. (Tisdale M, Myers R E, Maschera B, Parry N R, Oliver N M, Blair E D (1995) Antibicrob. Agents Chemother. 39:1704–1710) were able to obtain resistant variants during selection in MT-4 cells with substitutions at residues 32, 46, 71, and 82. At least four mutations were required to produce a significant loss of susceptibility (6.1-fold compared with the wild type). The mutation at position 71, described as compensatory (Markowitz M, Mo H, Kempf D J, Norbeck D W, Bhat T N, Erickson J W, Ho D D (1995) J. Virol. (id), appeared to contribute phenotypic resistance and also to improve virus growth. Emini et al. (id) and Condra et al. (Condra J H, Holder D J, Schleif W A, Blahy O M, Danovich R M, Gabryelski L J, Graham D J, Laird D, Quintero J C, Rhodes A, Robbins H L, Roth E, Shivaprakash M, Yang T, Chodakewitz J A, Deutsch P J, Leavitt R Y, Massari F e, Mellors J W, Squires K E, Steigbigel R T, Teppler H, Emini E A (1995) Nature 374:569–571) found by constructing mutant HIV-1 clones that at least three mutations at residues 46, 63, and 82 were required for the phenotypic manifestation of resistance with a fourfold loss of susceptibility.

Nelfinavir

Nelfinavir, developed by Agouron Pharmaceuticals, is a selective, nonpeptidic HIV-1 protease inhibitor that was designed by protein structure-based techniques using iterative protein crystallographic analysis (Appelt K R, Bacquet J, Bartlett C, Booth C L J, Freer S T, Fuhry M M, Gehring M R, Herrmann S M, Howland E F, Janson C A, Jones T R, Kan C C, Kathardekar V, Lewis K K, Marzoni G P, Mathews D A, Mohr C, Moomaw E W, Morse C A, Oatley S J, Ogden R C, Reddy M R, Reich S H, Schoettlin W S, Smith W W, Varney M D, Villafranca J E, Ward R W, Webber S, Webber S E, Welsh K M, White J (1991) J. Med. Chem. 34:1925–1928). In vitro, nelfinavir was found to be a potent inhibitor of HIV-1 protease with a Ki of 2.0 nM (Kaldor S W, Kalish V J, Davies J F, Shetty B V, Fritz J E, Appelt K, Burgess J A, Campanale K M, Chirgadze N Y, Clawson D K, Dressman B A, Hatch S D, Khalil D A, Kosa M B, Lubbehusen P P, Muesing M A, Patrick A K, Reich S H, Su K S, Tatlock J H (1997) J. Med. Chem. 40:3979–3985). The drug demonstrated antiviral activity against several laboratory and clinical HIV-1 and HIV-2 strains with 50% effective concentrations ranging from 9 to 60 nM (Patick A K, Boritzki T J, Bloom L A (1997) Antimicrob. Agents Chemother. 41:2159–2164). Nelfinavir exhibits additive-to-synergistic effects when combined with other antiretroviral drugs (Partaledis J A, Yamaguchi A K, Tisdale M, Blair E E, Falcione C, Maschera B, Myers R E, Pazhanisamy S, Futer O, Bullinan A B, Stuver C M, Byrn R A, Livingston D J (1995) J. Virol. 69:5228–5235). Preclinical data showed high levels of the drug in mesenteric lymph nodes and the spleen and good oral bioavailability (Shetty B V, Kosa M B, Khalil D A, Webber S (1996) Antimicrob. Agents Chemother. 40:110–114).

In vitro, following 22 serial passages of HIV-$1_{NL4-3}$ in the presence of nelfinavir, a variant (P22) with a sevenfold reduced susceptibility was isolated. After an additional six passages a variant (P28) with a 30-fold-decreased susceptibility to nelfinavir was identified (Patick A K, Ho H, Markowitz M, Appelt K, Wu B, Musick L, Kaldor S, Reich S, Ho D, Webber S (1996) Antimicrob. Agents Chemother. 40:292–297). Sequence analysis of the protease gene from these variants identified in decreasing frequency the substitutions D30N, A71V, and I84V for the P22 variant and mutations M46I, I84V/A, L63P, and A71V for the P28 variant. Antiviral susceptibility testing of recombinant mutant HIV-$1_{NL4-3}$ containing various mutations resulted in a fivefold-increased 90% effective concentration for the I84V and D30N single mutants and the M46I/I84V double mutant, whereas no change in susceptibility was observed with M46I, L63P, or A71V alone (ibid).

Amprenavir

Amprenavir is a novel protease inhibitor developed by Vertex Laboratories and designed from knowledge of the HIV-1 protease crystal structure (Kim E E, Baker C T, Dyer M D, Murcko M A, Rao B G, Tung R D, Navia M A (1995) J. Am. Chem. Soc. 117:1181–1182). The drug belongs to the class of sulfonamide protease inhibitors and has been shown to be a potent inhibitor of HIV-1 and HIV-2, with IC50s of 80 and 340 nM, respectively. The mean IC50 for amprenavir against clinical viral isolates was 12 nM (St. Clair M H, Millard J, Rooney J, Tisdale M, Parry N, Sadler B M, Blum M R, Painter G (1996) Antiviral Res. 29:53–56) HIV-1 variants 100-fold resistant to amprenavir have been selected by in vitro passage experiments (id). DNA sequence analysis of the protease of these variants revealed a sequential accumulation of point mutations resulting in amino acid substitutions L10F, M46I, I47V, and I50V. The key resistance mutation in the HIV-1 protease substrate binding site is I50V. As a single mutation it confers a two- to threefold decrease in susceptibility (ibid). The other substitutions did not result in reduced susceptibility when introduced as single mutations into an HIV-1 infectious clone (HXB2). However, a triple protease mutant clone containing the mutations M46I, I47V, and I50V was 20-fold less susceptible to amprenavir than wild-type virus. The I50V mutation has not been frequently reported in resistance studies with other HIV protease inhibitors. Kinetic characterization of these substitutions demonstrated an 80-fold reduction in the inhibition constant ($K_i$) for the I50V single-mutant protease and a 270-fold-reduced $K_i$ for the triple mutant M46I/I47V/I50V, compared to the wild-type enzyme (Pazhanisamy S, St6uvr C M, Cullinan A B, Margolin N, Rao B G (1996) J. Biol. Chem. 271:17979–17985). The single mutants L10F, M46I, and I47V did not display reduced affinity for amprenavir. The catalytic efficiency ($k_{cat}/K_m$) of the I50V mutant was decreased up to 25-fold, while the triple mutant M46I/I47V/I50V had a 2-fold-higher processing efficiency than the I50V single mutant, confirming the compensatory role of the M46I-and-I47V mutation. The reduced catalytic efficiency ($k_{cat}/K_m$) for these mutants in processing peptides appeared to be due to both increased $K_m$ and decreased $k_{cat}$ values.

Viral Fitness

The relative ability of a given virus or virus mutant to replicate is termed viral fitness. Fitness is dependent on both viral and host factors, including the genetic composition of the virus, the host immune response, and selective pressures such as the presence of anti-viral compounds. Many drug-resistant variants of HIV-1 are less fit than the wild-type, i.e. they grow more slowly in the absence of drug selection. However, since the replication of the wild-type virus is inhibited in the presence of drug, the resistant mutant can outgrow it. The reduction in fitness may be a result of several factors including: decreased ability of the mutated enzyme (i.e. PR or RT) to recognize its natural substrates, decreased stability of the mutant protein, or decreased kinetics of enzymatic catalysis. See Back et al., EMBO J. 15: 4040–4049, 1996; Goudsmit et al., J. Virol. 70: 5662–5664, 2996; Maschera et al., J. Biol. Chem. 271: 33231–33235, 1996; Croteau et al., J. Virol. 71: 1089–1096, 1997; Zennou et al., J. Virol. 72: 300–3306, 1998; Harrigan et al., J. Virol. 72: 3773–3778, 1998; Kosalaraksa et al., J. Virol. 73: 5356–5363, 1999; Gerondelis et al., J. Virol. 73: 5803–5813, 1999. Drug resistant viruses that are less fit than wild type may be less virulent i.e. they may cause damage to the host immune system more slowly than a wild type virus. Immunological decline may be delayed after the emergence of drug resistant mutants, compared to the rate of immunological decline in an untreated patient. The defect causing reductions in fitness may be partially or completely compensated for by the selection of viruses with additional amino acid substitutions in the same protein that bears the drug resistance mutations (for example, see Martinez-Picado et al., J. Virol. 73:3744–3752, 1999), or in other proteins which interact with the mutated enzyme. Thus, amino acids surrounding the protease cleavage site in the gag protein may be altered so that the site is better recognized by a drug-resistant protease enzyme (Doyon et al., J. Virol. 70: 3763–3769, 1996; Zhang et al., J. Virol. 71: 6662–6670, 1997; Mammano et al., J, Virol. 72: 7632–7637, 1998).

Integrase

Integration of viral DNA into the host chromosome is a necessary process in the HIV replication cycle (Brown, P. O., 1997, in Retroviruses; Coffin, J. M., Hughes, S. H. & Varmus, H. E., eds., Cold Spring Harbor Lab. Press, Plainview, N.Y., 161–203). The key steps of DNA integration are carried out by the viral integrase protein, which, along with protease and reverse transcriptase, is one of three enzymes encoded by HIV. Combination antiviral therapy with protease and reverse transcriptase inhibitors has demonstrated the potential therapeutic efficacy of antiviral therapy for treatment for AIDS (Vandamme, A. M., Van Vaerenbergh, K. & De Clerq, E., 1998, *Antiviral Chem. Chemother.* 9, 187–203). However, the ability of HIV to rapidly evolve drug resistance, together with toxicity problems, requires the development of additional classes of antiviral drugs. Integrase is an attractive target for antivirals because it is essential for HIV replication and, unlike protease and reverse transcriptase, there are no known counterparts in the host cell. Furthermore, integrase uses a single active site to accommodate two different configurations of DNA substrates, which may constrain the ability of HIV to develop drug resistance to integrase inhibitors. However, unlike protease and reverse transcriptase, for which several classes of inhibitors have been developed and cocrystal structures have been determined, progress with the development of integrase inhibitors has been slow. A major obstacle has been the absence of good lead compounds that can serve as the starting point for structure-based inhibitor development. Although numerous compounds have been reported to inhibit integrase activity in vitro, most of these compounds exhibit little specificity for integrase and are not useful as lead compounds (Pommier, Y., Pilon, A. A., Bajaj K, K., Mazumder, A. & Neamati, N., 1997, *Antiviral Chem. Chemother* 8).

HIV-1 integrase is a 32-kDa enzyme that carries out DNA integration in a two-step reaction (Brown, P. O., ibid.). In the first step, called 3' processing, two nucleotides are removed from each 3' end of the viral DNA made by reverse transcription. In the next step, called DNA strand transfer, a pair of transesterification reactions integrates the ends of the viral DNA into the host genome. Integrase is comprised of three structurally and functionally distinct domains, and all three domains are required for each step of the integration reaction (Engelman, A. Bushman, F. D. & Craigie, R., 1993, *EMBO J.* 12, 3269–3275). The isolated domains form homodimers in solution, and the three-dimensional structures of all three separate dimers have been determined (Dyda, F., Hickman, A. B. Jenkins, T. M., Engelman, A., Craigie, R. & Davies, D. R., 1994, *Science* 226, 1981–1986; Goldgur, Y. Dyda, Hickman, A. B., Jenkins, T. M., Craigie, R. & Davies, D. R., 1998, *Proc. Natl. Acad. Sci., USA* 95, 9150–9154; Maignan, S., Guilloteau, J. P., Zhou-Liu, Q., Clement-Mella, C. & Mikol, V., 1998, *J. Mol. Biol.* 282, 259–368; Lodi, P. J., Ernst, J. A., Kuszewski, J., Hickman, A. B., Engelman, A., Craigie, R., Clore, G. M. & Gronenborn, A. M. 1995 *Biochemistry* 34, 9826–9833; Eijkelenboom, A. P., Lutzke, R. A., Boelens, R., Plasterk, R. H., Kaptein, R. & Hard, K. 1995 *Nat. Struct. Biol.* 2, 807–810; Cai, M. L., Zheng, R., Caffrey, M., Craigie, R., Clore, G. M. & Gronenborn, A. M., 1997 *Nat. Struct. Biol.* 4, 839–840). Although little is known concerning the organization of these domains in the active complex with DNA substrates, integrase is likely to function as at least a tetramer (Dyda, F., Hickman, A. B. Jenkins, T. M., Engelman, A., Craigie, R. & Davies, D. R., 1994, *Science* 226, 1981–1986). Extensive mutagenesis studies mapped the catalytic site to the core domain (residues 50–212), which contains the catalytic residues D64, D116, and E152 (Engelman, A. & Craigie R., 1992, *J. Virol.* 66, 6361–6369; Kulkosky, J., Jones, K. S., Katz, R. A., Mack, J. P. & Skalka, A. M., 1992, *Mol. Cell Biol* 12, 2331–2338). The structure of this domain of HIV-1 integrase has been determined in several crystal forms (Dyda, F., Hickman, A. B. Jenkins, T. M., Engelman, A., Craigie, R. & Davies, D. R., 1994, *Science* 226, 1981–1986; Goldgur, Y. Dyda, Hickman, A. B., Jenkins, T. M., Craigie, R. & Davies, D. R., 1998, *Proc. Natl. Acad. Sci., USA* 95, 9150–9154; Maignan, S., Guilloteau, J. P., Zhou-Liu, Q., Clement-Mella, C. & Mikol, V., 1998, *J. Mol. Biol.* 282, 259–368).

Hazuda et al. (Science 287: 646–650, 2000) have described compounds (termed L-731, 988 and L-708,906) which specifically inhibit the strand-transfer activity of HIV-1 integrase and HIV-1 replication in vitro. Viruses grown in the presence of these inhibitors display reduced inhibitor susceptibility and bear mutations in the integrase coding region at amino acid positions 66 (T66I), 153 (S153Y), and 154 (M154I). Site-directed mutants of a laboratory strain of HIV-1 (HXB2) with these amino acid changes confirmed their direct role in conferring reduced integrase inhibitor susceptibility. In addition some of these mutants displayed delayed growth kinetics, suggesting that viral fitness was impaired.

It is an object of this invention to provide a drug susceptibility and resistance test capable of showing whether a viral population in a patient is either more or less susceptible to a given prescribed drug. Another object of this invention is to provide a test that will enable the physician to substitute one or more drugs in a therapeutic regimen for viruses that show altered susceptibility to a given drug or drugs after a course of therapy. Yet another object of this invention is to provide a test that will enable selection of an effective drug regimen for the treatment of HIV infections and/or AIDS. Yet another object of this invention is to provide the means for identifying alterations in the drug susceptibility profile of a patient's virus, in particular identifying changes in susceptibility to protease inhibitors. Still another object of this invention is to provide a test and methods for evaluating the biological effectiveness of candidate drug compounds which act on specific viruses, viral genes and/or viral proteins particularly with respect to alterations in viral drug susceptibility associated with protease inhibitors. It is also an object of this invention to provide the means and compositions for evaluating HIV antiretroviral drug resistance and susceptibility.

It is an object of this invention to provide a method for measuring replication fitness which can be adapted to viruses, including, but not limited to human immunodeficiency virus (HIV), hepadnaviruses (human hepatitis B virus), flaviviruses (human hepatitis C virus) and herpesviruses (human cytomegalovirus). This and other objects of this invention will be apparent from the specification as a whole.

SUMMARY OF THE INVENTION

The present invention relates to methods of monitoring, via phenotypic and genotypic methods the clinical progression of human immunodeficiency virus infection and its response to antiviral therapy. The invention is also based, in part, on the discovery that genetic changes in HIV protease (PR) which confer changes in susceptibility to antiretroviral therapy may be rapidly determined directly from patient plasma HIV RNA using phenotypic or genotypic methods. The methods utilize nucleic acid amplification based assays, such as polymerase chain reaction (PCR). Herein-after, such nucleic acid amplification based assays will be referred to as PCR based assays. This invention is based in part on the discovery of mutations at codons 10, 20, 36, 46, 63, 77 and 88 of HIV protease in PRI treated patients in which the presence of certain combinations of these mutations correlate with changes in certain PRI susceptibilities. This invention is also based on the discovery that susceptibility to HIV protease antivirals may not be altered even if primary mutations are present. Additional mutations at secondary positions in HIV protease are required for a reduction in virus susceptibility. This invention established for the first time that a mutation at position 82 of protease (V82A, F, S, or T) in the absence of another primary mutation was not correlated with a reduction in drug susceptibility. Decreased susceptibility to protease inhibitors, such as indinavir and saquinavir, in viruses containing V82A, F, S or T was observed in viruses with additional mutations at secondary positions, such as, 24, 71, 54, 46, 10 and/or 63 as described herein. Decreased susceptibility to protease inhibitors, such as indinavir and saquinavir, in viruses containing V82A, F, S or T was also observed in viruses with at least 3 or more additional mutations at secondary positions. This inventions also established for the first time that a mutation at position 90 of protease (L90M) in the absence of another primary mutation was not correlated with a reduction in drug susceptibility. Decreased susceptibility to protease inhibitors, such as indinavir and saquinavir, in viruses containing L90M was observed in viruses with additional mutations at secondary positions, such as, 73, 71, 77, and/or 10 as described herein. Decreased susceptibility to protease inhibitors, such as indinavir and saquinavir, in viruses containing L90M was also observed in viruses with at least 3 or more additional mutations at secondary positions. The mutations were found in plasma HIV nucleic acid after a period of time following the initiation of therapy. The development of these mutations, or combinations of these mutations, in HIV PR was found to be an indicator of the development of alterations in phenotypic susceptibility/resistance, which can be associated with virologic failure and subsequent immunological response.

In one embodiment of the invention, a method of assessing the effectiveness of protease antiretroviral therapy of an HIV-infected patient is provided comprising: (a) collecting a plasma sample from the HIV-infected patient; (b) evaluating whether the plasma sample contains nucleic acid encoding HIV protease having a mutation at primary and secondary positions; and (c) determining changes in susceptibility to a protease inhibitor.

In a further embodiment of the invention, PCR based assays, including phenotypic and genotypic assays, may be used to detect a substitution at codon 88 from asparagine to a serine residue either alone or in combination with one or more mutations at other codons selected from the group consisting of 10, 20, 36, 46, 63 and/or 77 or a combination thereof of HIV PR. A mutation at codon 88 from an asparagine residue to a serine residue (N88S) alone correlates with an increase in susceptibility to amprenavir and a mutation at codon 88 from an asparagine residue to a serine residue in combination with mutations at codons 63 and/or 77 or a combination thereof correlates with an increase in susceptibility to amprenavir and a decrease in nelfinavir and indinavir susceptibility.

In a further embodiment of the invention, PCR based assays, including phenotypic and genotypic assays, may be used to detect mutations at codons 10, 20, 36, 46, 63, 77, and 88 of HIV PR which correlate with changes in susceptibility to antiretroviral therapy and immunologic response. Once mutations at these loci have been detected in a patient undergoing PRI antiretroviral therapy, an alteration in the therapeutic regimen should be considered. The timing at which a modification of the therapeutic regimen should be made, following the assessment of antiretroviral therapy using PCR based assays, may depend on several factors including the patient's viral load, CD4 count, and prior treatment history.

In a further embodiment of the invention, PCR based assays, including phenotypic and genotypic assays, may be used to detect a substitution at codon 82 from valine to an alanine (V82A), phenylalanine (V82F), serine (V82S), or threonine (V82T) residue either alone or in combination with one or more mutations at other codons, referred to herein as secondary mutations, selected from the group consisting of 20, 24, 36, 71, 54, 46, 63 and/or 10 or a combination thereof of HIV PR. A mutation at codon 82 from a valine residue to a alanine, phenylalanine, serine or threonine alone correlates with susceptibility to certain protease inhibitors including indinavir and saquinavir. A mutation at codon 82 from a valine residue to a alanine, phenylalanine, serine or threonine in combination with secondary mutations at codons 24 and/or 71 or 20 and/or 36 correlates with a reduction in susceptibility to indinavir and saquinavir, respectively. A mutation at codon 82 from a valine residue to a alanine, phenylalanine, serine or threonine in combination with at least 3 secondary mutations correlates with a reduction in susceptibility to indinavir and saquinavir.

In a further embodiment of the invention, PCR based assays, including phenotypic and genotypic assays, may be used to detect a substitution at codon 90 from leucine to a methionine (L90M) residue either alone or in combination with one or more mutations at other codons, referred to herein as secondary mutations, selected from the group consisting of 73, 71, 46 and/or 10 or a combination thereof of HIV PR. A mutation at codon 90 from a leucine residue to a methionine alone correlates with susceptibility to certain protease inhibitors including indinavir and saquinavir. A mutation at codon 90 from a leucine residue to a methionine in combination with secondary mutations at codons 73 and/or 71 or 73, 71 and/or 77 correlates with a reduction in susceptibility to indinavir and saquinavir, respectively. A mutation at codon 90 from a leucine residue to a methionine in combination with at least 3 secondary mutations correlates with a reduction in susceptibility to indinavir and saquinavir.

In another aspect of the invention there is provided a method for assessing the effectiveness of a protease inhibitor antiretroviral drug comprising: (a) introducing a resistance test vector comprising a patient-derived segment and an indicator gene into a host cell; (b) culturing the host cell from step (a); (c) measuring expression of the indicator gene in a target host cell wherein expression of the indicator gene is dependent upon the patient derived segment; and (d) comparing the expression of the indicator gene from step (c) with the expression of the indicator gene measured when steps (a)–(c) are carried out in the absence of the PRI anti-HIV drug, wherein a test concentration of the PRI, anti-HIV drug is presented at steps (a)–(c); at steps (b)–(c) or at step (c).

This invention also provides a method for assessing the effectiveness of protease inhibitor antiretroviral therapy in a patient comprising: (a) developing a standard curve of drug susceptibility for an PRI anti-HIV drug; (b) determining PRI anti-HIV drug susceptibility in the patient using the susceptibility test described above; and (c) comparing the PRI anti-HIV drug susceptibility in step (b) with the standard curve determined in step (a), wherein a decrease in PRI anti-HIV susceptibility indicates development of anti-HIV drug resistance in the patient's virus and an increase in PRI anti-HIV susceptibility indicates drug hypersensitivity in the patient's virus.

This invention also provides a method for evaluating the biological effectiveness of a candidate PRI HIV antiretroviral drug compound comprising: (a) introducing a resistance test vector comprising a patient-derived segment and an indicator gene into a host cell; (b) culturing the host cell from step (a); (c) measuring expression of the indicator gene in a target host cell wherein expression of the indicator gene is dependent upon the patient derived segment; and (d) comparing the expression of the indicator gene from step (c) with the expression of the indicator gene measured when steps (a)–(c) are carried out in the absence of the candidate PRI anti-viral drug compound, wherein a test concentration of the candidate PRI anti-viral drug compound is present at steps (a)–(c); at steps (b)–(c); or at step (c).

The expression of the indicator gene in the resistance test vector in the target cell is ultimately dependent upon the action of the HIV enzymes (PR and RT) encoded by the patient-derived segment DNA sequences. The indicator gene may be functional or non-functional.

In another aspect this invention is directed to antiretroviral drug susceptibility and resistance tests for HIV/AIDS. Particular resistance test vectors of the invention for use in the HIV/AIDS antiretroviral drug susceptibility and resistance test are identified.

Yet another aspect of this invention provides for the identification and assessment of the biological effectiveness of potential therapeutic antiretroviral compounds for the treatment of HIV and/or AIDS. In another aspect, the invention is directed to a novel resistance test vector comprising a patient-derived segment further comprising one or more mutations on the PR gene and an indicator gene.

Still another aspect of this invention provides for the identification and assessment of the fitness of a virus infecting a patient. In another aspect, the invention is directed to a novel resistance test vector comprising a patient-derived segment further comprising one or more mutations on the PR gene and an indicator gene, enabling the measurement of viral fitness.

Resistance Test Vector. A diagrammatic representation of the resistance test vector comprising a patient derived segment and an indicator gene.

FIG. 2

Two Cell Assay. Schematic Representation of the Assay. A resistance test vector is generated by cloning the patient-derived segment into an indicator gene viral vector. The resistance test vector is then co-transfected with an expression vector that produces amphotropic murine leukemia virus (MLV) envelope protein or other viral or cellular proteins which enable infection. Pseudotyped viral particles are produced containing the protease (PR) and the reverse transcriptase (RT) gene products encoded by the patient-derived DNA sequences. The particles are then harvested and used to infect fresh cells. Using defective PR and RT sequences it was shown that luciferase activity is dependent on functional PR and RT. PR inhibitors are added to the cells following transfection and are thus present during particle maturation. RT inhibitors, on the other hand, are added to the cells at the time of or prior to viral particle infection. The assay is performed in the absence of drug and in the presence of drug over a wide range of concentrations. Luciferase activity is determined and the percentage (%) inhibition is calculated at the different drug concentrations tested.

Figure 3A:
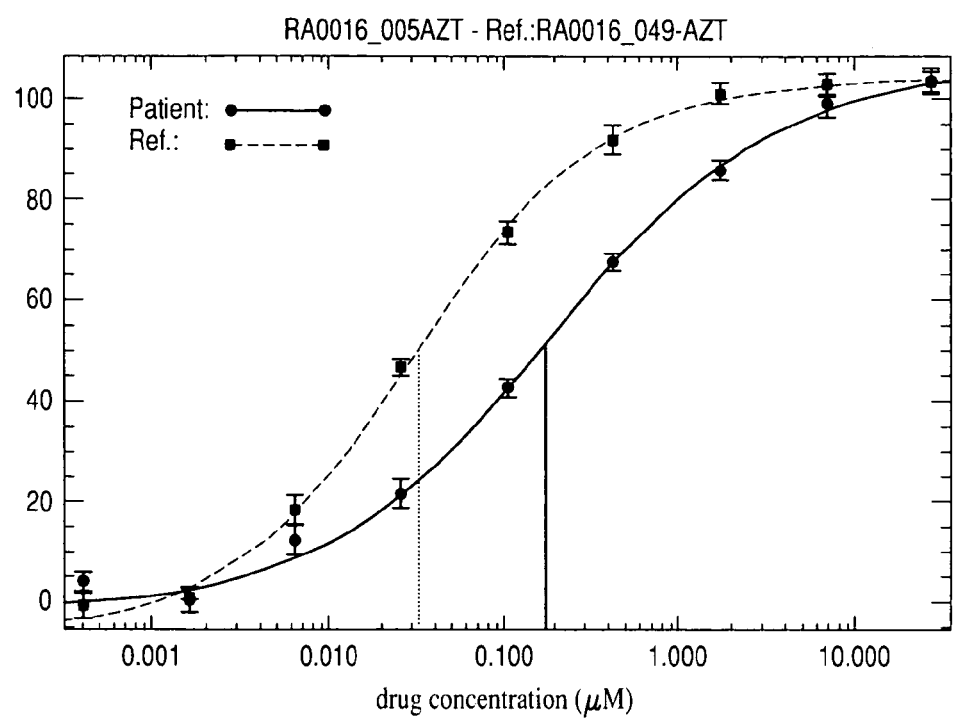
Figure 3B:
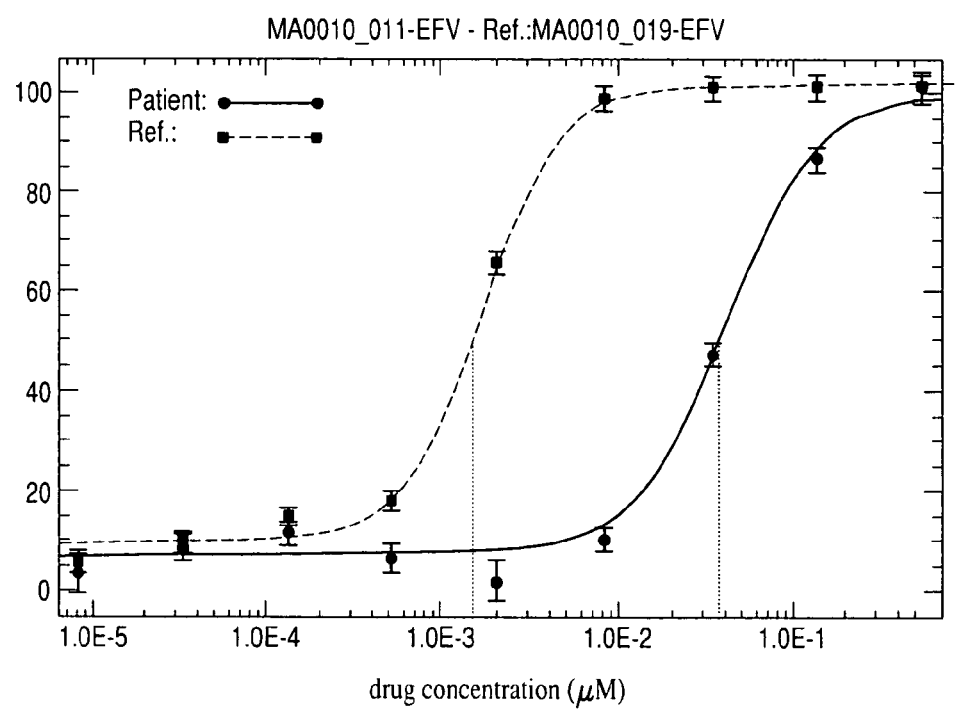
Figure 3C:
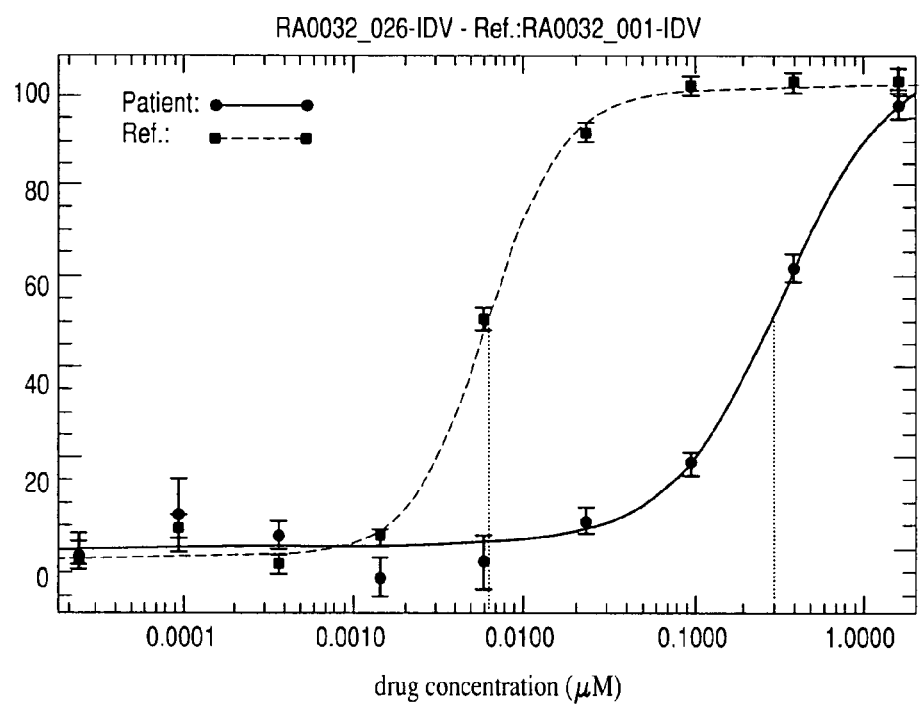

FIGS. 3a–3c

Examples of phenotypic drug susceptibility profiles. Data are analyzed by plotting the percent inhibition of luciferase activity vs. log 10 concentration. This plot is used to calculate the drug concentration that is required to inhibit virus replication by 50% (IC50) or by 95% (IC95). Shifts in the inhibition curves towards higher drug concentrations are interpreted as evidence of drug resistance. FIG. 3a shows the typical curve of drug susceptibility for the nucleoside reverse transcriptase inhibitor AZT. FIG. 3b shows the typical curve of drug susceptibility for the non-nucleoside reverse transcriptase inhibitor efavirenz. Finally, FIG. 3c shows the typical curve of drug susceptibility for the protease inhibitor indinavir. A reduction in drug susceptibility (resistance) is reflected in a shift in the drug susceptibility curve toward higher drug concentrations (to the right) as compared to a baseline (pre-treatment) sample or a drug susceptible virus reference control, such as pNL4-3 or HXB-2, when a baseline sample is not available.

FIGS. 4a–e

Figure 4A:
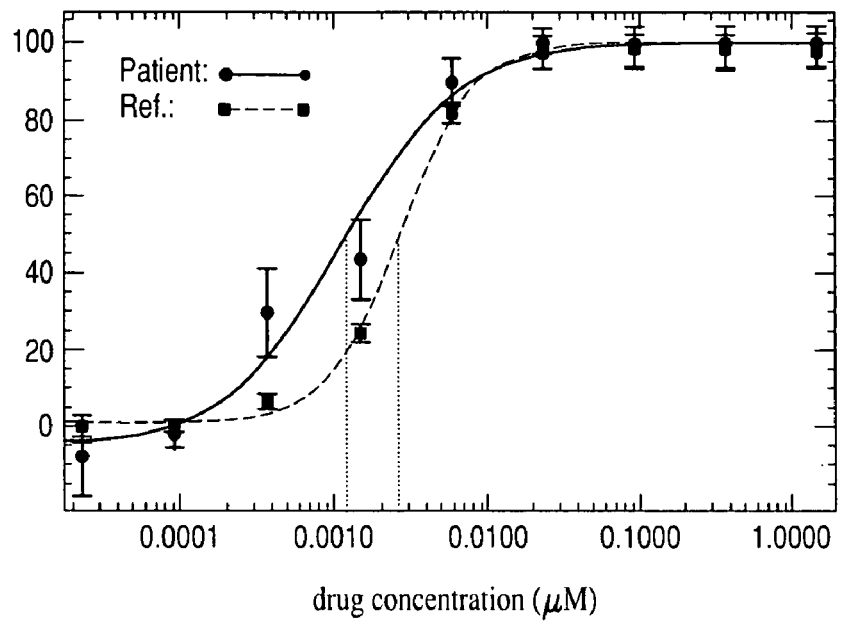
Figure 4B:
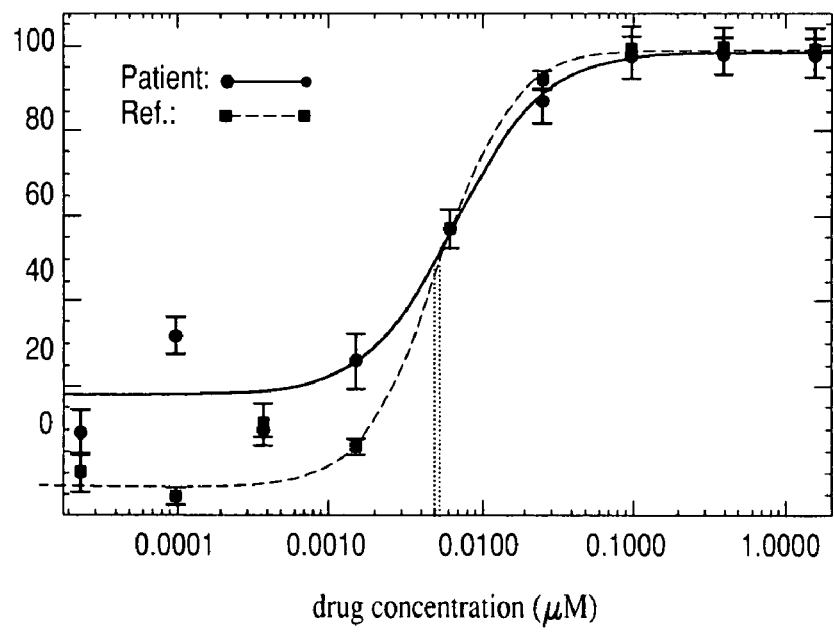
Figure 4C:
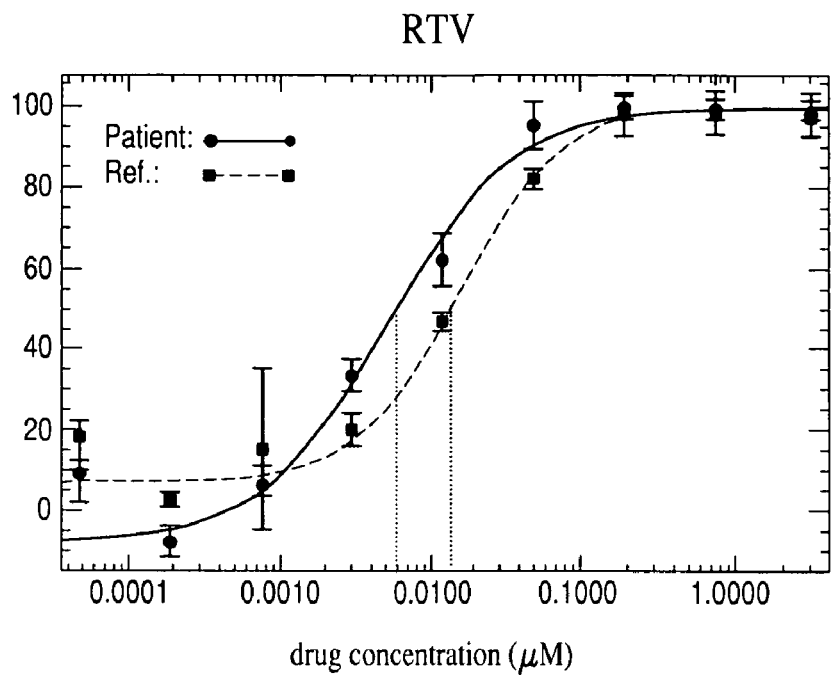
Figure 4D:
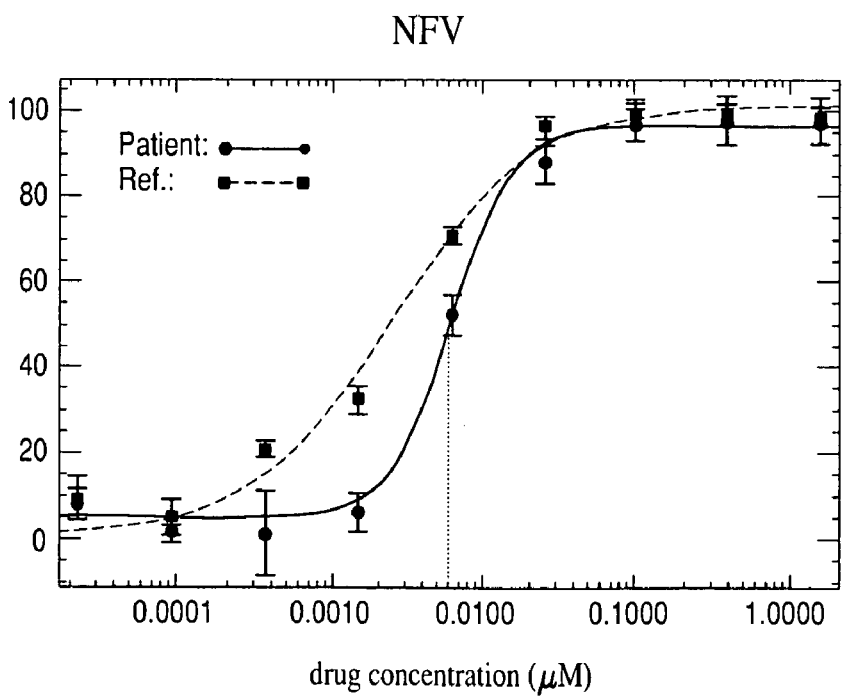
Figure 4E:
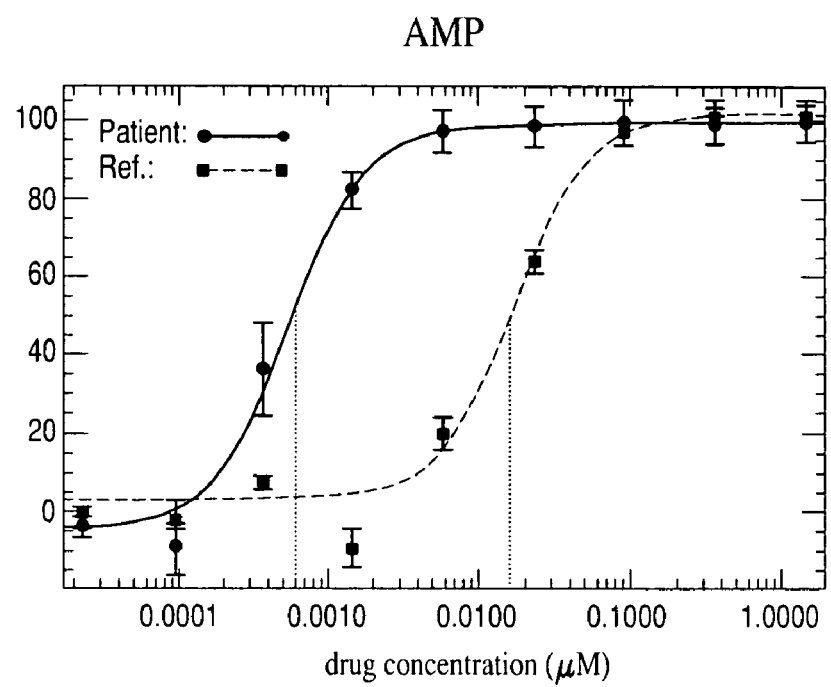

Phenotypic PRI susceptibility profile: patient 0732. A PCR-based phenotypic susceptibility assay was carried out giving the phenotypic drug susceptibility profile showing decreased susceptibility to nelfinavir and indinavir, and increased susceptibility amprenavir. FIG. 4a shows a dose response relationship in subjects treated with saquinavir. FIG. 4b shows a dose response relationship in subjects treated with indinavir. FIG. 4c shows a dose response relationship in subjects treated with ritonavir. FIG. 4d shows a dose response relationship in subjects treated with nelfinavir. Finally, FIG. 4e shows a dose response relationship in subjects treated with amprenavir.

FIGS. 5a–e

Figure 5A:
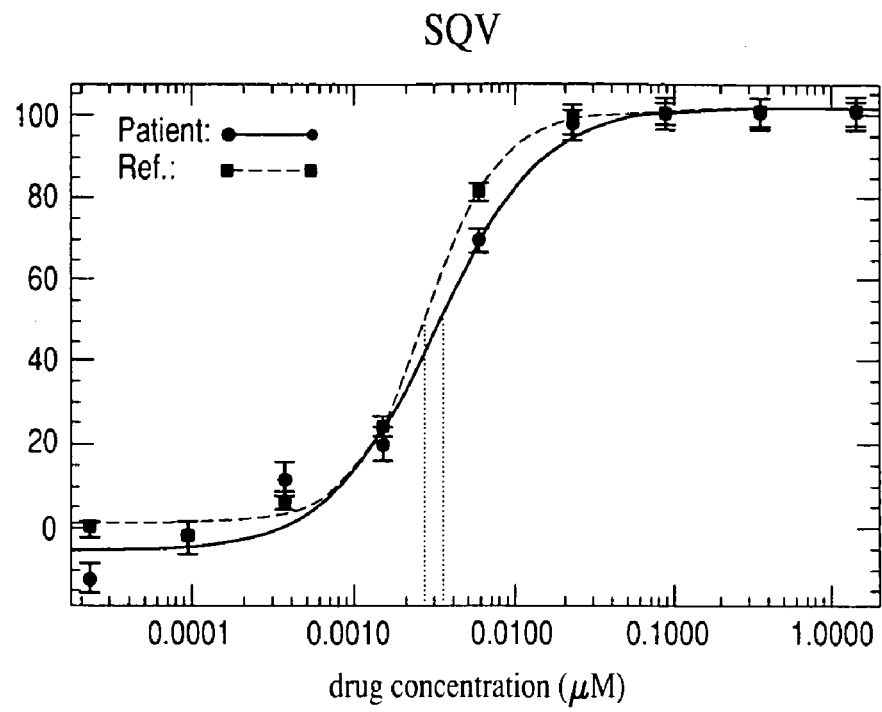
Figure 5B:
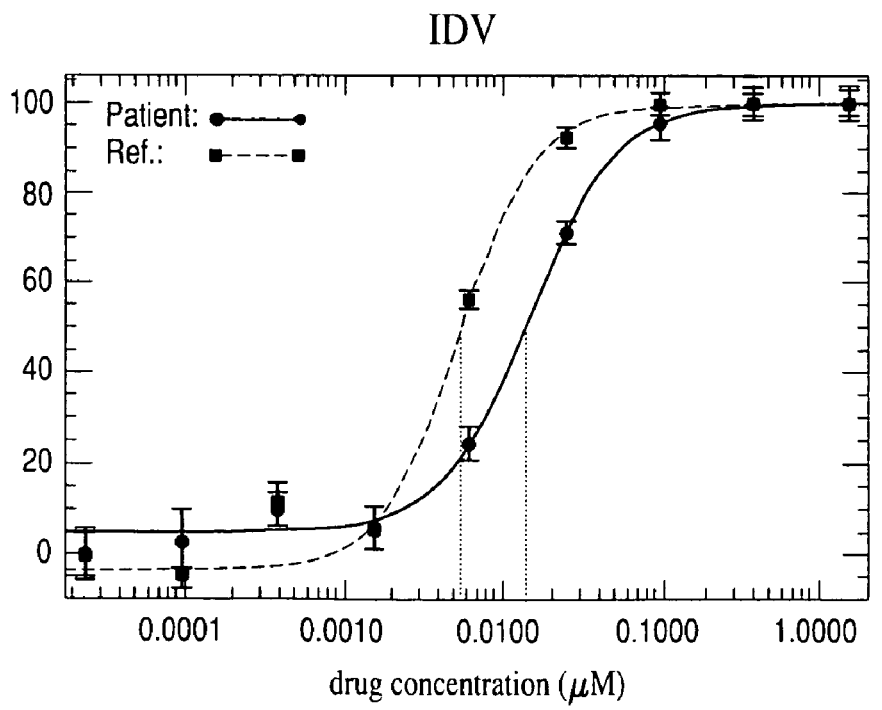
Figure 5C:
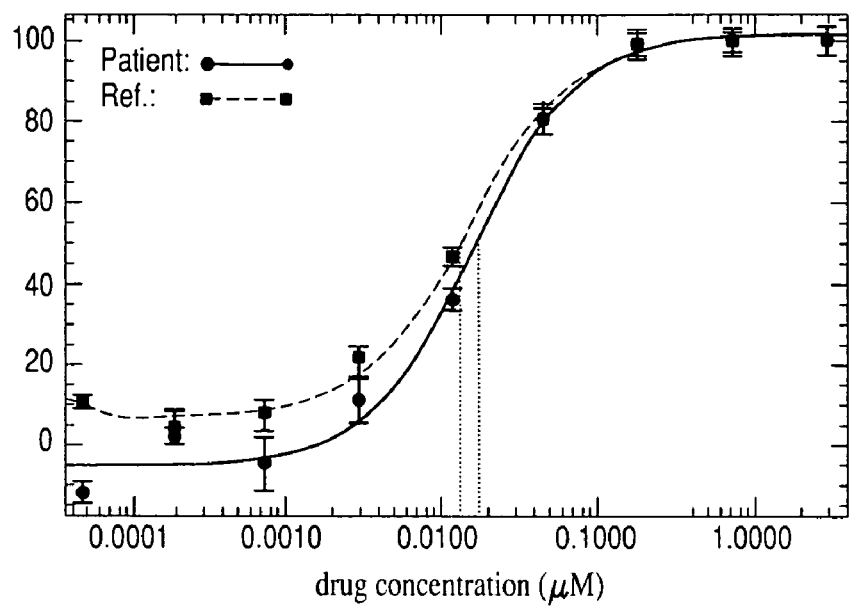
Figure 5D:
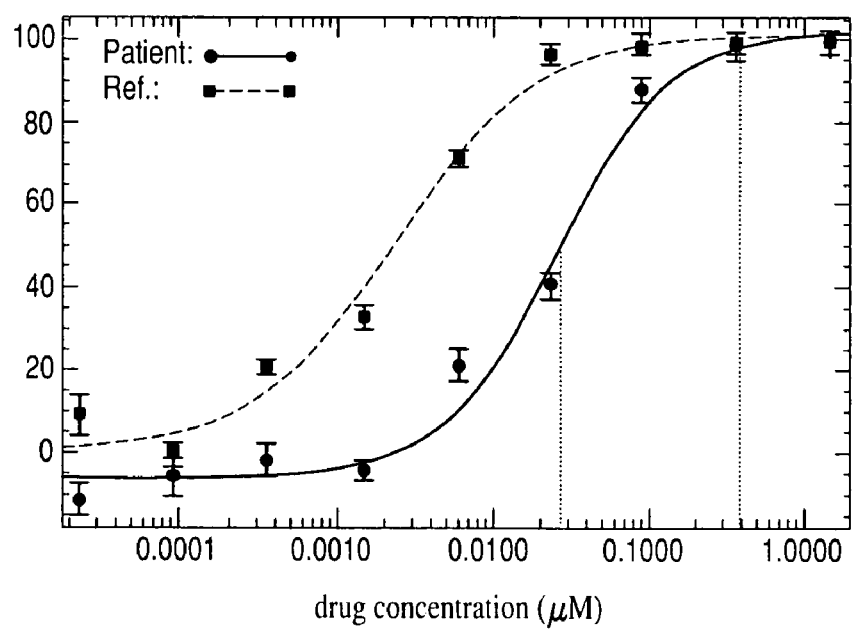
Figure 5E:
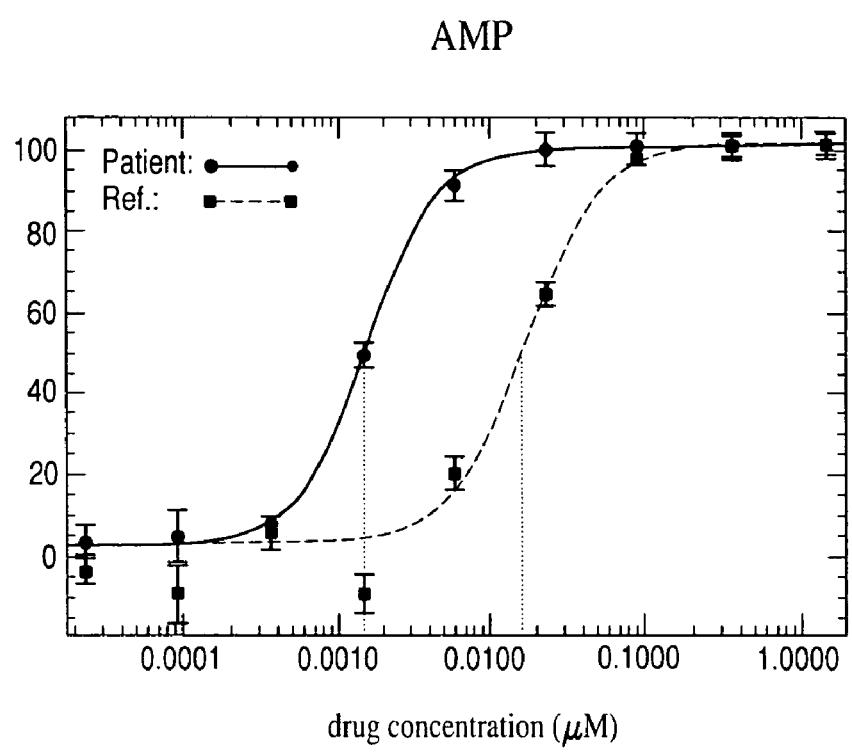

Phenotypic PRI susceptibility profile of a protease mutant generated by site-specific oligonucleotide-directed mutagenesis. A PCR-based phenotypic susceptibility assay was carried out giving the phenotypic drug susceptibility profile of a virus having substitutions at codons 63, 77, and 88 (L63P, V77I, and N88s). The profile demonstrated resistance to both nelfinavir and indinavir, and increased susceptibility to amprenavir. FIG. 5a shows a dose response relationship in subjects treated with saquinavir. FIG. 5b shows a dose response relationship in subjects treated with indinavir. FIG. 5c shows a dose response relationship in subjects treated with ritonavir. FIG. 5d shows a dose response relationship in subjects treated with nelfinavir. Finally, FIG. 5e shows a dose response relationship in subjects treated with amprenavir.

FIG. 6.

Two Cell Fitness Assay. Schematic Representation of the Fitness Assay. A fitness test vector is generated by cloning the patient-derived segment into an indicator gene viral vector. The fitness test vector is then co-transfected with an expression vector that produces amphotropic murine leukemia virus (MLV) envelope protein or other viral or cellular proteins which enable infection. Pseudotyped viral particles are produced containing the protease (PR) and the reverse transcriptase (RT) gene products encoded by the patient-derived DNA sequences. The particles are then harvested and used to infect fresh cells. Using defective PR and RT sequences it was shown that luciferase activity is dependent on functional PR and RT. The fitness assay is typically performed in the absence of drug. If desired, the assay can also be performed at defined drug concentrations. Luciferase activity produced by patient derived viruses is compared to the luciferase activity produced by well-characterized reference viruses. Replication fitness is expressed as a percent of the reference.

FIG. 7

Determining the replication fitness of patient viruses. Virus stocks produced from fitness test vectors derived from patient samples were used to infect cells. Luciferase activity was measured at various times after infection. Patient derived viruses may produce more, approximately the same, or less luciferase activity than the reference virus (Ref) and are said to have greater, equivalent, or reduced replication fitness, respectively. The drug susceptibility profiles of three representative patient derived viruses are shown (P1, P2, P3).

FIG. 8

Identifying alterations in protease or reverse transcriptase function associated with differences in replication fitness of patient viruses. Replication fitness is expressed as a percent of the reference virus (top). Fitness measurements are compared to protease processing of the p55 gag polyprotein (middle) and reverse transcriptase activity (bottom). Protease processing is measured by Western blot analysis using an antibody that reacts with the mature capsid protein (p24). The detection of unprocessed p55 or incompletely processed p41 polyproteins are indicators of reduced cleavage. Reverse transcriptase activity is measured using a quantitative RT-PCR assay and is expressed as a percent of the reference virus.

FIG. 9

Correlating reduced replication fitness with reduced reverse transcriptase activity. Viruses containing various amino acid substitutions at position 190 (A, S, C, Q, E, T, V) of reverse transcriptase were constructed using site directed mutagenesis. The reference virus contains G at this position. Replication fitness and reverse transcriptase activities were compared.

FIG. 10

Correlating reduced replication fitness with reduced protease processing of p55 gag. Viruses containing various amino acid substitutions in protease (D30N, L90M, etc) were constructed using site directed mutagenesis. Replication fitness and p55 gag processing were compared.

FIG. 11

Correlating reduced replication fitness with reduced drug susceptibility. A large collection (n=134) of patient samples were evaluated for phenotypic drug susceptibility and replication fitness. Replication fitness and drug susceptibility were compared.

FIG. 12

Relationship between protease inhibitor susceptibility and replication fitness. Patient samples were sorted based on their replication fitness (<25% of reference, 26–75% of reference, and >75% of reference). Mean values for protease inhibitor susceptibility were determined for each fitness group and plotted for each drug and all drugs combined.

FIG. 13

Relationship between reverse transcriptase inhibitor susceptibility and replication fitness. Patient samples were sorted based on their replication fitness (<25% of reference, 26–75% of reference, and >75% of reference). Mean values for reverse transcriptase susceptibility were determined for each fitness group and plotted for each drug and all drugs combined.

FIG. 14

Reduced replication fitness is associated with high numbers of protease mutations, and the L90M mutation. Patient viruses were sorted based on the number of protease mutations. Viruses with large numbers of protease mutations or the L90M protease mutation generally exhibit reduced replication fitness.

FIG. 15

Low replication capacity is associated with specific protease mutations. Patient viruses were sorted based on replication capacity. Specific protease mutations either alone (D30N) or in combination (L90M plus others) were observed with high frequency in viruses with reduced replication fitness.

FIG. 16

Relationship between nelfinavir susceptibility, protease processing and replication fitness. Patient viruses were sorted based on nelfinavir susceptibility (<10 or >10 of reference). Protease processing and replication fitness were plotted for all patient viruses. Viruses with reduced nelfinavir susceptibility generally exhibited reduced protease processing and reduced replication fitness.

Figure 17:
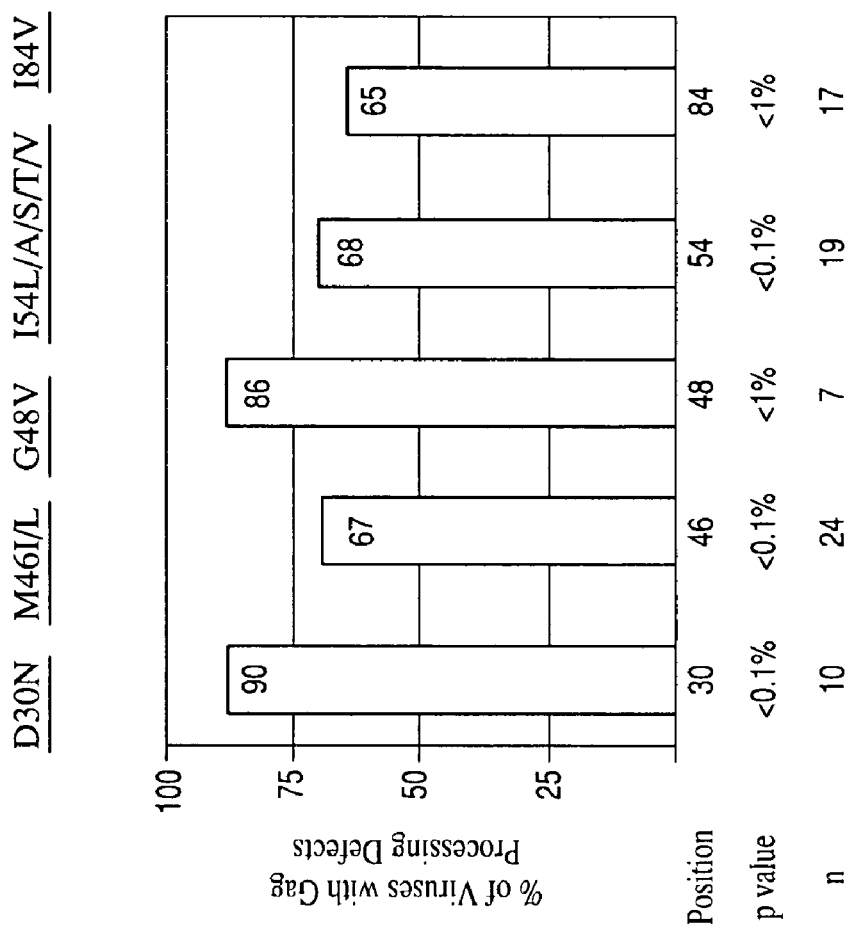

FIG. 17 Protease mutations associated with reduced protease processing. Patient viruses were sorted based on protease processing. Specific protease mutations were observed at high frequency in viruses with reduced protease processing.

FIG. 18

Representative patient sample exhibiting reversion to drug susceptibility during a period of drug treatment interruption. Virus samples were collected weekly during a period of treatment interruption and evaluated for phenotypic drug susceptibility. Values shown represent fold change in susceptibility compared to the reference virus.

FIG. 19

Representative patient sample exhibiting increased replication fitness during a period of drug treatment interruption. Virus samples were collected weekly during a period of treatment interruption and evaluated for phenotypic drug susceptibility. Fitness values shown represent percent of the reference virus. The increase in fitness between week 9 and week 10 corresponds to improved protease processing (bottom) and reversion of the drug resistant phenotype to a drug sensitive phenotype (Figure M).

FIG. 20

Increased replication fitness during treatment interruption. Replication fitness was measured at the time of treatment interruption and various times during the period of treatment interruption. Generally, replication fitness was significantly higher in samples that corresponded to timepoints after the virus had reverted from a drug resistant phenotype to a drug sensitive phenotype.

FIG. 21

Figure 21:
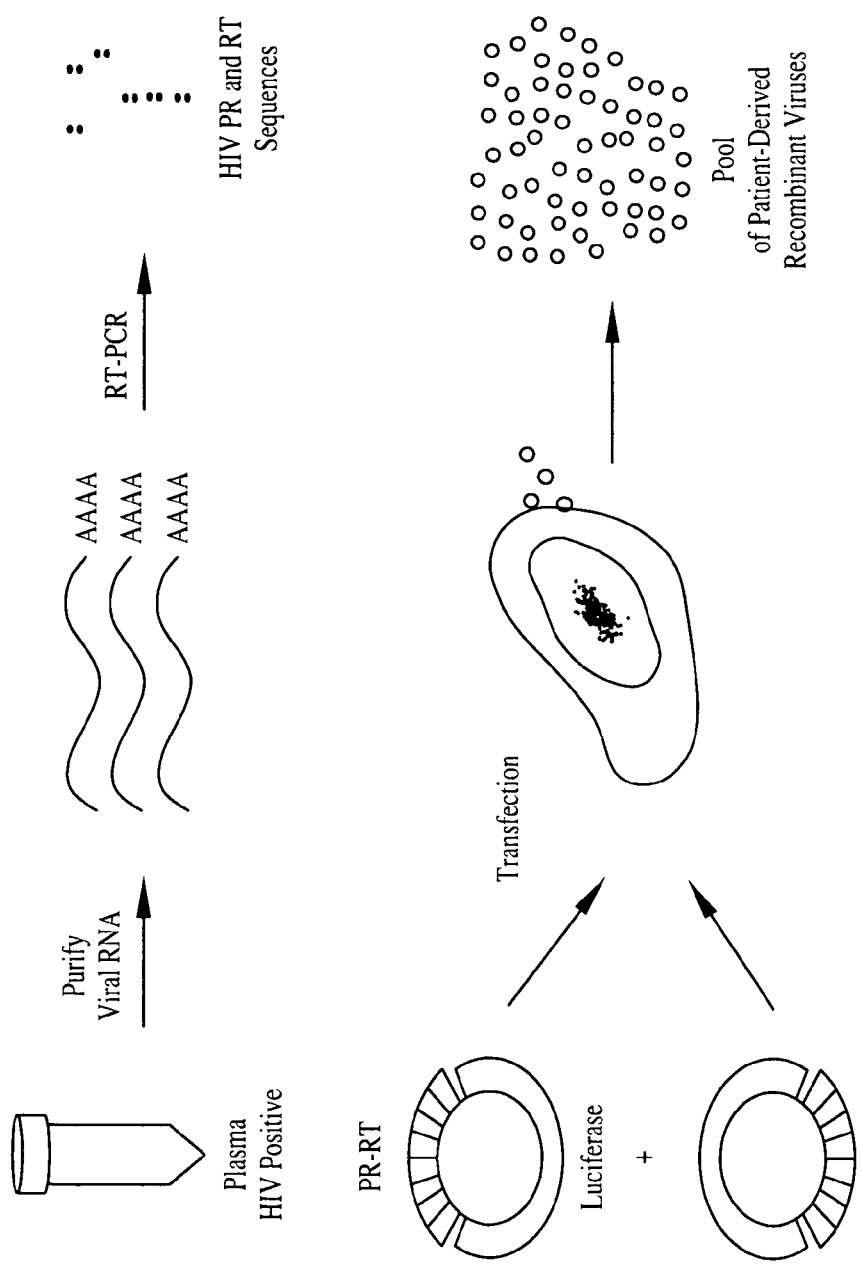

FIG. 21 shows a way to measure the replication capacity of patient-derived recombinant viruses.

FIG. 22

Figure 22:
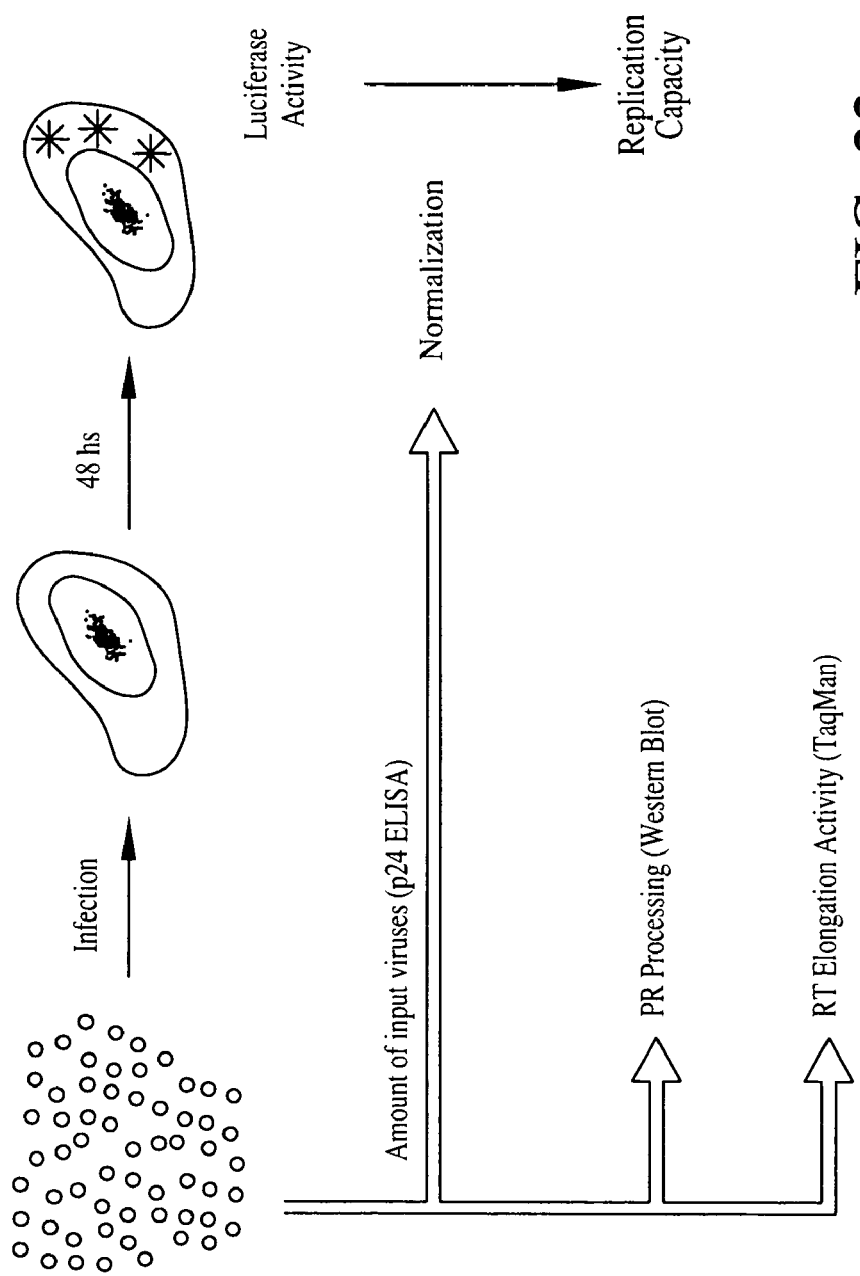

FIG. 22 shows a way to measure the replication capacity of patient-derived recombinant viruses.

DETAILED DESCRIPTION OF THE INVENTION

The present invention relates to methods of monitoring the clinical progression of HIV infection in patients receiving antiretroviral therapy, particularly protease inhibitor antiretroviral therapy.

In one embodiment, the present invention provides for a method of evaluating the effectiveness of antiretroviral therapy of a patient comprising (i) collecting a biological sample from an HIV-infected patient; and (ii) determining whether the biological sample comprises nucleic acid encoding HIV PR having a mutation at one or more positions in the PR. The mutation(s) correlate positively with alterations in phenotypic susceptibility.

In a specific embodiment, the invention provides for a method of evaluating the effectiveness of PRI antiretroviral therapy of a patient comprising (i) collecting a biological sample from an HIV-infected patient; and (ii) determining whether the biological sample comprises nucleic acid encoding HIV PR having a mutation at codon 88 from an asparagine residue to a serine residue (N88S). This invention established, using a phenotypic susceptibility assay, that a mutation at codon 88 to a serine residue of HIV protease is correlated with an increase in amprenavir susceptibility.

In a specific embodiment, the invention provides for a method of evaluating the effectiveness of PRI antiretroviral therapy of a patient comprising (i) collecting a biological sample from an HIV-infected patient; and (ii) determining whether the biological sample comprises nucleic acid encoding HIV PR having a mutation at codon 88 from an asparagine residue to a serine residue (N88S) either alone or in combination with mutations at codons 63 and/or 77 or a combination thereof. This invention established, using a phenotypic susceptibility assay, that a mutation at codon 88 to a serine residue of HIV protease is correlated with an increase in amprenavir susceptibility and a mutation at codon 88 to a serine residue in combination with mutations at codons 63 and/or 77 or a combination thereof of HIV protease are correlated with an increase in amprenavir susceptibility and a decrease in nelfinavir and indinavir susceptibility.

In a specific embodiment, the invention provides for a method of evaluating the effectiveness of PRI antiretroviral therapy of a patient comprising (i) collecting a biological sample from an HIV-infected patient; and (ii) determining whether the biological sample comprises nucleic acid encoding HIV PR having a mutation at codon 88 from an asparagine residue to a serine residue (N88S) either alone or in combination with mutations at codons 46, 63 and/or 77 or a combination thereof. This invention established, using a phenotypic susceptibility assay, that a mutation at codon 88 to a serine residue of HIV protease is correlated with an increase in amprenavir susceptibility and a mutation at codon 88 to a serine residue in combination with mutations at codons 46, 63 and/or 77 or a combination thereof of HIV protease are correlated with an increase in amprenavir susceptibility and a decrease in nelfinavir and indinavir susceptibility.

In a specific embodiment, the invention provides for a method of evaluating the effectiveness of PRI antiretroviral therapy of a patient comprising (i) collecting a biological sample from an HIV-infected patient; and (ii) determining whether the biological sample comprises nucleic acid encoding HIV PR having a mutation at codon 88 from an asparagine residue to a serine residue (N88S) either alone or in combination with mutations at codons 10, 20, 36, 46, 63 and/or 77 or a combination thereof. This invention established, using a phenotypic susceptibility assay, that a mutation at codon 88 to a serine residue of HIV protease is correlated with an increase in amprenavir susceptibility and a mutation at codon 88 to a serine residue in combination with mutations at codons 10, 20, 36, 46, 63 and/or 77 or a combination thereof of HIV protease are correlated with an increase in amprenavir susceptibility and a decrease in nelfinavir and indinavir susceptibility.

Under the foregoing circumstances, the phenotypic susceptibility profile and genotypic profile of the HIV virus infecting the patient has been altered reflecting a change in response to the antiretroviral agent. In the case of PRI antiretroviral therapy, the HIV virus infecting the patient may be resistant to one or more PRI s but hypersensitive to another of the PRI s as described herein. It therefore may be desirable after detecting the mutation(s), to either increase the dosage of the antiretroviral agent, change to another antiretroviral agent, or add one or more additional antiretroviral agents to the patient's therapeutic regimen. For example, if the patient was being treated with nelfinavir when the N88S mutation arose, the patient's therapeutic regimen may desirably be altered by either (i) changing to a different PRI antiretroviral agent, such as saquinavir, ritonavir or amprenavir and stopping nelfinavir treatment; or (ii) increasing the dosage of nelfinavir; or (iii) adding another antiretroviral agent to the patient's therapeutic regimen. The effectiveness of the modification in therapy may be further evaluated by monitoring viral burden such as by HIV RNA copy number. A decrease in HIV RNA copy number correlates positively with the effectiveness of a treatment regimen.

The phrase "correlates positively," as used herein, indicates that a particular result renders a particular conclusion more likely than other conclusions.

When reference is made to a particular codon number, it is understood that the codon number refers to the position of the amino acid that the codon codes for. Therefore a codon referencing a particular number is equivalent to a "postion" referencing a particular number, such as for example, "codon 88" or "position 88".

Another preferred, non-limiting, specific embodiment of the invention is as follows: A method of evaluating the effectiveness of PRI therapy of a patient comprising (i) collecting a biological sample from an HIV-infected patient; (ii) purifying and converting the viral RNA to cDNA and amplifying HIV sequences using HIV primers that result in a PCR product that comprises the PR gene; (iii) performing PCR using primers that result in PCR products comprising wild type or serine at codon 88; and (iv) determining, via the products of PCR, the presence or absence of a serine residue at codon 88.

Another preferred, non-limiting, specific embodiment of the invention is as follows: A method of evaluating the effectiveness of PRI therapy of a patient comprising (i) collecting a biological sample from an HIV-infected patient; (ii) purifying and converting the viral RNA to cDNA and amplifying HIV sequences using HIV primers that result in a PCR product that comprises the PR gene; (iii) performing PCR using primers that result in PCR products comprising wild type or serine at codon 88 and mutations at codons 63 and/or 77; and (iv) determining, via the products of PCR, the presence or absence of a serine residue at codon 88 and the presence or absence of mutations at codons 63 and/or 77.

Another preferred, non-limiting, specific embodiment of the invention is as follows: A method of evaluating the effectiveness of PRI therapy of a patient comprising (i) collecting a biological sample from an HIV-infected patient; (ii) purifying and converting the viral RNA to cDNA and amplifying HIV sequences using HIV primers that result in a PCR product that comprises the PR gene; (iii) performing PCR using primers that result in PCR products comprising wild type or serine at codon 88 and mutations at codons 63, 77 and/or 46 or a combination thereof; and (iv) determining, via the products of PCR, the presence or absence of a serine residue at codon 88 and the presence or absence of mutations at codons 63, 77 and/or 46 or a combination thereof.

Another preferred, non-limiting, specific embodiment of the invention is as follows: A method of evaluating the effectiveness of PRI therapy of a patient comprising (i) collecting a biological sample from an HIV-infected patient; (ii) purifying and converting the viral RNA to cDNA and amplifying HIV sequences using HIV primers that result in a PCR product that comprises the PR gene; (iii) performing PCR using primers that result in PCR products comprising wild type or serine at codon 88 and mutations at codons 63, 77, 46, 10, 20, and/or 36 or a combination thereof; and (iv) determining, via the products of PCR, the presence or absence of a serine residue at codon 88 and the presence or absence of mutations at codons 63, 77, 46, 10, 20, and/or 36 or a combination thereof.

The presence of the mutation at codon 88 to a serine of HIV PR indicates that the effectiveness of the current or prospective PRI therapy may require alteration, since as shown by this invention mutation at codon 88 to a serine residue increases the susceptibility to amprenavir. Using the methods of this invention, changes in the PRI therapy would be indicated.

The presence of the mutation at codon 88 to a serine of alone or in combination with mutations at condons 63, 77, 46, 10, 20, and/or 36 or a combination thereof of HIV PR indicates that the effectiveness of the current or prospective PRI therapy may require alteration, since as shown by this invention a mutation at codon 88 to a serine residue alone increases the susceptibility to amprenavir and a mutation at codon 88 to a serine residue in combination with mutations at condons 63, 77, 46, 10, 20, and/or 36 or a combination increases the susceptibility to amprenavir but also reduces the susceptibility to nelfinavir and indinavir. Using the methods of this invention, changes in the PRI therapy would be indicated.

Another preferred, non-limiting, specific embodiment of the invention is as follows: a method of evaluating the effectiveness of antiretroviral therapy of an HIV-infected patient comprising: (a) collecting a biological sample from an HIV-infected patient; and (b) determining whether the biological sample comprises nucleic acid encoding HIV protease having a mutation at codon 88 to serine. Using the phenotypic susceptibility assay, it was observed that the presence of the mutation at codon 88 to serine of HIV PR causes a an increase in amprenavir susceptibility.

Another preferred, non-limiting, specific embodiment of the invention is as follows: a method of evaluating the effectiveness of antiretroviral therapy of an HIV-infected patient comprising: (a) collecting a biological sample from an HIV-infected patient; and (b) determining whether the biological sample comprises nucleic acid encoding HIV protease having a mutation at codon 88 to serine and additional mutation(s) at codons 63 and/or 77 or a combination thereof. Using the phenotypic susceptibility assay, it was observed that the presence of the mutation at codon 88 to serine of HIV PR causes an increase in amprenavir susceptibility and the presence of the mutations at codon 88 to serine in combination with a mutation at codon(s) 63 and/or 77 or a combination thereof of HIV PR causes a decrease in nelfinavir and indinavir susceptibility while increasing amprenavir susceptibility.

Another preferred, non-limiting, specific embodiment of the invention is as follows: a method of evaluating the effectiveness of antiretroviral therapy of an HIV-infected patient comprising: (a) collecting a biological sample from an HIV-infected patient; and (b) determining whether the biological sample comprises nucleic acid encoding HIV protease having a mutation at codon 88 to serine and additional mutation(s) at codons 63, 77 and/or 46 or a combination thereof. Using the phenotypic susceptibility assay, it was observed that the presence of the mutation at codon 88 to serine of HIV PR causes an increase in amprenavir susceptibility and the presence of the mutations at codon 88 to serine in combination with a mutation at codon(s) 46, 63 and/or 77 or a combination thereof of HIV PR causes a decrease in nelfinavir and indinavir susceptibility while increasing amprenavir susceptibility.

Another preferred, non-limiting, specific embodiment of the invention is as follows: a method of evaluating the effectiveness of antiretroviral therapy of an HIV-infected patient comprising: (a) collecting a biological sample from an HIV-infected patient; and (b) determining whether the biological sample comprises nucleic acid encoding HIV protease having a mutation at codon 88 to serine and additional mutation(s) at codons 63, 77, 46, 10, 20 and/or 36 or a combination thereof. Using the phenotypic susceptibility assay, it was observed that the presence of the mutation at codon 88 to serine of HIV PR causes an increase in amprenavir susceptibility and the presence of the mutations at codon 88 to serine in combination with a mutation at codon(s) 63, 77, 46, 10, 20 and/or 36 or a combination thereof of HIV PR causes a decrease in nelfinavir and indinavir susceptibility while increasing amprenavir susceptibility.

This invention also provides the means and methods to use the resistance test vector comprising an HIV gene and further comprising a PR mutation for drug screening. More particularly, the invention describes the resistance test vector comprising the HIV protease having a mutation at codon 88 to a serine alone or in combination with mutations at codons 10, 20, 36, 46, 63 and/or 77 or a combination thereof for drug screening. The invention further relates to novel vectors, host cells and compositions for isolation and identification of the HIV-1 protease inhibitor resistant mutant and using such vectors, host cells and compositions to carry out anti-viral drug screening. This invention also relates to the screening of candidate drugs for their capacity to inhibit said mutant.

This invention provides a method for identifying a compound which is capable of affecting the function of the protease of HIV-1 comprising contacting the compound with the polypeptide(s) comprising all or part of the HIV-1 protease, wherein codon 88 is changed to a serine residue, wherein a positive binding indicates that the compound is capable of affecting the function of said protease.

This invention also provides a method for assessing the viral fitness of patient's virus comprising: (a) determining the luciferase activity in the absence of drug for the reference control using the susceptibility test described above; (b) determining the luciferase activity in the absence of drug for the patient virus sample using the susceptibility test described above; and (c) comparing the luciferase activity determined in step (b) with the luciferase activity determined in step (a), wherein a decrease in luciferase activity indicates a reduction in viral fitness of the patient's virus.

If a resistance test vector is constructed using a patient derived segment from a patient virus which is unfit, and the fitness defect is due to genetic alterations in the patient derived segment, then the virus produced from cells transfected with the resistance test vector will produce luciferase more slowly. This defect will be manifested as reduced luciferase activity (in the absence of drug) compared to the drug sensitive reference control, and may be expressed as a percentage of the control.

In a further embodiment of the invention, PCR based assays, including phenotypic and genotypic assays, may be used to detect mutations at positions 20 and 88 of HIV PR, which correlate with a reduction in viral fitness and immunological response.

It is a further embodiment of this invention to provide a means and method for measuring replication fitness for viruses, including, but not limited to human immunodeficiency virus (HIV), hepadnaviruses (human hepatitis B virus), flaviviruses (human hepatitis C virus) and herpesviruses (human cytomegalovirus).

This invention further relates to a means and method for measuring the replication fitness of HIV-1 that exhibits reduced drug susceptibility to reverse transcriptase inhibitors and protease inhibitors.

In a further embodiment of the invention, a means and methods are provided for measuring replication fitness for other classes of inhibitors of HIV-1 replication, including, but not limited to integration, virus assembly, and virus attachment and entry.

This invention relates to a means and method for identifying mutations in protease or reverse transcriptase that alter replication fitness.

In a further embodiment of the invention, a means and methods are provided for identifying mutations that alter replication fitness for other components of HIV-1 replication, including, but not limited to integration, virus assembly, and virus attachment and entry.

This invention also relates to a means and method for quantifying the affect that specific mutations in protease or reverse transcriptase have on replication fitness.

In a further embodiment of the invention, a means and method are provided for quantifying the affect that specific protease and reverse transcriptase mutations have on replication fitness in other viral genes involved in HIV-1 replication, including, but not limited to the gag, pol, and envelope genes.

This invention also relates to the high incidence of patient samples with reduced replication fitness.

This invention relates to the correlation between reduced drug susceptibility and reduced replication fitness.

This invention further relates to the occurrence of viruses with reduced fitness in patients receiving protease inhibitor and/or reverse transcriptase inhibitor treatment.

This invention further relates to the incidence of patient samples with reduced replication fitness in which the reduction in fitness is due to altered protease processing of the gag polyprotein (p55).

This invention further relates to the incidence of protease mutations in patient samples that exhibit low, moderate or normal (wildtype) replication fitness.

This invention further relates to protease mutations that are frequently observed, either alone or in combination, in viruses that exhibit reduced replication capacity.

This invention also relates to the incidence of patient samples with reduced replication fitness in which the reduction in fitness is due to altered reverse transcriptase activity. This invention relates to the occurrence of viruses with reduced replication fitness in patients failing antiretroviral drug treatment. This invention further relates to a means and method for using replication fitness measurements to guide the treatment of HIV-1. This invention further relates to a means and method for using replication fitness measurements to guide the treatment of patients failing antiretroviral drug treatment. This invention further relates to the means and methods for using replication fitness measurements to guide the treatment of patients newly infected with HIV-1.

This invention, provides the means and methods for using replication fitness measurements to guide the treatment of viral diseases, including, but not limited to HIV-1, hepadnaviruses (human hepatitis B virus), flaviviruses (human hepatitis C virus) and herpesviruses (human cytomegalovirus).

In a further embodiment, the invention provides a method for determining replication capacity for a patient's virus comprising:
  (a) introducing a resistance test vector comprising a patient derived segment and an indicator gene into a host cell;
  (b) culturing the host cell from (a);
  (c) harvesting viral particles from step (b) and infecting target host cells;
  (d) measuring expression of the indicator gene in the target host cell, wherein the expression of the indicator gene is dependent upon the patient-derived segment;
  (e) comparing the expression of the indicator gene from (d) with the expression of the indicator gene measured when steps (a) through (d) are carried out in a control resistance test vector; and
  (f) normalizing the expression of the indicator gene by measuring an amount of virus in step (c).

As used herein, "patient-derived segment" encompasses segments derived from human and various animal species. Such species include, but are not limited to chimpanzees, horses, cattles, cats and dogs.

Patient-derived segments can also be incorporated into resistance test vectors using any of several alternative cloning techniques as set forth in detail in U.S. Pat. No. 5,837,464 (International Publication Number WO 97/27319) which is hereby incorporated by reference. For example, cloning via the introduction of class II restriction sites into both the plasmid backbone and the patient-derived segments or by uracil DNA glycosylase primer cloning.

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that may be underrepresented in one resistance test vector alone.

"Resistance test vector" means one or more vectors which taken together contain DNA comprising a patient-derived segment and an indicator gene. Resistance test vectors are prepared as described in U.S. Pat. No. 5,837,464 (International Publication Number WO 97/27319), which is hereby incorporated by reference, by introducing patient sequence acceptor sites, amplifying or cloning patient-derived segments and inserting the amplified or cloned sequences precisely into indicator gene viral vectors at the patient sequence acceptor sites. Alternatively, a resistance test vector (also referred to as a resistance test vector system) is prepared by introducing patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

"Indicator or indicator gene," as described in U.S. Pat. No. 5,837,464 (International Publication Number WO 97/27319) refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the *E. coli* lacZ gene which encodes beta-galactosidase, the luc gene which encodes luciferase either from, for example, *Photonis pyralis* (the firefly) or *Renilla reniformis* (the sea pansy), the *E. coli* phoA gene which encodes alkaline phosphatase, green fluorescent protein and the bacterial CAT gene which encodes chloramphenicol acetyltransferase. The indicator or indicator gene may be functional or non-functional as described in U.S. Pat. No. 5,837,464 (International Publication Number WO 97/27319).

The phenotypic drug susceptibility and resistance tests of this invention may be carried out in one or more host cells as described in U.S. Pat. No. 5,837,464 (International Publication Number WO 97/27319) which is incorporated herein by reference. Viral drug susceptibility is determined as the concentration of the anti-viral agent at which a given percentage of indicator gene expression is inhibited (e.g. the IC50 for an anti-viral agent is the concentration at which 50% of indicator gene expression is inhibited). A standard curve for drug susceptibility of a given anti-viral drug can be developed for a viral segment that is either a standard laboratory viral segment or from a drug-naive patient (i.e. a patient who has not received any anti-viral drug) using the method described in the aforementioned patent. Correspondingly, viral drug resistance is a decrease in viral drug susceptibility for a given patient compared to such a given standard or when making one or more sequential measurements in the same patient over time, as determined by decreased susceptibility in virus from later time points compared to that from earlier time points.

The antiviral drugs being added to the test system are added at selected times depending upon the target of the antiviral drug. For example, in the case of HIV protease inhibitors, including saquinavir, ritonavir, indinavir, nelfinavir and amprenavir, they are added to packaging host cells at the time of or shortly after their transfection with a resistance test vector, at an appropriate range of concentrations. HIV reverse transcriptase inhibitors, including AZT, ddI, ddC, d4T, 3TC, abacavir, nevirapine, delavirdine and efavirenz are added to target host cells at the time of or prior to infection by the resistance test vector viral particles, at an appropriate range of concentration. Alternatively, the antiviral drugs may be present throughout the assay. The test concentration is selected from a range of concentrations which is typically between about $8 \times 10^{-6}$ µM and about 2 mM and more specifically for each of the following drugs: saquinavir, indinavir, nelfinavir and amprenavir, from about $2.3 \times 10^{-5}$ µM to about 1.5 µM and ritonavir, from about $4.5 \times 10^{-5}$ µM to about 3 µM.

In another embodiment of this invention, a candidate PRI antiretroviral compound is tested in the phenotypic drug susceptibility and resistance test using the resistance test vector comprising PR having a mutation at codon 88 to a serine. The candidate antiviral compound is added to the test system at an appropriate range of concentrations and at the transfection step. Alternatively, more than one candidate antiviral compound may be tested or a candidate antiviral compound may be tested in combination with an approved antiviral drug such as AZT, ddI, ddC, d4T, 3TC, abacavir, delavirdine, nevirapine, efavirenz, saquinavir, ritonavir, indinavir, nelfinavir, amprenavir, or a compound which is undergoing clinical trials such as adefovir and ABT-378. The effectiveness of the candidate antiviral will be evaluated by measuring the expression or inhibition of the indicator gene. In another aspect of this embodiment, the drug susceptibility and resistance test may be used to screen for viral mutants. Following the identification of mutants resistant to either known antiretrovirals or candidate antiretrovirals the resistant mutants are isolated and the DNA is analyzed. A library of viral resistant mutants can thus be assembled enabling the screening of candidate PRI antiretrovirals, alone or in combination. This will enable one of ordinary skill to identify effective PRI antiretrovirals and design effective therapeutic regimens.

In another embodiment of this invention, a method of assessing the effectiveness of protease antiretroviral therapy of an HIV-infected patient is provided comprising:

(a) collecting a biological sample from the HIV-infected patient;

(b) evaluating whether the biological sample contains nucleic acid encoding HIV protease having a mutation at codon 82 or codon 90; and (c) determining changes in susceptibility to protease inhibitors.

In another embodiment of this invention, the method is provided, wherein step (c) determines changes in susceptibility to saquinavir.

In another embodiment of this invention, the method is provided, wherein the mutation at codon 82 codes for alanine (A), phenylalanine (F), serine (S), or threonine (T).

In another embodiment of this invention, the method is provided, wherein the mutation at codon 82 is a substitution of alanine (A), phenylalanine (F), serine (S), or threonine (T) for valine (V).

In another embodiment of this invention, the method is provided, wherein the mutation at codon 90 codes for methionine (M).

In another embodiment of this invention, the method is provided, wherein the mutation at codon 90 is a substitution of methionine (M) for leucine (L).

In another embodiment of this invention, a method for evaluating the biological effectiveness of a candidate HIV protease antiretroviral drug compound is provided comprising:

(a) introducing a resistance test vector comprising a patient-derived segment having nucleic acid encoding HIV protease with a mutation at codon 82 or codon 90 and an indicator gene into a host cell;

(b) culturing the host cell from step (a);

(c) measuring the indicator gene in a target host cell; and (d) comparing the measurement of the indicator gene from step (c) with the measurement of the indicator gene measured when steps (a)–(c) are carried out in the absence of the candidate antiretroviral drug compound;

wherein a test concentration of the candidate antiretroviral drug compound is present at steps (a)–(c); at steps (b)–(c); or at step (c).

In another embodiment of this invention, a resistance test vector comprising an HIV patient-derived segment further comprising protease having a mutation at codon 82 or codon 90 and an indicator gene, wherein the expression of the indicator gene is dependent upon the patient-derived segment.

In another embodiment of this invention, the resistance test vector is provided, wherein the patient-derived segment having a mutation at codon 82 codes for alanine (A), phenylalanine (F), serine (S), or threonine (T).

In another embodiment of this invention, the resistance test vector of is provided, wherein the patient-derived segment having a mutation at codon 82 is a substitution of alanine (A), phenylalanine (F), serine (S), or threonine (T) for valine (V).

In another embodiment of this invention, the resistance test vector is provided, wherein the patient-derived segment having a mutation at codon 90 codes for methionine (M).

In yet another embodiment of this invention, the resistance test vector is provided, wherein the patient-derived segment having a mutation at codon 90 is a substitution of methionine (M) for leucine (L).

In another embodiment of this invention, a method for determining replication capacity for a patient's virus is provided comprising:

(a) introducing a resistance test vector comprising a patient-derived segment and an indicator gene into a host cell;

(b) culturing the host cell from (a);

(c) harvesting viral particles from step (b) and infecting target host cells;

(d) measuring expression of the indicator gene in the target host cell, wherein the expression of the indicator gene is dependent upon the patient-derived segment; and (e) comparing the expression of the indicator gene from (d) with the expression of the indicator gene measured when steps (a) through (d) are carried out in a control resistance test vector.

In another embodiment of this invention, the method further comprises the step of:

(f) normalizing the expression of the indicator gene by measuring an amount of virus in step (c).

In another embodiment of this invention, the method is provided wherein the patient-derived segment comprises nucleic acid encoding HIV integrase having a mutation at codon 66.

In another embodiment of this invention, the method is provided wherein the patient-derived segment comprises nucleic acid encoding HIV integrase having a mutation at codon 154.

In another embodiment of this invention, the method is provided wherein the patient-derived segment comprises nucleic acid encoding HIV integrase having mutations at codon 66 and codon 153.

In another embodiment of this invention, the method is provided wherein the patient-derived segment comprises nucleic acid encoding HIV integrase having mutations at codon 66 and codon 154.

The structure, life cycle and genetic elements of the viruses which could be tested in the drug susceptibility and resistance test of this invention would be known to one of ordinary skill in the art. It is useful to the practice of this invention, for example, to understand the life cycle of a retrovirus, as well as the viral genes required for retrovirus rescue and infectivity. Retrovirally infected cells shed a membrane virus containing a diploid RNA genome. The virus, studded with an envelope glycoprotein (which serves to determine the host range of infectivity), attaches to a cellular receptor in the plasma membrane of the cell to be infected. After receptor binding, the virus is internalized and uncoated as it passes through the cytoplasm of the host cell. Either on its way to the nucleus or in the nucleus, the reverse transcriptase molecules resident in the viral core drive the synthesis of the double-stranded DNA provirus, a synthesis that is primed by the binding of a tRNA molecule to the genomic viral RNA. The double-stranded DNA provirus is subsequently integrated in the genome of the host cell, where it can serve as a transcriptional template for both mRNAs encoding viral proteins and virion genomic RNA, which will be packaged into viral core particles. On their way out of the infected cell, core particles move through the cytoplasm, attach to the inside of the plasma membrane of the newly infected cell, and bud, taking with them tracts of membrane containing the virally encoded envelope glycoprotein gene product. This cycle of infection—reverse transcription, transcription, translation, virion assembly, and budding—repeats itself over and over again as infection spreads.

The viral RNA and, as a result, the proviral DNA encode several cis-acting elements that are vital to the successful completion of the viral lifecycle. The virion RNA carries the viral promoter at its 3' end. Replicative acrobatics place the viral promoter at the 5' end of the proviral genome as the genome is reverse transcribed. Just 3' to the 5' retroviral LTR lies the viral packaging site. The retroviral lifecycle requires the presence of virally encoded transacting factors. The viral-RNA-dependent DNA polymerase (pol)-reverse transcriptase is also contained within the viral core and is vital to the viral life cycle in that it is responsible for the conversion of the genomic RNA to the integrative intermediate proviral DNA. The viral envelope glycoprotein, env, is required for viral attachment to the uninfected cell and for viral spread. There are also transcriptional trans-activating factors, so called transactivators, that can serve to modulate the level of transcription of the integrated parental provirus. Typically, replication-competent (non-defective) viruses are self-contained in that they encode all of these trans-acting factors. Their defective counterparts are not self-contained.

In the case of a DNA virus, such as a hepadnavirus, understanding the life cycle and viral genes required for infection is useful to the practice of this invention. The process of HBV entry has not been well defined. Replication of HBV uses an RNA intermediate template. In the infected cell the first step in replication is the conversion of the asymmetric relaxed circle DNA (rc-DNA) to covalently closed circle DNA (cccDNA). This process, which occurs within the nucleus of infected liver cells, involves completion of the DNA positive-strand synthesis and ligation of the DNA ends. In the second step, the cccDNA is transcribed by the host RNA polymerase to generate a 3.5 kB RNA template (the pregenome). This pregenome is complexed with protein in the viral core. The third step involves the synthesis of the first negative-sense DNA strand by copying the pregenomic RNA using the virally encoded P protein reverse transcriptase. The P protein also serves as the minus strand DNA primer. Finally, the synthesis of the second positive-sense DNA strand occurs by copying the first DNA strand, using the P protein DNA polymerase activity and an oligomer of viral RNA as primer. The pregenome also transcribes mRNA for the major structural core proteins.

The following flow chart illustrates certain of the various vectors and host cells which may be used in this invention. It is not intended to be all inclusive.

Vectors Indicator gene cassette + Viral vector (functional/nonfunctional
(genomic or subgenomic) indicator gene)

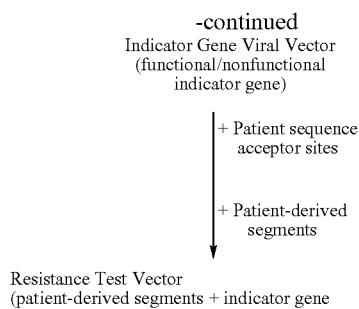

-continued
Indicator Gene Viral Vector
(functional/nonfunctional
indicator gene)

+ Patient sequence acceptor sites

+ Patient-derived segments

Resistance Test Vector
(patient-derived segments + indicator gene

Host Cells

Packaging Host Cell—transfected with packaging expression vectors

Resistance Test Vector Host Cell—a packaging host cell transfected with a resistance test vector Target Host Cell—a host cell to be infected by a resistance test vector viral particle produced by the resistance test vector host cell Resistance Test Vector "Resistance test vector" means one or more vectors which taken together contain DNA or RNA comprising a patient-derived segment and an indicator gene. In the case where the resistance test vector comprises more than one vector the patient-derived segment may be contained in one vector and the indicator gene in a different vector. Such a resistance test vector comprising more than one vector is referred to herein as a resistance test vector system for purposes of clarity but is nevertheless understood to be a resistance test vector. The DNA or RNA of a resistance test vector may thus be contained in one or more DNA or RNA molecules. In one embodiment, the resistance test vector is made by insertion of a patient-derived segment into an indicator gene viral vector. In another embodiment, the resistance test vector is made by insertion of a patient-derived segment into a packaging vector while the indicator gene is contained in a second vector, for example an indicator gene viral vector. As used herein, "patient-derived segment" refers to one or more viral segments obtained directly from a patient using various means, for example, molecular cloning or polymerase chain reaction (PCR) amplification of a population of patient-derived segments using viral DNA or complementary DNA (cDNA) prepared from viral RNA, present in the cells (e.g. peripheral blood mononuclear cells, PBMC), serum or other bodily fluids of infected patients. When a viral segment is "obtained directly" from a patient it is obtained without passage of the virus through culture, or if the virus is cultured, then by a minimum number of passages to essentially eliminate the selection of mutations in culture. The term "viral segment" refers to any functional viral sequence or viral gene encoding a gene product (e.g., a protein) that is the target of an anti-viral drug. The term "functional viral sequence" as used herein refers to any nucleic acid sequence (DNA or RNA) with functional activity such as enhancers, promoters, polyadenylation sites, sites of action of trans-acting factors, such as tar and RRE, packaging sequences, integration sequences, or splicing sequences. If a drug were to target more than one functional viral sequence or viral gene product then patient-derived segments corresponding to each said viral gene would be inserted in the resistance test vector. In the case of combination therapy where two or more anti-virals targeting two different functional viral sequences or viral gene products are being evaluated, patient-derived segments corresponding to each functional viral sequence or viral gene product would be inserted in the resistance test vector. The patient-derived segments are inserted into unique restriction sites or specified locations, called patient sequence acceptor sites, in the indicator gene viral vector or for example, a packaging vector depending on the particular construction being used as described herein.

As used herein, "patient-derived segment" encompasses segments derived from human and various animal species. Such species include, but are not limited to chimpanzees, horses, cattles, cats and dogs.

Patient-derived segments can also be incorporated into resistance test vectors using any of several alternative cloning techniques. For example, cloning via the introduction of class II restriction sites into both the plasmid backbone and the patient-derived segments or by uracil DNA glycosylase primer cloning (refs).

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that would be underrepresented in one resistance test vector alone.

Resistance test vectors are prepared by modifying an indicator gene viral vector (described below) by introducing patient sequence acceptor sites, amplifying or cloning patient-derived segments and inserting the amplified or cloned sequences precisely into indicator gene viral vectors at the patient sequence acceptor sites.

The resistance test vectors are constructed from indicator gene viral vectors which are in turn derived from genomic viral vectors or subgenomic viral vectors and an indicator gene cassette, each of which is described below. Resistance test vectors are then introduced into a host cell. Alternatively, a resistance test vector (also referred to as a resistance test vector system) is prepared by introducing patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

In one preferred embodiment, the resistance test vector may be introduced into packaging host cells together with packaging expression vectors, as defined below, to produce resistance test vector viral particles that are used in drug resistance and susceptibility tests that are referred to herein as a "particle-based test." In an alternative preferred embodiment, the resistance test vector may be introduced into a host cell in the absence of packaging expression vectors to carry out a drug resistance and susceptibility test that is referred to herein as a "non-particle-based test." As used herein a "packaging expression vector" provides the factors, such as packaging proteins (e.g. structural proteins such as core and envelope polypeptides), transacting factors, or genes required by replication-defective retrovirus or hepadnavirus. In such a situation, a replication-competent viral genome is enfeebled in a manner such that it cannot replicate on its own. This means that, although the packaging expression vector can produce the trans-acting or missing genes required to rescue a defective viral genome present in a cell containing the enfeebled genome, the enfeebled genome cannot rescue itself.

Indicator or Indicator Gene

"Indicator or indicator gene" refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the *E. coli* lacZ gene which encodes beta-galactosidase, the luc gene which encodes luciferase either from, for example, *Photonis pyralis* (the firefly) or *Renilla reniformis* (the sea pansy), the *E. coli* phoA gene which encodes alkaline phosphatase, green fluorescent protein and the bacterial CAT gene which encodes chloramphenicol acetyltransferase. Additional preferred examples of an indicator gene are secreted proteins or cell surface proteins that are readily measured by assay, such as radioimmunoassay (RIA), or fluorescent activated cell sorting (FACS), including, for example, growth factors, cytokines and cell surface antigens (e.g. growth hormone, Il-2 or CD4, respectively). "Indicator gene" is understood to also include a selection gene, also referred to as a selectable marker. Examples of suitable selectable markers for mammalian cells are dihydrofolate reductase (DHFR), thymidine kinase, hygromycin, neomycin, zeocin or *E. coli* gpt. In the case of the foregoing examples of indicator genes, the indicator gene and the patient-derived segment are discrete, i.e. distinct and separate genes. In some cases a patient-derived segment may also be used as an indicator gene. In one such embodiment in which the patient-derived segment corresponds to more than one viral gene which is the target of an anti-viral, one of said viral genes may also serve as the indicator gene. For example, a viral protease gene may serve as an indicator gene by virtue of its ability to cleave a chromogenic substrate or its ability to activate an inactive zymogen which in turn cleaves a chromogenic substrate, giving rise in each case to a color reaction. In all of the above examples of indicator genes, the indicator gene may be either "functional" or "non-functional" but in each case the expression of the indicator gene in the target cell is ultimately dependent upon the action of the patient-derived segment.

Functional Indicator Gene

In the case of a "functional indicator gene" the indicator gene may be capable of being expressed in a "packaging host cell/resistance test vector host cell" as defined below, independent of the patient-derived segment, however the functional indicator gene could not be expressed in the target host cell, as defined below, without the production of functional resistance test vector particles and their effective infection of the target host cell. In one embodiment of a functional indicator gene, the indicator gene cassette, comprising control elements and a gene encoding an indicator protein, is inserted into the indicator gene viral vector with the same or opposite transcriptional orientation as the native or foreign enhancer/promoter of the viral vector. One example of a functional indicator gene in the case of HIV or HBV, places the indicator gene and its promoter (a CMV IE enhancer/promoter) in the same or opposite transcriptional orientation as the HIV-LTR or HBV enhancer-promoter, respectively, or the CMV IE enhancer/promoter associated with the viral vector.

Non-Functional Indicator Gene

Alternatively the indicator gene, may be "non-functional" in that the indicator gene is not efficiently expressed in a packaging host cell transfected with the resistance test vector, which is then referred to a resistance test vector host cell, until it is converted into a functional indicator gene through the action of one or more of the patient-derived segment products. An indicator gene is rendered non-functional through genetic manipulation according to this invention.

1. Permuted Promoter In one embodiment an indicator gene is rendered non-functional due to the location of the promoter, in that, although the promoter is in the same transcriptional orientation as the indicator gene, it follows rather than precedes the indicator gene coding sequence. This misplaced promoter is referred to as a "permuted promoter." In addition to the permuted promoter the orientation of the non-functional indicator gene is opposite to that of the native or foreign promoter/enhancer of the viral vector. Thus the coding sequence of the non-functional indicator gene can neither be transcribed by the permuted promoter nor by the viral promoters. The non-functional indicator gene and its permuted promoter is rendered functional by the action of one or more of the viral proteins. One example of a non-functional indicator gene with a permuted promoter in the case of HIV, places a T7 phage RNA polymerase promoter (herein referred to as T7 promoter) promoter in the 5' LTR in the same transcriptional orientation as the indicator gene. The indicator gene cannot be transcribed by the T7 promoter as the indicator gene cassette is positioned upstream of the T7 promoter. The non-functional indicator gene in the resistance test vector is converted into a functional indicator gene by reverse transcriptase upon infection of the target cells, resulting from the repositioning of the T7 promoter, by copying from the 5' LTR to the 3' LTR, relative to the indicator gene coding region. Following the integration of the repaired indicator gene into the target cell chromosome by HIV integrase, a nuclear T7 RNA polymerase expressed by the target cell transcribes the indicator gene. One example of a non-functional indicator gene with a permuted promoter in the case of HBV, places an enhancer-promoter region downstream or 3' of the indicator gene both having the same transcriptional orientation. The indicator gene cannot be transcribed by the enhancer-promoter as the indicator gene cassette is positioned upstream. The non-functional indicator gene in the resistance test vector is converted into a functional indicator gene by reverse transcription and circularization of the HBV indicator gene viral vector by the repositioning of the enhancer-promoter upstream relative to the indicator gene coding region.

A permuted promoter may be any eukaryotic or prokaryotic promoter which can be transcribed in the target host cell. Preferably the promoter will be small in size to enable insertion in the viral genome without disturbing viral replication. More preferably, a promoter that is small in size and is capable of transcription by a single subunit RNA polymerase introduced into the target host cell, such as a bacteriophage promoter, will be used. Examples of such bacteriophage promoters and their cognate RNA polymerases include those of phages T7, T3 and Sp6. A nuclear localization sequence (NLS) may be attached to the RNA polymerase to localize expression of the RNA polymerase to the nucleus where they may be needed to transcribed the repaired indicator gene. Such an NLS may be obtained from any nuclear-transported protein such as the SV40 T antigen. If a phage RNA polymerase is employed, an internal ribosome entry site (IRES) such as the EMC virus 5' untranslated region (UTR) may be added in front of the indicator gene, for translation of the transcripts which are generally uncapped. In the case of HIV, the permuted promoter itself can be introduced at any position within the 5' LTR that is copied to the 3' LTR during reverse transcription so long as LTR function is not disrupted, preferably within the U5 and R portions of the LTR, and most preferably outside of functionally important and highly conserved regions of U5 and R. In the case of HBV, the permuted promoter can be placed at any position that does not disrupt the cis acting elements that are necessary for HBV DNA replication. Blocking sequences may be added at the ends of the resistance test vector should there be inappropriate expression of the non-functional indicator gene due to transfection artifacts (DNA concatenation). In the HIV example of the permuted T7 promoter given above, such a blocking sequence may consist of a T7 transcriptional terminator, positioned to block readthrough transcription resulting from DNA concatenation, but not transcription resulting from repositioning of the permuted T7 promoter from the 5' LTR to the 3' LTR during reverse transcription.

2. Permuted Coding Region In a second embodiment, an indicator gene is rendered non-functional due to the relative location of the 5' and 3' coding regions of the indicator gene, in that, the 31 coding region precedes rather than follows the 5' coding region. This misplaced coding region is referred to as a "permuted coding region." The orientation of the non-functional indicator gene may be the same or opposite to that of the native or foreign promoter/enhancer of the viral vector, as mRNA coding for a functional indicator gene will be produced in the event of either orientation. The non-functional indicator gene and its permuted coding region is rendered functional by the action of one or more of the patient-derived segment products. A second example of a non-functional indicator gene with a permuted coding region in the case of HIV, places a 5' indicator gene coding region with an associated promoter in the 3' LTR U3 region and a 3' indicator gene coding region in an upstream location of the HIV genome, with each coding region having the same transcriptional orientation as the viral LTRs. In both examples, the 5' and 3' coding regions may also have associated splice donor and acceptor sequences, respectively, which may be heterologous or artificial splicing signals. The indicator gene cannot be functionally transcribed either by the associated promoter or viral promoters, as the permuted coding region prevents the formation of functionally spliced transcripts. The non-functional indicator gene in the resistance test vector is converted into a functional indicator gene by reverse transcriptase upon infection of the target cells, resulting from the repositioning of the 5' and 3' indicator gene coding regions relative to one another, by copying of the 3' LTR to the 5' LTR. Following transcription by the promoter associated with the 5' coding region, RNA splicing can join the 5' and 3' coding regions to produce a functional indicator gene product. One example of a non-functional indicator gene with a permuted coding region in the case of HBV, places a 3' indicator gene coding region upstream or 5' of the enhancer-promoter and the 5' coding region of the indicator gene. The transcriptional orientation of the indicator gene 5' and 3' coding regions are identical to one another, and the same as that of the indicator gene viral vector. However, as the indicator gene 5' and 3' coding regions are permuted in the resistance test vectors (i.e., the 5' coding region is downstream of the 3' coding region), no mRNA is transcribed which can be spliced to generate a functional indicator gene coding region. Following reverse transcription and circularization of the indicator gene viral vector, the indicator gene 3' coding region is positioned downstream or 3' to the enhancer-promoter and 5' coding regions thus permitting the transcription of mRNA which can be spliced to generate a functional indicator gene coding region.

3. Inverted Intron In a third embodiment, the indicator gene is rendered non-functional through use of an "inverted intron," i.e. an intron inserted into the coding sequence of the indicator gene with a transcriptional orientation opposite to that of the indicator gene. The overall transcriptional orientation of the indicator gene cassette including its own, linked promoter, is opposite to that of the viral control elements, while the orientation of the artificial intron is the same as the viral control elements. Transcription of the indicator gene by its own linked promoter does not lead to the production of functional transcripts as the inverted intron cannot be spliced in this orientation. Transcription of the indicator gene by the viral control elements does, however, lead to the removal of the inverted intron by RNA splicing, although the indicator gene is still not functionally expressed as the resulting transcript has an antisense orientation. Following the reverse transcription of this transcript and integration of the resultant retroviral DNA, or the circularization of hepadnavirus DNA, the indicator gene can be functionally transcribed using its own linked promoter as the inverted intron has been previously removed. In this case, the indicator gene itself may contain its own functional promoter with the entire transcriptional unit oriented opposite to the viral control elements. Thus the non-functional indicator gene is in the wrong orientation to be transcribed by the viral control elements and it cannot be functionally transcribed by its own promoter, as the inverted intron cannot be properly excised by splicing. However, in the case of a retrovirus and HIV specifically and hepadnaviruses, and HBV specifically, transcription by the viral promoters (HIV LTR or HBV enhancer-promoter) results in the removal of the inverted intron by splicing. As a consequence of reverse transcription of the resulting spliced transcript and the integration of the resulting provirus into the host cell chromosome or circularization of the HBV vector, the indicator gene can now be functionally transcribed by its own promoter. The inverted intron, consisting of a splice donor and acceptor site to remove the intron, is preferably located in the coding region of the indicator gene in order to disrupt translation of the indicator gene. The splice donor and acceptor may be any splice donor and acceptor. A preferred splice donor-receptor is the CMV IE splice donor and the splice acceptor of the second exon of the human alpha globin gene ("intron A").

Indicator Gene Viral Vector—Construction

As used herein, "indicator gene viral vector" refers to a vector(s) comprising an indicator gene and its control elements and one or more viral genes. The indicator gene viral vector is assembled from an indicator gene cassette and a "viral vector," defined below. The indicator gene viral vector may additionally include an enhancer, splicing signals, polyadenylation sequences, transcriptional terminators, or other regulatory sequences. Additionally the indicator gene viral vector may be functional or nonfunctional. In the event that the viral segments which are the target of the anti-viral drug are not included in the indicator gene viral vector they are provided in a second vector. An "indicator gene cassette" comprises an indicator gene and control elements. "Viral vector" refers to a vector comprising some or all of the following: viral genes encoding a gene product, control sequences, viral packaging sequences, and in the case of a retrovirus, integration sequences. The viral vector may additionally include one or more viral segments one or more of which may be the target of an anti-viral drug. Two examples of a viral vector which contain viral genes are referred to herein as an "genomic viral vector" and a "subgenomic viral vector." A "genomic viral vector" is a vector which may comprise a deletion of a one or more viral genes to render the virus replication incompetent, but which otherwise preserves the mRNA expression and processing characteristics of the complete virus. In one embodiment for an HIV drug susceptibility and resistance test, the genomic viral vector comprises the HIV gag-pol, vif, vpr, tat, rev, vpu, and nef genes (some, most or all of env may be deleted). A "subgenomic viral vector" refers to a vector comprising the coding region of one or more viral genes which may encode the proteins that are the target(s) of the anti-viral drug. In the case of HIV, a preferred embodiment is a subgenomic viral vector comprising the HIV gag-pol gene. In the case of HBV a preferred embodiment is a subgenomic viral vector comprising the HBV P gene. In the case of HIV, two examples of proviral clones used for viral vector construction are: HXB2 (Fisher et al., (1986) *Nature*, 320, 367–371) and NL4-3, (Adachi et al., (1986) *J. Virol.*, 59, 284–291). In the case of HBV, a large number of full length genomic sequences have been characterized and could be used for construction of HBV viral vectors: GenBank Nos. M54923, M38636, J02203 and X59795. The viral coding genes may be under the control of a native enhancer/promoter or a foreign viral or cellular enhancer/promoter. A preferred embodiment for an HIV drug susceptibility and resistance test, is to place the genomic or subgenomic viral coding regions under the control of the native enhancer/promoter of the HIV-LTR U3 region or the CMV immediate-early (IE) enhancer/promoter. A preferred embodiment for an HBV drug susceptibility and resistance test, is to place the genomic or subgenomic viral coding regions under the control of the CMV immediate-early (IE) enhancer/promoter. In the case of an indicator gene viral vector that contains one or more viral genes which are the targets or encode proteins which are the targets of an anti-viral drug(s) then said vector contains the patient sequence acceptor sites. The patient-derived segments are inserted in the patient sequence acceptor site in the indicator gene viral vector which is then referred to as the resistance test vector, as described above.

"Patient sequence acceptor sites" are sites in a vector for insertion of patient-derived segments and said sites may be: 1) unique restriction sites introduced by site-directed mutagenesis into a vector; 2) naturally occurring unique restriction sites in the vector; or 3) selected sites into which a patient-derived segment may be inserted using alternative cloning methods (e.g. UDG cloning). In one embodiment the patient sequence acceptor site is introduced into the indicator gene viral vector. The patient sequence acceptor sites are preferably located within or near the coding region of the viral protein which is the target of the anti-viral drug. The viral sequences used for the introduction of patient sequence acceptor sites are preferably chosen so that no change, or a conservative change, is made in the amino acid coding sequence found at that position. Preferably the patient sequence acceptor sites are located within a relatively conserved region of the viral genome to facilitate introduction of the patient-derived segments. Alternatively, the patient sequence acceptor sites are located between functionally important genes or regulatory sequences. Patient-sequence acceptor sites may be located at or near regions in the viral genome that are relatively conserved to permit priming by the primer used to introduce the corresponding restriction site into the patient-derived segment. To improve the representation of patient-derived segments further, such primers may be designed as degenerate pools to accommodate viral sequence heterogeneity, or may incorporate residues such as deoxyinosine (I) which have multiple base-pairing capabilities. Sets of resistance test vectors having patient sequence acceptor sites that define the same or overlapping restriction site intervals may be used together in the drug resistance and susceptibility tests to provide representation of patient-derived segments that contain internal restriction sites identical to a given patient sequence acceptor site, and would thus be underrepresented in either resistance test vector alone.

Host Cells

The resistance test vector is introduced into a host cell. Suitable host cells are mammalian cells. Preferred host cells are derived from human tissues and cells which are the principle targets of viral infection. In the case of HIV these include human cells such as human T cells, monocytes, macrophage, dendritic cells, Langerhans cells, hematopoeitic stem cells or precursor cells, and other cells. In the case of HBV, suitable host cells include hepatoma cell lines (HepG2, Huh 7), primary human hepatocytes, mammalian cells which can be-infected by pseudotyped HBV, and other cells. Human derived host cells will assure that the anti-viral drug will enter the cell efficiently and be converted by the cellular enzymatic machinery into the metabolically relevant form of the anti-viral inhibitor. Host cells are referred to herein as a "packaging host cells," "resistance test vector host cells," or "target host cells." A "packaging host cell" refers to a host cell that provides the trans-acting factors and viral packaging proteins required by the replication defective viral vectors used herein, such as the resistance test vectors, to produce resistance test vector viral particles. The packaging proteins may be provided for by the expression of viral genes contained within the resistance test vector itself, a packaging expression vector(s), or both. A packaging host cell is a host cell which is transfected with one or more packaging expression vectors and when transfected with a resistance test vector is then referred to herein as a "resistance test vector host cell" and is sometimes referred to as a packaging host cell/resistance test vector host cell. Preferred host cells for use as packaging host cells for HIV include 293 human embryonic kidney cells (293, Graham, F. L. et al., J. Gen Virol. 36: 59, 1977), BOSC23 (Pear et al., *Proc. Natl. Acad. Sci.* 90, 8392, 1993), tsa54 and tsa201 cell lines (Heinzel et al., *J. Virol.* 62, 3738, 1988), for HBV HepG2 (Galle and Theilmann, L. Arzheim.-Forschy *Drug Res.* (1990) 40, 1380–1382). (Huh, Ueda, K et al. *Virology* *1989) 169, 213–216). A "target host cell" refers to a cell to be infected by resistance test vector viral particles produced by the resistance test vector host cell in which expression or inhibition of the indicator gene takes place. Preferred host cells for use as target host cells include human T cell leukemia cell lines including Jurkat (ATCC T1B–152), H9 (ATCC HTB-176), CEM (ATCC CCL-119), HUT78 (ATCC T1B–161), and derivatives thereof.

This invention is illustrated in the Experimental Detais section which follows. These sections are set forth to aid in an understanding of the invention but are not intended to, and should not be construed to, limit in any way the invention as set forth in the claims which follow thereafter.

Experimental Details

General Materials and Methods

Most of the techniques used to construct vectors, and transfect and infect cells, are widely practiced in the art, and most practitioners are familiar with the standard resource materials that describe specific conditions and procedures. However, for convenience, the following paragraphs may serve as a guideline.

As used herein, "replication capacity" is defined herein is a measure of how well the virus replicates. This may also be referred to as viral fitness. In one embodiment, replication capacity can be measured by evaluating the ability of the virus to replicate in a single round of replication.

As used herein, "control resistance test vector" is defined as a resistance test vector comprising a standard viral sequence (for example, HXB2, PNL4-3) and an indicator gene.

As used herein, "normalizing" is defined as standardizing the amount of the expression of indicator gene measured relative to the number of viral particles giving rise to the expression of the indicator gene. For example, normalization is measured by dividing the amount of luciferase activity measured by the number of viral particles measured at the time of infection.

"Plasmids" and "vectors" are designated by a lower case p followed by letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

Construction of the vectors of the invention employs standard ligation and restriction techniques which are well understood in the art (see Ausubel et al., (1987) Current Protocols in Molecular Biology, Wiley—Interscience or Maniatis et al., (1992) in Molecular Cloning: A laboratory Manual, Cold Spring Harbor Laboratory, N.Y.). Isolated plasmids, DNA sequences, or synthesized oligonucleotides are cleaved, tailored, and religated in the form desired. The sequences of all DNA constructs incorporating synthetic DNA were confirmed by DNA sequence analysis (Sanger et al. (1977) Proc. Natl. Acad. Sci. 74, 5463–5467).

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements are known to the ordinarily skilled artisan. For analytical purposes, typically 1 µg of plasmid or DNA fragment is used with about 2 units of enzyme in about 20 µl of buffer solution. Alternatively, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499–560 (1980).

Restriction cleaved fragments may be blunt ended by treating with the large fragment of E. coli DNA polymerase I (Klenow) in the presence of the four deoxynucleotide triphosphates (dNTPs) using incubation times of about 15 to 25 minutes at 20° C. in 50 mM Tris (pH 7.6) 50 mM NaCl, 6 mM $MgCl_2$, 6 mM DTT and 5–10 mM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 µl volumes under the following standard conditions and temperatures: 20 mM Tris-Cl pH 7.5, 10 mM $MgCl_2$, 10 mM DTT, 33 mg/ml BSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 mM total end concentration). Intermolecular blunt end ligations (usually employing a 10–30 fold molar excess of linkers) are performed at 1 µM total ends concentration.

"Transient expression" refers to unamplified expression within about one day to two weeks of transfection. The optimal time for transient expression of a particular desired heterologous gene may vary depending on several factors including, for example, any transacting factors which may be employed, translational control mechanisms and the host cell. Transient expression occurs when the particular plasmid that has been transfected functions, i.e., is transcribed and translated. During this time the plasmid DNA which has entered the cell is transferred to the nucleus. The DNA is in a nonintegrated state, free within the nucleus. Transcription of the plasmid taken up by the cell occurs during this period. Following transfection the plasmid DNA may become degraded or diluted by cell division. Random integration within the cell chromatin occurs.

In general, vectors containing promoters and control sequences which are derived from species compatible with the host cell are used with the particular host cell. Promoters suitable for use with prokaryotic hosts illustratively include the beta-lactamase and lactose promoter systems, alkaline phosphatase, the tryptophan (trp) promoter system and hybrid promoters such as tac promoter. However, other functional bacterial promoters are suitable. In addition to prokaryotes, eukaryotic microbes such as yeast cultures may also be used. Saccharomyces cerevisiae, or common baker's yeast is the most commonly used eukaryotic microorganism, although a number of other strains are commonly available. Promoters controlling transcription from vectors in mammalian host cells may be obtained from various sources, for example, the genomes of viruses such as: polyoma, simian virus 40 (SV40), adenovirus, retroviruses, hepatitis B virus and preferably cytomegalovirus, or from heterologous mammalian promoters, e.g. β-actin promoter. The early and late promoters of the SV 40 virus are conveniently obtained as an SV40 restriction fragment that also contains the SV40 viral origin of replication. The immediate early promoter of the human cytomegalovirus is conveniently obtained as a HindIII E restriction fragment. Of course, promoters from the host cell or related species also are useful herein.

The vectors used herein may contain a selection gene, also termed a selectable marker. A selection gene encodes a protein, necessary for the survival or growth of a host cell transformed with the vector. Examples of suitable selectable markers for mammalian cells include the dihydrofolate reductase gene (DHFR), the ornithine decarboxylase gene, the multi-drug resistance gene (mdr), the adenosine deaminase gene, and the glutamine synthase gene. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is referred to as dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern and Berg (1982) J. Molec. Appl. Genet. 1, 327), mycophenolic acid (Mulligan and Berg (1980) Science 209, 1422), or hygromycin (Sugden et al. (1985) Mol. Cell. Biol. 5, 410–413). The three examples given above employ bacterial genes under eukaryotic control to convey resistance to the appropriate drug neomycin (G418 or genticin), xgpt (mycophenolic acid) or hygromycin, respectively.

"Transfection" means introducing DNA into a host cell so that the DNA is expressed, whether functionally expressed or otherwise; the DNA may also replicate either as an extrachromosomal element or by chromosomal integration. Unless otherwise provided, the method used herein for transfection of the host cells is the calcium phosphate co-precipitation method of Graham and van der Eb (1973) Virology 52, 456–457. Alternative methods for transfection are electroporation, the DEAE-dextran method, lipofection and biolistics (Kriegler (1990) Gene Transfer and Expression: A Laboratory Manual, Stockton Press).

Host cells may be transfected with the expression vectors of the present invention and cultured in conventional nutrient media modified as is appropriate for inducing promoters, selecting transformants or amplifying genes. Host cells are cultured in F12:DMEM (Gibco) 50:50 with added glutamine. The culture conditions, such as temperature, pH and the like, are those previously used with the host cell selected for expression, and will be apparent to the ordinarily skilled artisan.

The following examples merely illustrate the best mode now known for practicing the invention, but should not be construed to limit the invention. All publications and patent applications cited in this specification are herein incorporated by reference in their entirety as if each individual publication or patent application were specifically and individually indicated to be incorporated by reference.

EXAMPLE 1

Phenotypic Drug Susceptibility and Resistance Test Using Resistance Test Vectors Phenotypic drug susceptibility and resistance tests are carried out using the means and methods described in U.S. Pat. No. 5,837,464 (International Publication Number WO 97/27319) which is hereby incorporated by reference.

In these experiments patient-derived segment(s) corresponding to the HIV protease and reverse transcriptase coding regions were either patient-derived segments amplified by the reverse transcription-polymerase chain reaction method (RT-PCR) using viral RNA isolated from viral particles present in the serum of HIV-infected individuals or were mutants of wild type HIV-1 made by site directed mutagenesis of a parental clone of resistance test vector DNA. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into cDNA. The cDNA was then amplified using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216–2220) [e.g. Expand High Fidelity PCR System (Taq+ Pwo), (Boehringer Mannheim. Indianapolis, Ind.) OR GeneAmp XL PCR kit (Tth+Vent), (Roche Molecular Systems, Inc., Branchburg, N.J.)].

PCR6 (Table 5, #1) is used for reverse transcription of viral RNA into cDNA. The primers, ApaI primer (PDSApa, Table 5, #2) and AgeI primer (PDSAge, Table 5, #3) used to amplify the "test" patient-derived segments contained sequences resulting in ApaI and AgeI recognition sites being introduced into both ends of the PCR product, respectively.

Figure 1:
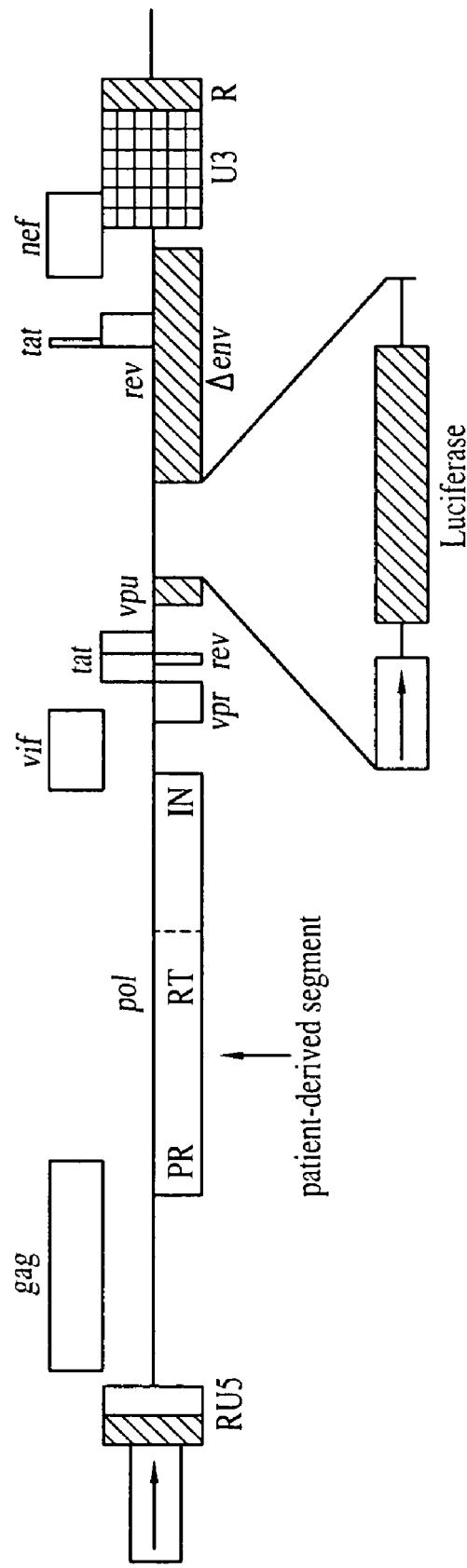
FIG. 1

Resistance test vectors incorporating the "test" patient-derived segments were constructed as described in U.S. Pat. No. 5,837,464 (International Publication Number WO 97/27319) (see FIG. 1) using an amplified DNA product of 1.5 kB prepared by RT-PCR using viral RNA as a template and oligonucleotides PCR6 (#1), PDSApa (#2) and PDSAge (#3) as primers, followed by digestion with ApaI and AgeI or the isoschizomer PinA1. To ensure that the plasmid DNA corresponding to the resultant resistance test vector comprises a representative sample of the HIV viral quasi-species present in the serum of a given patient, many (>100) independent *E. coli* transformants obtained in the construction of a given resistance test vector were pooled and used for the preparation of plasmid DNA.

A packaging expression vector encoding an amphotrophic MuLV 4070A env gene product enables production in a resistance test vector host cell of resistance test vector viral particles which can efficiently infect human target cells. Resistance test vectors encoding all HIV genes with the exception of env were used to transfect a packaging host cell (once transfected the host cell is referred to as a resistance test vector host cell). The packaging expression vector which encodes the amphotrophic MuLV 4070A env gene product is used with the resistance test vector to enable production in the resistance test vector host cell of infectious pseudotyped resistance test vector viral particles.

Resistance tests performed with resistance test vectors were carried out using packaging host and target host cells consisting of the human embryonic kidney cell line 293 (Cell Culture Facility, UC San Francisco, SF, Calif.) or the Jurkat leukemic T-cell line (Arthur Weiss, UC San Francisco, SF, Calif.).

Figure 2:
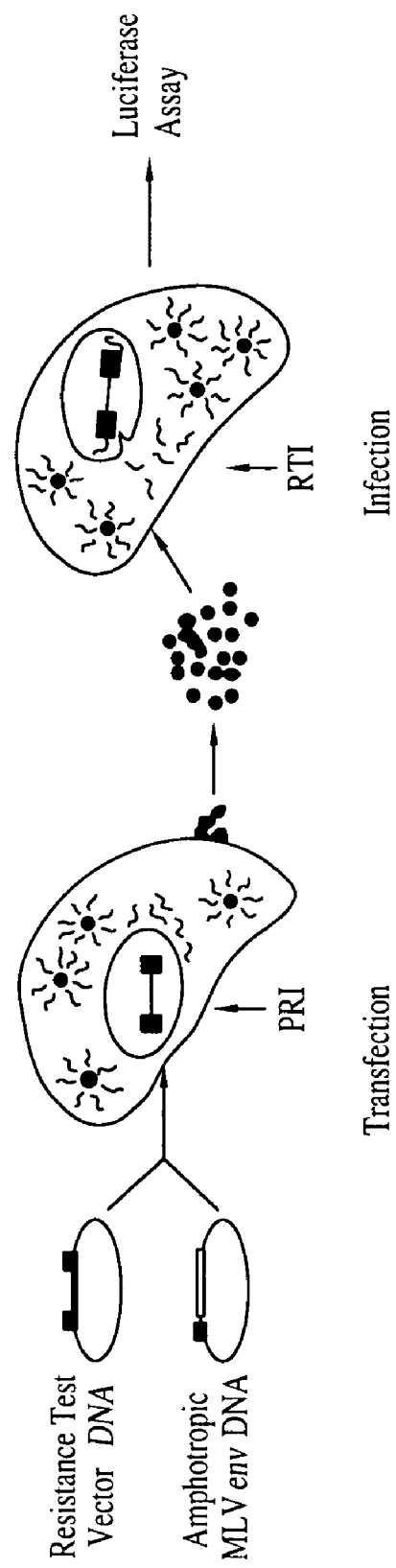

Resistance tests were carried out with resistance test vectors using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured (see FIG. 2).

The resistance test vectors containing a functional luciferase gene cassette were constructed and host cells were transfected with the resistance test vector DNA. The resistant test vectors contained patient-derived reverse transcriptase and protease DNA sequences that encode proteins which were either susceptible or resistant to the antiretroviral agents, such as nucleoside reverse transcriptase inhibitors, non-nucleoside reverse transcriptase inhibitors and protease inhibitors. The resistance test vector viral particles produced by transfecting the resistance test vector DNA into host cells, either in the presence or absence of protease inhibitors, were used to infect target host cells grown either in the absence of NRTI or NNRTI or in the presence of increasing concentrations of the drug. Luciferase activity in infected target host cells in the presence of drug was compared to the luciferase activity in infected target host cells in the absence of drug. Drug resistance was measured as the concentration of drug required to inhibit by 50% the luciferase activity detected in the absence of drug (inhibitory concentration 50%, IC50). The IC50 values were determined by plotting percent drug inhibition vs. $\log_{10}$ drug concentration.

Host cells were seeded in 10-cm-diameter dishes and were transfected one day after plating with resistance test vector plasmid DNA and the envelope expression vector. Transfections were performed using a calcium-phosphate co-precipitation procedure. The cell culture media containing the DNA precipitate was replaced with fresh medium, from one to 24 hours, after transfection. Cell culture media containing resistance test vector viral particles was harvested one to four days after transfection and was passed through a 0.45-mm filter before being stored at −80° C. HIV capsid protein (p24) levels in the harvested cell culture media were determined by an EIA method as described by the manufacturer (SIAC; Frederick, Md.). Before infection, target cells (293 and 293/T) were plated in cell culture media. Control infections were performed using cell culture media from mock transfections (no DNA) or transfections containing the resistance test vector plasmid DNA without the envelope expression plasmid. One to three or more days after infection the media was removed and cell lysis buffer (Promega) was added to each well. Cell lysates were assayed for luciferase activity. The inhibitory effect of the drug was determined using the following equation:

$$\% \text{ luciferase inhibition} = [1 - (\text{RLUluc[drug]RLUluc})] \times 100$$

where RLUluc [drug] is the relative light unit of luciferase activity in infected cells in the presence of drug and RLUluc is the Relative Light Unit of luciferase activity in infected cells in the absence of drug. IC50 values were obtained from the sigmoidal curves that were generated from the data by plotting the percent inhibition of luciferase activity vs. the $\log_{10}$ drug concentration. Examples of drug inhibition curves are shown in (FIG. 3).

EXAMPLE 2

An In Vitro Assay Using Resistance Test Vectors and Site Directed Mutants to Correlate Phenotypes and Genotypes Associated with HIV Drug Susceptibility and Resistance Phenotypic susceptibility analysis of patient HIV samples Resistance test vectors are constructed as described in example 1. Resistance test vectors, or clones derived from the resistance test vector pools, are tested in a phenotypic assay to determine accurately and quantitatively the level of susceptibility to a panel of anti-retroviral drugs. This panel of anti-retroviral drugs may comprise members of the classes known as nucleoside-analog reverse transcriptase inhibitors (NRTIs), non-nucleoside reverse transcriptase inhibitors (NNRTIs), and protease inhibitors (PRIs). The panel of drugs can be expanded as new drugs or new drug targets become available. An IC50 is determined for each resistance test vector pool for each drug tested. The pattern of susceptibility to all of the drugs tested is examined and compared to known patterns of susceptibility.

A patient sample can be further examined for genotypic changes correlated with the pattern of susceptibility observed.

Genotypic Analysis of Patient HIV Samples

Resistance test vector DNAs, either pools or clones, are analyzed by any of the genotyping methods described in Example 1. In one embodiment of the invention, patient HIV sample sequences are determined using viral RNA purification, RT/PCR and ABI chain terminator automated sequencing. The sequence that is determined is compared to control sequences present in the database or is compared to a sample from the patient prior to initiation of therapy, if available. The genotype is examined for sequences that are different from the control or pre-treatment sequence and correlated to the observed phenotype.

Phenotypic Susceptibility Analysis of Site Directed Mutants

Genotypic changes that are observed to correlate with changes in phenotypic patterns of drug susceptibility are evaluated by construction of resistance test vectors containing the specific mutation on a defined, wild-type (drug susceptible) genetic background. Mutations may be incorporated alone and/or in combination with other mutations that are thought to modulate the susceptibility of HIV to a certain drug or class of drugs. Mutations are introduced into the resistance test vector through any of the widely known methods for site-directed mutagenesis. In one embodiment of this invention the mega-primer PCR method for site-directed mutagenesis is used. A resistance test vector containing the specific mutation or group of mutations are then tested using the phenotypic susceptibility assay described above and the susceptibility profile is compared to that of a genetically defined wild-type (drug susceptible) resistance test vector which lacks the specific mutations. Observed changes in the pattern of phenotypic susceptibility to the antiretroviral drugs tested are attributed to the specific mutations introduced into the resistance test vector.

EXAMPLE 3

Using Resistance Test Vectors to Correlate Genotypes and Phenotypes Associated with Changes in PRI Drug Susceptibility in HIV.

Phenotypic Analysis of Patient 0732

A resistance test vector was constructed as described in example 1 from a patient sample designated as 0732. This patient had been previously treated with nelfinavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-0732. RTV-0732 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-0732 in which there was a decrease in both nelfinavir and indinavir susceptibility (increased resistance) and an increase in amprenavir susceptibility (see FIG. 4 and Table 1). Patient sample 0732 was examined further for genotypic changes associated with the pattern of susceptibility.

Determination of Genotype of Patient 0732

RTV-0732 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions K14R, I15V, K20T, E35D, M36I, R41K, I62V, L63Q and N88S. K14R, I15V, E35D, R41K and I62V are naturally occurring polymorphisms in HIV-1 PR and are not associated with reduced susceptibility to any drug. M36I has previously been described to be associated with resistance to ritonavir and nelfinavir (Shihazi, 1998). N88S has previously been described to be associated with resistance to nelfinavir (Patick A A C, 42: 2637 (1998) and an investigational PRI, SC55389A (Smidt, 1997).

Phenotypic Analysis of Patient 627

A resistance test vector was constructed as described in example 1 from a patient sample designated as 627. This patient had been treated with indinavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-627. RTV-627 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-627 in which there was a decrease in indinavir and nelfinavir susceptibility (increased resistance) and an increase in amprenavir and saquinavir susceptibility. Patient sample 627 was examined further for genotypic changes associated with the pattern of susceptibility.

Determination of Genotype of Patient 627

RTV-627 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions 13I/V, E35D, M46L, L63P, I64V, I73V and N88S. I13V, E35D and I64V are naturally occurring polymorphisms in HIV-1 PR and are not associated with reduced susceptibility to any drug. M46L has previously been described to be associated with resistance to indinavir and amprenavir. L63P has previously been described to be associated with resistance to indinavir and nelfinavir. N88S has previously been described to be associated with resistance to nelfinavir (Patick, 1998) and an investigational PRI, SC55389A (Smidt, 1997).

Phenotypic Analysis of Patient 1208

A resistance test vector was constructed as described in example 1 from a patient sample designated as 1208. This patient had been previously treated with nelfinavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-1208. RTV-1208 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-1208 in which there was a decrease in indinavir and nelfinavir susceptibility (increased resistance) and an increase in amprenavir susceptibility. Patient sample 1208 was examined further for genotypic changes associated with the pattern of susceptibility.

Determination of Genotype of Patient 1208

RTV-1208 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions I62V, L63P, V77I, and N88S. I62V is a naturally occurring polymorphism in HIV-1 PR and is not associated with reduced susceptibility to any drug. L63P has previously been described to be associated with resistance to indinavir and nelfinavir. V77I has previously been described to be associated with resistance to nelfinavir. N88S has previously been described to be associated with resistance to nelfinavir (Patick, 1998) and an investigational PRI, SC55389A (Smidt, 1997).

Phenotypic Analysis of Patient 360

A resistance test vector was constructed as described in example 1 from a patient sample designated as 360. This patient had been previously treated with indinavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-360. RTV-360 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-360 in which there was a decrease in indinavir and nelfinavir susceptibility (increased resistance) and an increase in amprenavir susceptibility. Patient sample 360 was examined further for genotypic changes associated with the pattern of susceptibility.

Determination of Genotype of Patient 360

RTV-360 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions I13V, K20M, M36V, N37A, M46I, I62V, L63P, N88S, and I93L. I13V, N37A and I62V are naturally occurring polymorphisms in HIV-1 PR and are not associated with reduced susceptibility to any drug. K20M has previously been described to be associated with resistance to indinavir. M46I has previously been described to be associated with resistance to indinavir, ritonavir, nelfinavir and amprenavir. L63P has previously been described to be associated with resistance to indinavir and nelfinavir. N88S has previously been described to be associated with resistance to nelfinavir (Patick, 1998) and an investigational PRI, SC55389A (Smidt, 1997).

Phenotypic Analysis of Patient 0910

A resistance test vector was constructed as described in example 1 from a patient sample designated as 0910. This patient had been previously treated with nelfinavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-0910. RTV-0910 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-0910 in which there was a decrease in indinavir and nelfinavir susceptibility (increased resistance) and an increase in amprenavir susceptibility. Patient sample 0910 was examined further for genotypic changes associated with the pattern of susceptibility.

Determination of Genotype of Patient 0910

RTV-0910 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions M46I, L63P, V77I, N88S and I93I/L. I13V, K14R, N37D and I193L are naturally occuring polymorphism in HIV-1 PR and is not associated with reduced susceptibility to any drug. V77I has previously been described to be associated with resistance to nelfinavir. M46I has previously been described to be associated with resistance to indinavir, ritonavir, nelfinavir and amprenavir. L63P has previously been described to be associated with resistance to indinavir and nelfinavir. N88S has previously been described to be associated with resistance to nelfinavir (Patick, 1998) and an investigational PRI, SC55389A (Smidt, 1997).

Phenotypic Analysis of Patient 3542

A resistance test vector was constructed as described in example 1 from a patient sample designated as 3542. This patient had been treated with indinavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-3542. RTV-3542 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-3542 in which there was a decrease in indinavir, nelfinavir and ritonavir susceptibility (increased resistance) and an increase in amprenavir susceptibility. Patient sample 3542 was examined further for genotypic changes associated with the pattern of susceptibility.

Determination of Genotype of Patient 3542

RTV-3542 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions I13V, K14R, N37D, M46I, L63P, N88S and I93L. K14R and N37A/D are naturally occurring polymorphisms in HIV-1 PR and are not associated with reduced susceptibility to any drug. M46I has previously been described to be associated with resistance to indinavir, ritonavir, nelfinavir and amprenavir. L63P has previously been described to be associated with resistance to indinavir and nelfinavir. N88S has previously been described to be associated with resistance to nelfinavir (Patick, 1998) and an investigational PRI, SC55389A (Smidt, 1997).

Phenotypic Analysis of Patient 3654

A resistance test vector was constructed as described in example 1 from a patient sample designated as 3654. This patient had been previously treated with ritonavir. Isolation of viral RNA and RT/PCR was used to generate a patient derived segment that comprised viral sequences coding for all of PR and aa 1–313 of RT. The patient derived segment was inserted into an indicator gene viral vector to generate a resistance test vector designated RTV-3654. RTV-3654 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine, nevirapine and efavirenz), and PRIs (indinavir, nelfinavir, ritonavir, saquinavir and amprenavir). An IC50 was determined for each drug tested. Susceptibility of the patient virus to each drug was examined and compared to known patterns of susceptibility. A pattern of susceptibility to the PRIs was observed for patient sample RTV-3654 in which there was a decrease in indinavir and nelfinavir susceptibility (increased resistance) and an increase in amprenavir susceptibility. Patient sample 3654 was examined further for genotypic changes associated with the pattern of susceptibility.

Determination of Genotype of Patient 3654

RTV-3654 DNA was analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. PR mutations were noted at positions I13V, R41K, M46I, L63P, V77I, N88S and I93L. I13V, R41K and I93L are naturally occurring polymorphism in HIV-1 PR and is not associated with reduced susceptibility to any drug. M46I has previously been described to be associated with resistance to indinavir, ritonavir, nelfinavir and amprenavir. L63P has previously been described to be associated with resistance to indinavir and nelfinavir. V77I has previously been described to be associated with resistance to nelfinavir. N88S has previously been described to be associated with resistance to an investigational PRI, SC55389A (Smidt, 1997).

EXAMPLE 4

Using Site Directed Mutants to Correlate Genotypes and Phenotypes Associated with Changes in PRI Drug Susceptibility in HIV Site Directed Mutagenesis Resistance test vectors were constructed containing the N88S mutation alone and in combination with other substitutions in PR (L63P, V77I and M46L) known to modulate the HIV susceptibility to PRIs. Mutations were introduced into the resistance test vector using the mega-primer PCR method for site-directed mutagenesis. (Sakar G and Sommar S S (1994) Biotechniques 8(4), 404–407) First, a resistance test vector was constructed that harbors a unique RsrII restriction site 590 bp downstream of the ApaI restriction site. The 590 bp ApaI-RsrII fragment thus contains the entire protease region. This site was introduced by site-specific oligonucleotide-directed mutagenesis using primer #4. All subsequent mutants were constructed by fragment-exchange of the wild-type ApaI-RsrII fragment in the parent vector with the equivalent fragment carrying the respective mutations.

A resistance test vector containing the N88S mutation (N88S-RTV) was tested using the phenotypic susceptibility assay described above and the results were compared to that of a genetically defined resistance test vector that was wild type at position 88. The pattern of phenotypic susceptibility to the PRIs in the N88S-RTV was altered as compared to wild type. In the context of an otherwise wild type background (i.e. N88S mutation alone) the N88S-RTV was more susceptible to both amprenavir and ritonavir and slightly less susceptible to nelfinavir compared to the wild type control RTV (see Table 2).

A resistance test vector containing the N88S mutation along with the L63P mutation (L63P-N88S-RTV) was tested using the phenotypic susceptibility assay described above and the results were compared to that of a genetically defined resistance test vector that was wild type at positions 63 and 88. The L63P-N88S-RTV showed decreased susceptibility to both indinavir and nelfinavir and an increase in the susceptibility to amprenavir compared the wild-type control RTV (see Table 2). Thus it appears that the introduction of a second mutation, L63P, in addition to N88S, results in a reduction in susceptibility to nelfinavir and indinavir while the increased susceptibility to amprenavir is maintained.

A resistance test vector containing the N88S mutation along with the L63P mutation and the V77I mutation (L63P-V77I-N88S-RTV) was tested using the phenotypic susceptibility assay described above and the results were compared to that of a genetically defined resistance test vector that was wild type at positions 63 and 77 and 88. The RTV containing mutations at these positions, L63P-V77I-N88S-RTV, showed a decrease in susceptibility to both indinavir and nelfinavir and an increase in the susceptibility to amprenavir compared to the wild-type control RTV (see FIG. 5 and Table 2). Thus it appears that the introduction of a third mutation, V77I, in addition to L63P and N88S, results in a reduction in susceptibility to nelfinavir and indinavir while the increased susceptibility to amprenavir is maintained.

The N88S mutation was also introduced into an RTV containing additional mutations at positions L63P and M46L (M46L+L63P+N88S). The RTV containing mutations at these positions, M46L-L63P-N88S-RTV showed a decrease in susceptibility to nelfinavir and a slight decrease in susceptibility to indinavir and an increase in the susceptibility to amprenavir compared to the wild-type control RTV (see FIG. 5 and Table 2) Thus it appears that the introduction of a third mutation, M46L, in addition to L63P and N88S, results in a reduction in susceptibility to nelfinavir and indinavir while the increased susceptibility to amprenavir is maintained.

A resistance test vector containing the N88S mutation along with the M46L mutation, the L63P mutation, and the V77I mutation (M46L-L63P-V77I-N88S-RTV) was tested using the phenotypic susceptibility assay described above and the results were compared to that of a genetically defined resistance test vector that was wild type at positions 46, 63, 77 and 88. The RTV containing mutations at these four positions, M46L-L63P-V77I-N88S-RTV showed a decrease in susceptibility to nelfinavir and indinavir and an increase in susceptibility to amprenavir compared to the wild-type control RTV (see FIG. 5 and Table 2). Thus it appears that the introduction of a fourth mutation, V77I, in addition to L63P, M46L and N88S results in a reduction in susceptibility to nelfinavir and indinavir while the increased susceptibility to amprenavir is maintained. A resistance test vector containing the L63P mutation (L63P-RTV) was tested using the phenotypic susceptibility assay described above and the results were compared to that of a genetically defined resistance test vector that was wild type at position 63. The pattern of phenotypic susceptibility to the PRIs in the L63P-RTV was similar to wild type with no significant changes in susceptibility to the PRIs observed.

The L63P mutation was also introduced into an RTV containing an additional mutation at position V77I. The L63P-V77I-RTV showed a slight decrease in susceptibility to nelfinavir compared to the wild-type control RTV (see FIG. 5 and Table 2).

EXAMPLE 5

Predicting Response to Protease Inhibitors by Characterization of Amino Acid 88 of HIV-1 Protease In one embodiment of this invention, changes in the amino acid at position 88 of the protease protein of HIV-1 is evaluated using the following method comprising: (i) collecting a biological sample from an HIV-1 infected subject; (ii) evaluating whether the biological sample contains nucleic acid encoding HIV-1 protease having an asparagine to serine mutation at codon 88 (N88S); and (iii) determining susceptibility to protease inhibitors (PRI).

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 88 of the HIV-1 protease is mutated to serine, can be performed using various methods, such as direct characterization of the viral nucleic acid encoding protease or direct characterization of the protease protein itself. Defining the amino acid at position 88 of protease can be performed by direct characterization of the protease protein by conventional or novel amino acid sequencing methodologies, epitope recognition by antibodies or other specific binding proteins or compounds. Alternatively, the amino acid at position 88 of the HIV-1 protease protein can be defined by characterizing amplified copies of HIV-1 nucleic acid encoding the protease protein. Amplification of the HIV-1 nucleic acid can be performed using a variety of methodologies including reverse transcription-polymerase chain reaction (RT-PCR), NASBA, SDA, RCR, or 3SR. The nucleic acid sequence encoding HIV protease at codon 88 can be determined by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid position 88 can be evaluated using a variety of probe hybridization methodologies, such as genechip hybridization sequencing (Affymetrix), line probe assay (LiPA; Murex), and differential hybridization (Chiron).

In a preferred embodiment of this invention, evaluation of protease inhibitor susceptibility and of whether amino acid position 88 of HIV-1 protease was wild type or serine was carried out using a phenotypic susceptibility assay or genotypic assay, respectively, using resistance test vector DNA prepared from the biological sample. In one embodiment, the plasma sample was collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, into an indicator gene viral vector thereby generating a resistance test vector. Resistance test vector DNA was isolated from the bacterial culture and the phenotypic susceptibility assay was carried out as described in Example 1. The results of the phenotypic susceptibility assay with a patient sample having an N88S mutation in PR is shown in FIG. 4. The nucleic acid (DNA) sequence of the patient derived HIV-1 protease and reverse transcriptase regions from patient sample 0732 was determined using a fluorescence detection chain termination cycle sequencing methodology (ABI/PE). The method was used to determine a consensus nucleic acid sequence representing the combination of sequences of the mixture of HIV-1 variants existing in the subject sample (representing the quasispecies), and to determine the nucleic acid sequences of individual variants.

Phenotypic and Genotypic Correlation of Mutations at Amino Acid 88 of HIV-1 Protease.

Phenotypic susceptibility profiles of patient samples and site directed mutants showed that amprenavir susceptibility correlated with the presence of the N88S mutation in HIV-1 protease. Phenotypic susceptibility profiles of patient samples and site directed mutants showed that a significant increase in amprenavir susceptibility (decreased resistance) correlated with a mutation in the nucleic acid sequence encoding the amino acid serine (S) at position 88 of HIV-1 protease.

Phenotypic susceptibility profiles of patient samples and site directed mutants showed reduction in amprenavir susceptibility (decreased resistance) and a decrease in susceptibility to nelfinavir and indinavir with the amino acid serine at position 88 when the PR mutations at positions 63, 77 or 46 were also present (L63P, V77I, or M46L).

EXAMPLE 6

Using Resistance Test Vectors and Site Directed Mutants to Correlate Genotypes Associated with Alterations in PRI Susceptibility with Viral Fitness Luciferase activity measured in the absence of drug for the seven resistance test vectors constructed from the patient viruses containing the N88S PR mutation ranged from 0.7 to 16% of control (Table 3). Although these viruses also contain multiple mutations in reverse transcriptase, which could also contribute to a reduction in viral fitness, the data suggest that viruses containing the N88S mutation are less fit than wild type. To confirm this observation, the luciferase expression level for the site-directed mutant resistance test vectors was also examined.

Viruses containing N88S as the only substitution produced only 1.0% of the luciferase activity in the absence of drug (Table 4). This reduction was substantially alleviated by the addition of the L63P substitution (20.7%) or by addition of the combinations of L63P/V77I (29.3%) or M46L/L63P (28.0%). The L63P or L63P/V77I mutants had equivalent or increased relative luciferase activity compared to wild type (163.9 and 75.6%, respectively).

When the K20T substitution was added to the N88S background, either alone or in combination with L63P, only background levels of luciferase activity was detected. Sequence analysis confirmed the absence of additional mutations, which might render the vector inactive. Thus the combination of the K20T and N88S substitutions correlates with a severe defect in fitness.

EXAMPLE 7

Predicting Response to Protease Inhibitors by Characterization of Amino Acid 82 of HIV-1 Protease In one embodiment of this invention, changes in the amino acid at position 82 of the protease protein of HIV-1 are evaluated using the following method comprising: (i) collecting a biological sample from an HIV-1 infected subject; (ii) evaluating whether the biological sample contains nucleic acid encoding HIV-1 protease having a valine to alanine (V82A), phenylalanine (V82F), serine (V82S), or threonine (V82T) substitution at codon 82; and (iii) determining susceptibility to protease inhibitors (PRI).

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 82 of the HIV-1 protease is mutated to alanine, phenylalanine, serine, or threonine, can be performed using various methods, such as direct characterization of the viral nucleic acid encoding protease or direct characterization of the protease protein itself. Defining the amino acid at position 82 of protease can be performed by direct characterization of the protease protein by conventional or novel amino acid sequencing methodologies, epitope recognition by antibodies or other specific binding proteins or compounds. Alternatively, the amino acid at position 82 of the HIV-1 protease protein can be defined by characterizing amplified copies of HIV-1 nucleic acid encoding the protease protein. Amplification of the HIV-1 nucleic acid can be performed using a variety of methodologies including reverse transcription-polymerase chain reaction (RT-PCR), NASBA, SDA, RCR, or 3SR. The nucleic acid sequence encoding HIV protease at codon 82 can be determined by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid position 82 can be evaluated using a variety of probe hybridization methodologies, such as genechip hybridization sequencing (Affymetrix), line probe assay (LiPA; Murex), and differential hybridization (Chiron).

In a preferred embodiment of this invention, evaluation of protease inhibitor susceptibility and of whether amino acid position 82 of HIV-1 protease was wild type or alanine, phenylalanine, serine, or threonine, was carried out using a phenotypic susceptibility assay or genotypic assay, respectively, using resistance test vector DNA prepared from the biological sample. In one embodiment, the plasma sample was collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, into an indicator gene viral vector thereby generating a resistance test vector. Resistance test vector DNA was isolated from the bacterial culture and the phenotypic susceptibility assay was carried out and analyzed as described in Example 1.

The nucleic acid (DNA) sequence of the patient derived HIV-1 protease and reverse transcriptase regions was determined using a fluorescence detection chain termination cycle sequencing methodology (ABI/PE). The method was used to determine a consensus nucleic acid sequence representing the combination of sequences of the mixture of HIV-1 variants existing in the subject sample (representing the quasispecies), and to determine the nucleic acid sequences of individual variants. Genotypes are analyzed as lists of amino acid differences between virus in the patient sample and a reference laboratory strain of HIV-1, NL4-3. Genotypes and corresponding phenotypes (fold-change in IC50 values) are entered in a relational database linking these two results with patient information. Large datasets can then be assembled from patient virus samples sharing particular characteristics, such as the presence of any given mutation, or combination of mutations or reduced susceptibility to any drug or combination of drugs.

(a) Protease Inhibitor Susceptibility of Viruses Containing Mutations at Amino Acid 82 of HIV-1 Protease.

Phenotypic susceptibility profiles of 75 patient virus samples which contained a mutation at position 82 (V82A, F, S, or T), but no other primary mutations, were analyzed. According to most published guidelines, such viruses are expected to be resistant to ritonavir, nelfinavir, indinavir, and saquinavir. However, 8%, 20%, 23%, and 73% of these samples were phenotypically susceptible to these four protease inhibitors, respectively (see Table 6). Thus, particularly for indinavir and saquinavir, there was poor correlation between the presence of mutations at position 82 and drug susceptibility.

(b) Indinavir Susceptibility of Viruses Containing Combinations of Mutations at Amino Acid 82 and One Secondary Mutation in HIV-1 Protease.

Indinavir resistance in viruses containing mutations at position 82 was evaluated with respect to the presence of other specific mutations. Decreased indinavir susceptibility (fold-change in $IC_{50}$ greater than 2.5) in viruses containing V82A, F, S, or T but no other primary mutations was correlated with the presence of mutations at secondary positions. Reduced indinavir susceptibility was observed in 20 samples containing mutations at both positions 24 and 82 (100%) and in 27 samples with both 71 and 82 (100%) (See Table 7). The combination of mutations at position 82 with mutations at other positions (e.g. 54, 46, 10, and 63) also significantly increased the proportion of samples that had reduced indinavir susceptibility (Table 7).

(c) Saquinavir Susceptibility of Viruses Containing Combinations of Mutations at Amino Acid 82 and One Secondary Mutation in HIV-1 Protease.

Saquinavir resistance in viruses containing mutations at position 82 was evaluated with respect to the presence of other specific mutations. Decreased saquinavir susceptibility (fold-change in $IC_{50}$ greater than 2.5) in viruses containing V82A, F, S, or T but no other primary mutations was correlated with the presence of mutations at secondary positions. Reduced saquinavir susceptibility was observed in 4 of 5 samples containing mutations at both positions 20 and 82 (80%) and in 8 of 11 samples with both 36 and 82 (73%) (See Table 8). The combination of mutations at position 82 with mutations at other positions (e.g. 24, 71, 54, and 10) also significantly increased the proportion of samples that had reduced saquinavir susceptibility (Table 8).

(d) Indinavir Susceptibility of Viruses Containing Combinations of Mutations at Amino Acid 82 and Many Secondary Mutations in HIV-1 Protease.

Indinavir resistance in viruses containing mutations at position 82 was evaluated with respect to the presence of a defined number of other mutations. Decreased indinavir susceptibility (fold-change in $IC_{50}$ greater than 2.5) in viruses containing V82A, F, S, or T but no other primary mutations was correlated with the number of mutations at secondary positions. Reduced indinavir susceptibility was observed in 100% of samples with V82A, F, S, or T and at least 6 other secondary mutations (See Table 9). The proportion of samples that had reduced indinavir susceptibility increased significantly in samples with V82A, F, S, or T combined with 3 to 5 other secondary mutations (Table 9).

(e) Saquinavir Susceptibility of Viruses Containing Combinations of Mutations at Amino Acid 82 and Many Secondary Mutations in HIV-1 Protease.

Saquinavir resistance in viruses containing mutations at position 82 was evaluated with respect to the presence of a defined number of other mutations. Decreased saquinavir susceptibility (fold-change in $IC_{50}$ greater than 2.5) in viruses containing V82A, F, S, or T but no other primary mutations was correlated with the number of mutations at secondary positions. Reduced saquinavir susceptibility was observed in 60 to 76% of samples with V82A, F, S, or T and at least 5 other secondary mutations (See Table 9). The proportion of samples that had reduced saquinivir susceptibility increased significantly in samples with V82A, F, S, or T combined with 3 or 4 other secondary mutations (Table 9).

EXAMPLE 8

Predicting Response to Protease Inhibitors by Characterization of Amino Acid 90 of HIV-1 Protease In one embodiment of this invention, changes in the amino acid at position 90 of the protease protein of HIV-1 are evaluated using the following method comprising: (i) collecting a biological sample from an HIV-1 infected subject; (ii) evaluating whether the biological sample contains nucleic acid encoding HIV-1 protease having a leucine to methionine (L90M) substitution at codon 90; and (iii) determining susceptibility to protease inhibitors (PRI).

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 90 of the HIV-1 protease is mutated to methionine, can be performed using various methods, such as direct characterization of the viral nucleic acid encoding protease or direct characterization of the protease protein itself. Defining the amino acid at position 90 of protease can be performed by direct characterization of the protease protein by conventional or novel amino acid sequencing methodologies, epitope recognition by antibodies or other specific binding proteins or compounds. Alternatively, the amino acid at position 90 of the HIV-1 protease protein can be defined by characterizing amplified copies of HIV-1 nucleic acid encoding the protease protein. Amplification of the HIV-1 nucleic acid can be performed using a variety of methodologies including reverse transcription-polymerase chain reaction (RT-PCR), NASBA, SDA, RCR, or 3SR. The nucleic acid sequence encoding HIV protease at codon 90 can be determined by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid position 90 can be evaluated using a variety of probe hybridization methodologies, such as gene-chip hybridization sequencing (Affymetrix), line probe assay (LIPA; Murex), and differential hybridization (Chiron).

In a preferred embodiment of this invention, evaluation of protease inhibitor susceptibility and of whether amino acid position 90 of HIV-1 protease was wild type or methionine, was carried out using a phenotypic susceptibility assay or genotypic assay, respectively, using resistance test vector DNA prepared from the biological sample. In one embodiment, the plasma sample was collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, into an indicator gene viral vector thereby generating a resistance test vector. Resistance test vector DNA was isolated from the bacterial culture and the phenotypic susceptibility assay was carried out and analyzed as described in Example 1.

The nucleic acid (DNA) sequence of the patient derived HIV-1 protease and reverse transcriptase regions was determined using a fluorescence detection chain termination cycle sequencing methodology (ABI/PE). The method was used to determine a consensus nucleic acid sequence representing the combination of sequences of the mixture of HIV-1 variants existing in the subject sample (representing the quasispecies), and to determine the nucleic acid sequences of individual variants. Genotypes are analyzed as lists of amino acid differences between virus in the patient sample and a reference laboratory strain of HIV-1, NL4-3. Genotypes and corresponding phenotypes (fold-change in IC50 values) are entered in a relational database linking these two results with patient information. Large datasets can then be assembled from patient virus samples sharing particular characteristics, such as the presence of any given mutation, or combination of mutants, or reduced susceptibility to any drug or combination of drugs.

(a) Protease Inhibitor Susceptibility of Viruses Containing Mutations at Amino Acid 90 of HIV-1 Protease.

Phenotypic susceptibility profiles of 58 patient virus samples which contained a mutation at position 90 (L90M), but no other primary mutations, were analyzed. According to most published guidelines, such viruses are expected to be resistant to ritonavir, nelfinavir, indinavir, and saquinavir. However, 28%, 9%, 31%, and 47% of these samples were phenotypically susceptible to these four protease inhibitors, respectively (see Table 6). Thus, particularly for indinavir and saquinavir, there was poor correlation between the presence of mutations at position 90 and drug susceptibility.

(b) Indinavir Susceptibility of Viruses Containing Combinations of Mutations at Amino Acid 90 and One Secondary Mutation in HIV-1 Protease.

Indinavir resistance in viruses containing mutations at position 90 was evaluated with respect to the presence of other specific mutations. Decreased indinavir susceptibility (fold-change in $IC_{50}$ greater than 2.5) in viruses containing L90M but no other primary mutations was correlated with the presence of mutations at secondary positions. Reduced indinavir susceptibility was observed in 17 of 19 samples containing mutations at both positions 73 and 90 (89%) and in 16 of 18 samples with both 71 and 90 (89%) (See Table 10). The combination of mutations at position 90 with mutation at position 46 also significantly increased the proportion of samples that had reduced indinavir susceptibility (Table 10).

(c) Saquinavir Susceptibility of Viruses Containing Combinations of Mutations at Amino Acid 90 and One Secondary Mutation in HIV-1 Protease.

Saquinavir resistance in viruses containing mutations at position 90 was evaluated with respect to the presence of other specific mutations. Decreased saquinavir susceptibility (fold-change in $IC_{50}$ greater than 2.5) in viruses containing L90M but no other primary mutations was correlated with the presence of mutations at secondary positions. Reduced saquinavir susceptibility was observed in 15 of 19 samples containing mutations at both positions 73 and 90 (79%) and in 14 of 18 samples with both 71 and 90 (78%) (See Table 11). The combination of mutations at position 90 with mutations at other positions (e.g. 77 and 10) also significantly increased the proportion of samples that had reduced saquinavir susceptibility (Table 1).

(d) Indinavir Susceptibility of Viruses Containing Combinations of Mutations at Amino Acid 90 and Many Secondary Mutations in HIV-1 Protease.

Indinavir resistance in viruses containing mutations at position 90 was evaluated with respect to the presence of a defined number of other mutations. Decreased indinavir susceptibility (fold-change in $IC_{50}$ greater than 2.5) in viruses containing L90M but no other primary mutations was correlated with the number of mutations at secondary positions. Reduced indinavir susceptibility was observed in 100% of samples with L90M and at least 5 other secondary mutations had (See Table 12). The proportion of samples that had reduced indinavir susceptibility increased significantly in samples with L90M combined with 3 or 4 other secondary mutations (Table 12).

(e) Saquinavir Susceptibility of Viruses Containing Combinations of Mutations at Amino Acid 90 and Many Secondary Mutations in HIV-1 Protease.

Saquinavir resistance in viruses containing mutations at position 90 was evaluated with respect to the presence of a defined number of other mutations. Decreased saquinavir susceptibility (fold-change in $IC_{50}$ greater than 2.5) in viruses containing L90M but no other primary mutations was correlated with the number of mutations at secondary positions. Reduced saquinavir susceptibility was observed in 100% of samples with L90M and at least 5 other secondary mutations (See Table 12). The proportion of samples that had reduced saquinivir susceptibility increased significantly in samples with L90M combined with 3 or 4 other secondary mutations (Table 12).

EXAMPLE 9

Predicting Response to Protease Inhibitors by Characterization of Amino Acids 82 and 90 of HIV-1 Protease In one embodiment of this invention, changes in the amino acid at position 82 and 90 of the protease protein of HIV-1 are evaluated using the following method comprising: (i) collecting a biological sample from an HIV-1 infected subject; (ii) evaluating whether the biological sample contains nucleic acid encoding HIV-1 protease having a valine to alanine (V82A), phenylalanine (V82F), serine (V82S), or threonine (V82T) substitution at codon 82 or a leucine to methionine at position 90 (L90M); and (iii) determining susceptibility to protease inhibitors (PRI).

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 82 of the HIV-1 protease is mutated to alanine, phenylalanine, serine, or threonine or at position 90 to methionine, can be performed using various methods, such as direct characterization of the viral nucleic acid encoding protease or direct characterization of the protease protein itself. Defining the amino acid at positions 82 and 90 of protease can be performed by direct characterization of the protease protein by conventional or novel amino acid sequencing methodologies, epitope recognition by antibodies or other specific binding proteins or compounds. Alternatively, the amino acid at positions 82 and 90 of the HIV-1 protease protein can be defined by characterizing amplified copies of HIV-1 nucleic acid encoding the protease protein. Amplification of the HIV-1 nucleic acid can be performed using a variety of methodologies including reverse transcription-polymerase chain reaction (RT-PCR), NASBA, SDA, RCR, or 3SR. The nucleic acid sequence encoding HIV protease at codons 82 and 90 can be determined by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid positions 82 and 90 can be evaluated using a variety of probe hybridization methodologies, such as genechip hybridization sequencing (Affymetrix), line probe assay (LiPA; Murex), and differential hybridization (Chiron).

In a preferred embodiment of this invention, evaluation of protease inhibitor susceptibility and of whether amino acid positions 82 and 90 of HIV-1 protease was wild type or alanine, phenylalanine, serine, or threonine in the case of position 82 and methionine at position 90, was carried out using a phenotypic susceptibility assay or genotypic assay, respectively, using resistance test vector DNA prepared from the biological sample. In one embodiment, plasma sample was collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, into an indicator gene viral vector thereby generating a resistance test vector. Resistance test vector DNA was isolated from the bacterial culture and the phenotypic susceptibility assay was carried out and analyzed as described in Example 1.

The nucleic acid (DNA) sequence of the patient derived HIV-1 protease and reverse transcriptase regions was determined using a fluorescence detection chain termination cycle sequencing methodology (ABI/PE). The method was used to determine a consensus nucleic acid sequence representing the combination of sequences of the mixture of HIV-1 variants existing in the subject sample (representing the quasispecies), and to determine the nucleic acid sequences of individual variants. Genotypes are analyzed as lists of amino acid differences between virus in the patient sample and a reference laboratory strain of HIV-1, NL4-3. Genotypes and corresponding phenotypes (fold-change in IC50 values) are entered in a relational database linking these two results with patient information. Large datasets can then be assembled from patient virus samples sharing particular characteristics, such as the presence of any given mutation or reduced susceptibility to any drug or combination of drugs.

Protease Inhibitor Susceptibility of Viruses Containing Mutations at Amino Acids 82 and 90 of HIV-1 Protease.

Phenotypic susceptibility profiles of 33 patient virus samples which contained mutations at positions 82 (V82A, F, S, or T) and 90 (L90M), but no other primary mutations, were analyzed. According to most published guidelines, such viruses are expected to be resistant to ritonavir, nelfinavir, indinavir, and saquinavir. However, 9% and 21% of these samples were phenotypically susceptible to indinavir and saquinavir, respectively (see Table 6). Thus, particularly for saquinavir, there was poor correlation between the presence of mutations at positions 82 and 90 and drug susceptibility.

EXAMPLE 10

Measuring Replication Fitness Using Resistance Test Vectors

A means and method is provided for accurately measuring and reproducing the replication fitness of HIV-1. This method for measuring replication fitness is applicable to other viruses, including, but not limited to hepadnaviruses (human hepatitis B virus), flaviviruses (human hepatitis C virus) and herpesviruses (human cytomegalovirus). This example further provides a means and method for measuring the replication fitness of HIV-1 that exhibits reduced drug susceptibility to reverse transcriptase inhibitors and protease inhibitors. This method can be used for measuring replication fitness for other classes of inhibitors of HIV-1 replication, including, but not limited to integration, virus assembly, and virus attachment and entry.

Replication fitness tests are carried out using the means and methods for phenotypic drug susceptibility and resistance tests described in U.S. Pat. No. 5,837,464 (International Publication Number WO 97/27319) which is hereby incorporated by reference.

In these experiments patient-derived segment(s) corresponding to the HIV protease and reverse transcriptase coding regions were either patient-derived segments amplified by the reverse transcription-polymerase chain reaction method (RT-PCR) using viral RNA isolated from viral particles present in the serum of HIV-infected individuals or were mutants of wild type HIV-1 made by site directed mutagenesis of a parental clone of resistance test vector DNA. Resistance test vectors are also referred to as "fitness test vectors" when used to evaluate replication fitness. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into cDNA. The cDNA was then amplified using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216–2220) [e.g. Expand High Fidelity PCR System (Taq+ Pwo), (Boehringer Mannheim. Indianapolis, Ind.) OR GeneAmp XL PCR kit (Tth+Vent), (Roche Molecular Systems, Inc., Branchburg, N.J.)].

PCR6 (Table 5, #1) is used for reverse transcription of viral RNA into cDNA. The primers, ApaI primer (PDSApa, Table 5, #2) and AgeI primer (PDSAge, Table 5, #3) used to amplify the "test" patient-derived segments contained sequences resulting in ApaI and AgeI recognition sites being introduced into both ends of the PCR product, respectively.

Fitness test vectors incorporating the "test" patient-derived segments were constructed as described in U.S. Pat. No. 5,837,464 (International Publication Number WO 97/27319) (see FIG. 1) using an amplified DNA product of 1.5 kB prepared by RT-PCR using viral RNA as a template and oligonucleotides PCR6 (#1), PDSApa (#2) and PDSAge (#3) as primers, followed by digestion with ApaI and AgeI or the isoschizomer PinA1. To ensure that the plasmid DNA corresponding to the resultant fitness test vector comprises a representative sample of the HIV viral quasi-species present in the serum of a given patient, many (>100) independent *E. coli* transformants obtained in the construction of a given fitness test vector were pooled and used for the preparation of plasmid DNA.

A packaging expression vector encoding an amphotrophic MuLV 4070A env gene product enables production in a fitness test vector host cell of fitness test vector viral particles which can efficiently infect human target cells. Fitness test vectors encoding all HIV genes with the exception of env were used to transfect a packaging host cell (once transfected the host cell is referred to as a fitness test vector host cell). The packaging expression vector which encodes the amphotrophic MuLV 4070A env gene product is used with the resistance test vector to enable production in the fitness test vector host cell of infectious pseudotyped fitness test vector viral particles.

Fitness tests performed with fitness test vectors were carried out using packaging host and target host cells consisting of the human embryonic kidney cell line 293 (Cell Culture Facility, UC San Francisco, SF, Calif.)

Figure 6:
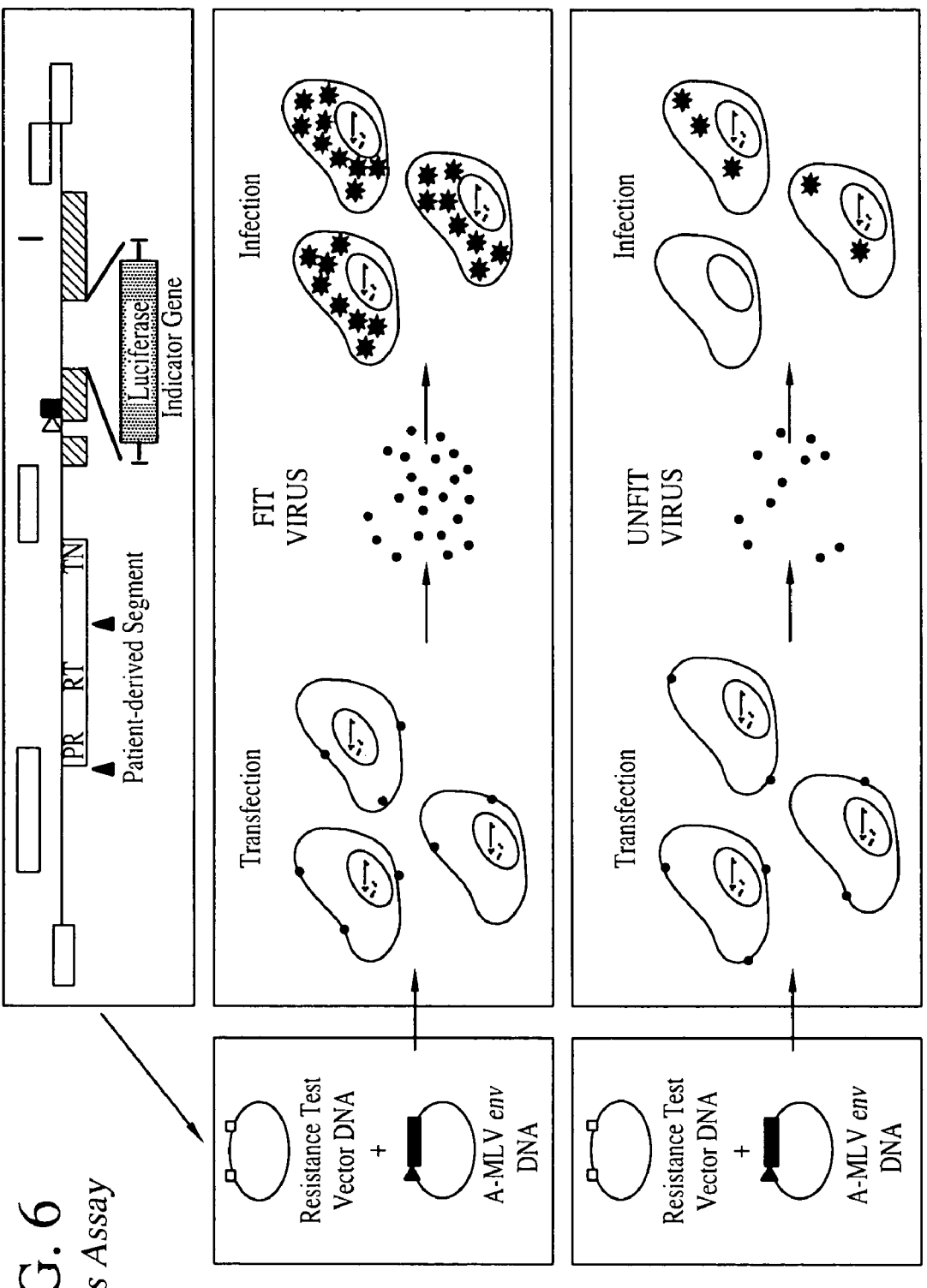
Figure 7:
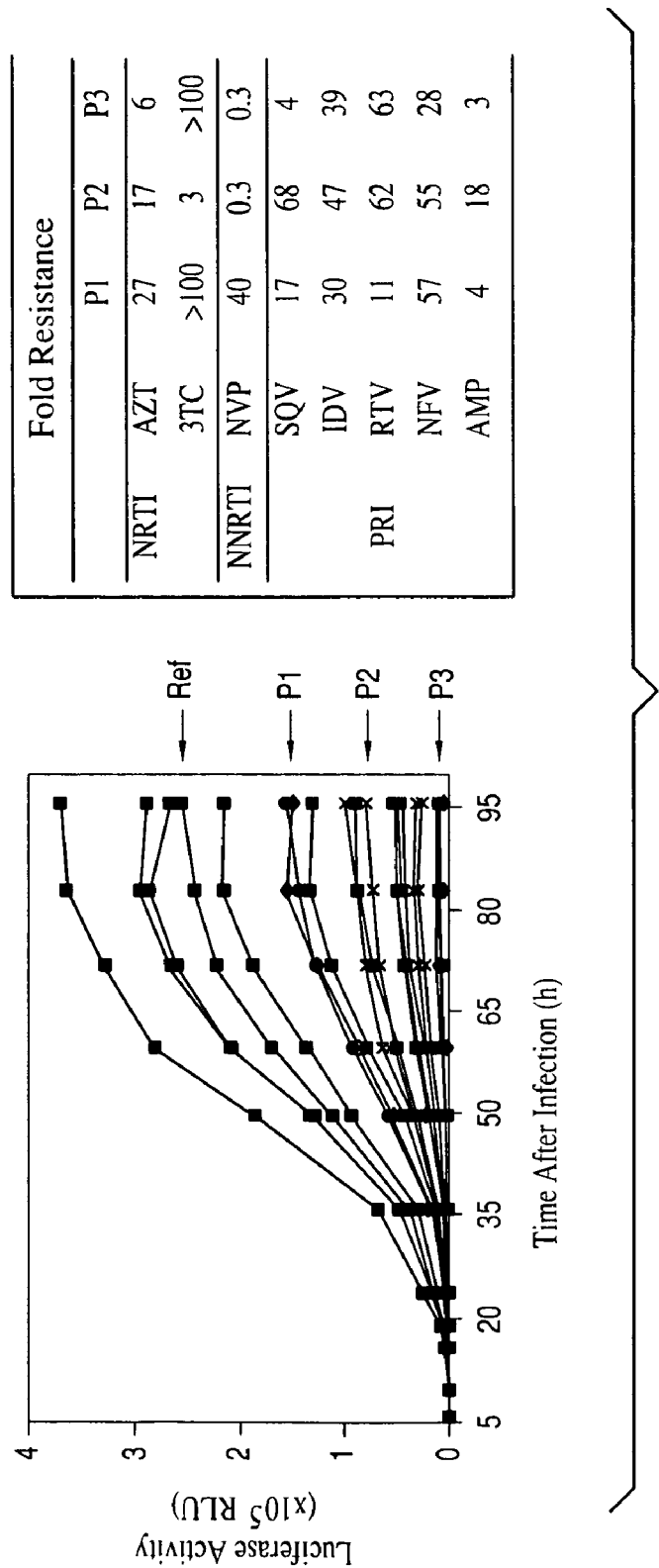

Fitness tests were carried out with fitness test vectors using two host cell types. Fitness test vector viral particles were produced by a first host cell (the fitness test vector host cell) that was prepared by transfecting a packaging host cell with the fitness test vector and the packaging expression vector. The fitness test vector viral particles were then used to infect a second host cell (the target host cell) in which the expression of the indicator gene is measured (see FIG. 6).

The fitness test vectors containing a functional luciferase gene cassette were constructed and host cells were transfected with the fitness test vector DNA. The fitness test vectors contained patient-derived reverse transcriptase and protease DNA sequences that encode proteins which were either susceptible or resistant to the antiretroviral agents, such as nucleoside reverse transcriptase inhibitors, non-nucleoside reverse transcriptase inhibitors and protease inhibitors.

The amount of luciferase activity detected in the infected cells is used as a direct measure of "infectivity", "replication capacity" or "fitness", i.e. the ability of the virus to complete a single round of replication. Relative fitness is assessed by comparing the amount of luciferase activity produced by patient derived viruses to the amount of luciferase activity produced by a well-characterized reference virus (wildtype) derived from a molecular clone of HIV-1, for example NL4-3 or HXB2. Fitness measurements are expressed as a percent of the reference, for example 25%, 50%, 75%, 100% or 125% of reference (FIGS. 6B, 6C).

Host cells were seeded in 10-cm-diameter dishes and were transfected one day after plating with fitness test vector plasmid DNA and the envelope expression vector. Transfections were performed using a calcium-phosphate co-precipitation procedure. The cell culture media containing the DNA precipitate was replaced with fresh medium, from one to 24 hours, after transfection. Cell culture media containing fitness test vector viral particles was harvested one to four days after transfection and was passed through a 0.45-mm filter before being stored at −80° C. HIV capsid protein (p24) levels in the harvested cell culture media were determined by an EIA method as described by the manufacturer (SIAC; Frederick, Md.). Before infection, target cells (293 and 293/T) were plated in cell culture media. Control infections were performed using cell culture media from mock transfections (no DNA) or transfections containing the fitness test vector plasmid DNA without the envelope expression plasmid. One to three or more days after infection the media was removed and cell lysis buffer (Promega) was added to each well. Cell lysates were assayed for luciferase activity. Alternatively, cells were lysed and luciferase was measured by adding Steady-Glo (Promega) reagent directly to each well without aspirating the culture media from the well.

EXAMPLE 11

Measuring Replication Fitness of Viruses with Deficiencies in Reverse Transcriptase Activity A means and method is provided for identifying mutations in reverse transcriptase that alter replication fitness. A means and method is provided for identifying mutations that alter replication fitness and can be used to identify mutations associated with other aspects of HIV-1 replication, including, but not limited to integration, virus assembly, and virus attachment and entry. This example also provides a means and method for quantifying the affect that specific mutations reverse transcriptase have on replication fitness. A means and method for quantifying the affect that specfic protease and reverse transcriptase mutations have on replication fitness to mutations in other viral genes involved in HIV-1 replication, including, but not limited to the gag, pol, and envelope genes is also provided.

Figure 8:
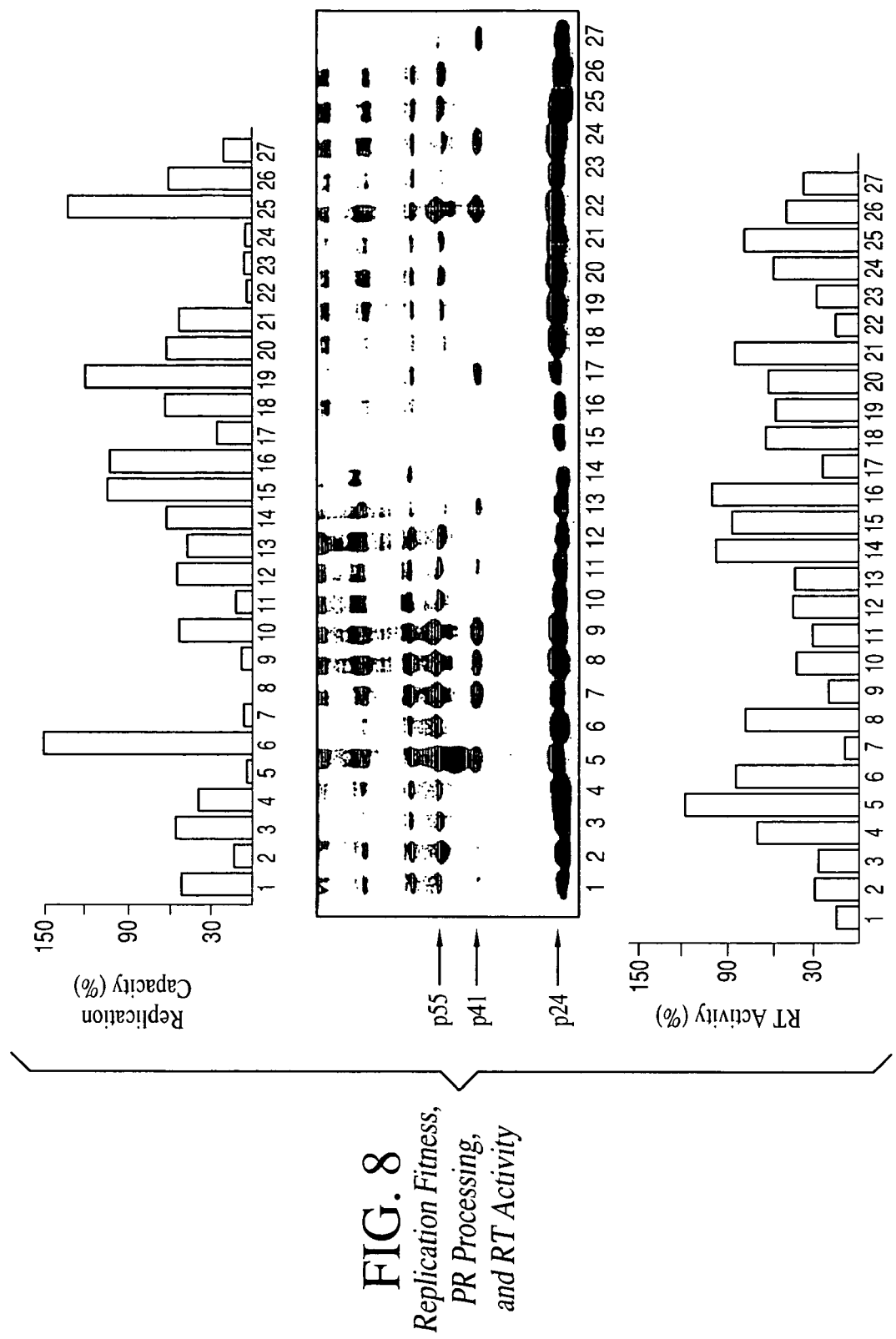

Fitness test vectors were constructed as described in example 10. Fitness test vectors derived from patient samples or clones derived from the fitness test vector pools, or fitness test vectors were engineered by site directed mutagenesis to contain specific mutations, and were tested in a fitness assay to determine accurately and quantitatively the relative fitness compared to a well-characterized reference standard. A patient sample was examined for increased or decreased reverse transcriptase activity and correlated with the relative fitness observed (FIG. 8).

Reverse Transcriptase Activity of Patient HIV Samples

Reverse transcriptase activity can be measured by any number of widely used assay procedures, including but not limited to homopolymeric extension using (e.g. oligo dT:poly rC) or real time PCR based on molecular beacons (reference Kramer) or 5' exonuclease activity (Lie and Petropoulos, 1996). In one embodiment, virion associated reverse transcriptase activity was measured using a quantitative PCR assay that detects the 5' exonuclease activity associated with thermo-stable DNA polymerases (FIG. 8). In one embodiment of the invention, the fitness of the patient virus was compared to a reference virus to determine the relative fitness compared to "wildtype" viruses that have not been exposed to reverse transcriptase inhibitor drugs. In another embodiment, the fitness of the patient virus was compared to viruses collected from the same patient at different timepoints, for example prior to initiating therapy, before or after changes in drug treatment, or before or after changes in virologic (RNA copy number), immunologic (CD4 T-cells), or clinical (opportunistic infection) markers of disease progression.

Genotypic Analysis of Patient HIV Samples

Fitness test vector DNAs, either pools or clones, are analyzed by any of the genotyping methods described in Example 1. In one embodiment of the invention, patient HIV sample sequences were determined using viral RNA purification, RT/PCR and ABI chain terminator automated sequencing. The sequence was determined and compared to reference sequences present in the database or compared to a sample from the patient prior to initiation of therapy. The genotype was examined for sequences that are different from the reference or pre-treatment sequence and correlated to the observed fitness.

Fitness Analysis of Site Directed Mutants

Figure 9:
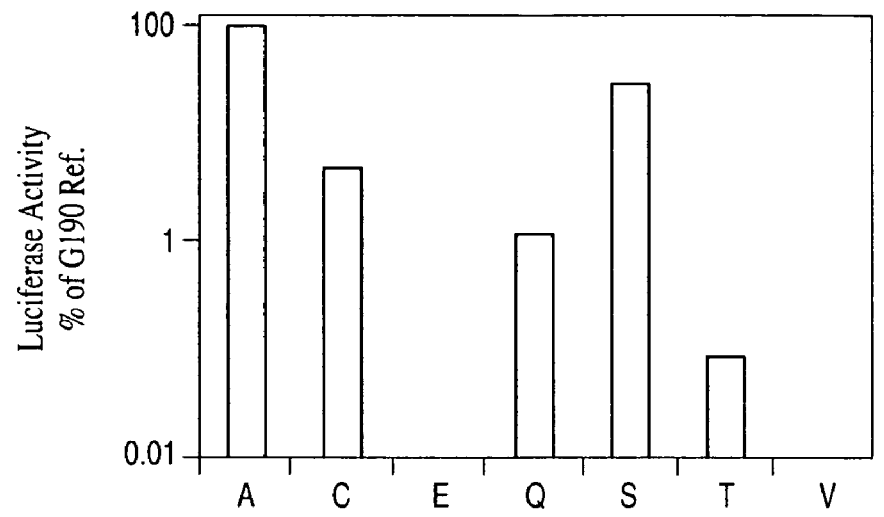
Figure 9:
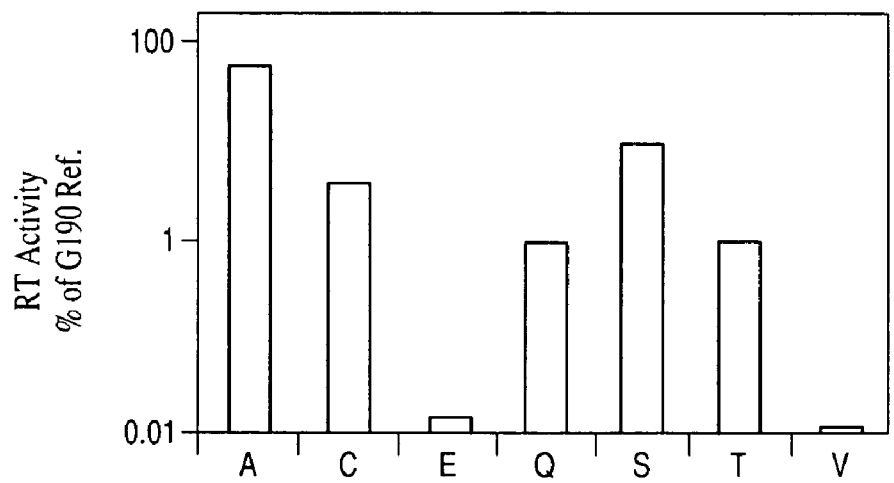

Genotypic changes that are observed to correlate with changes in fitness were evaluated by construction of fitness vectors containing the specific mutation on a defined, wild-type (drug susceptible) genetic background. Mutations may be incorporated alone and/or in combination with other mutations that are thought to modulate the fitness of a virus. Mutations were introduced into the fitness test vector through any of the widely known methods for site-directed mutagenesis. In one embodiment of this invention the mega-primer PCR method for site-directed mutagenesis is used. A fitness test vector containing the specific mutation or group of mutations were then tested using the fitness assay described in Example 10 and the fitness was compared to that of a genetically defined wild-type (drug susceptible) fitness test vector which lacks the specific mutations. Observed changes in fitness are attributed to the specific mutations introduced into the resistance test vector. In several related embodiments of the invention, fitness test vectors containing site directed mutations in reverse transcriptase that result in amino acid substitutions at position 190 (G190A, G190S, G190C, G190E, G190V, G190T) and that display different amounts of reverse transcriptase activity were constructed and tested for fitness (FIG. 9). The fitness results were correlated with specific reverse transcriptase amino acid substituions and fitness.

EXAMPLE 12

Measuring Replication Fitness of Viruses with Deficiencies in Protease Activity A means and method for identifying mutations in protease that alter replication fitness is provided.

This example provides the means and methods for identifying mutations that alter replication fitness for various components of HIV-1 replication, including, but not limited to integration, virus assembly, and virus attachment and entry. This example also provides a means and method for quantifying the affect that specific mutations in protease or reverse transcriptase have on replication fitness. This method can be used for quantifying the effect that specific protease mutations have on replication fitness and can be used to quantify the effect of other mutations in other viral genes involved in HIV-1 replication, including, but not limited to the gag, pol, and envelope genes.

Fitness test vectors were constructed as described in example 10. Fitness test vectors derived from patient samples or clones derived from the fitness test vector pools, or fitness test vectors engineered by site directed mutagenesis to contain specific mutations, were tested in a fitness assay to determine accurately and quantitatively the relative fitness compared to a well-characterized reference standard. A patient sample was examined further for increased or decreased protease activity correlated with the relative fitness observed (FIG. 8).

Protease Activity of Patient HIV Samples

Protease activity can be measured by any number of widely used assay procedures, including but not limited to in vitro reactions that measure protease cleavage activity (reference Erickson). In one embodiment, protease cleavage of the gag polyprotein (p55) was measured by Western blot analyis using an anti-capsid (p24) antibody (FIG. 8). In one embodiment of the invention, the fitness of the patient virus was compared to a reference virus to determine the relative fitness compared to "wildtype" viruses that have not been exposed to protease inhibitor drugs. In another embodiment, the fitness of the patient virus was compared to viruses collected from the same patient at different timepoints, for example prior to initiating therapy, before or after changes in drug treatment, or before or after changes in virologic (RNA copy number), immunologic (CD4 T-cells), or clinical (opportunistic infection) markers of disease progression.

Genotypic Analysis of Patient HIV Samples

Fitness test vector DNAs, either pools or clones, are analyzed by any of the genotyping methods described in Example 1. In one embodiment of the invention, patient HIV sample sequences were determined using viral RNA purification, RT/PCR and ABI chain terminator automated sequencing. The sequence was determined and compared to reference sequences present in the database or compared to a sample from the patient prior to initiation of therapy, if available. The genotype was examined for sequences that are different from the reference or pre-treatment sequence and correlated to the observed fitness.

Fitness Analysis of Site Directed Mutants

Figure 10:
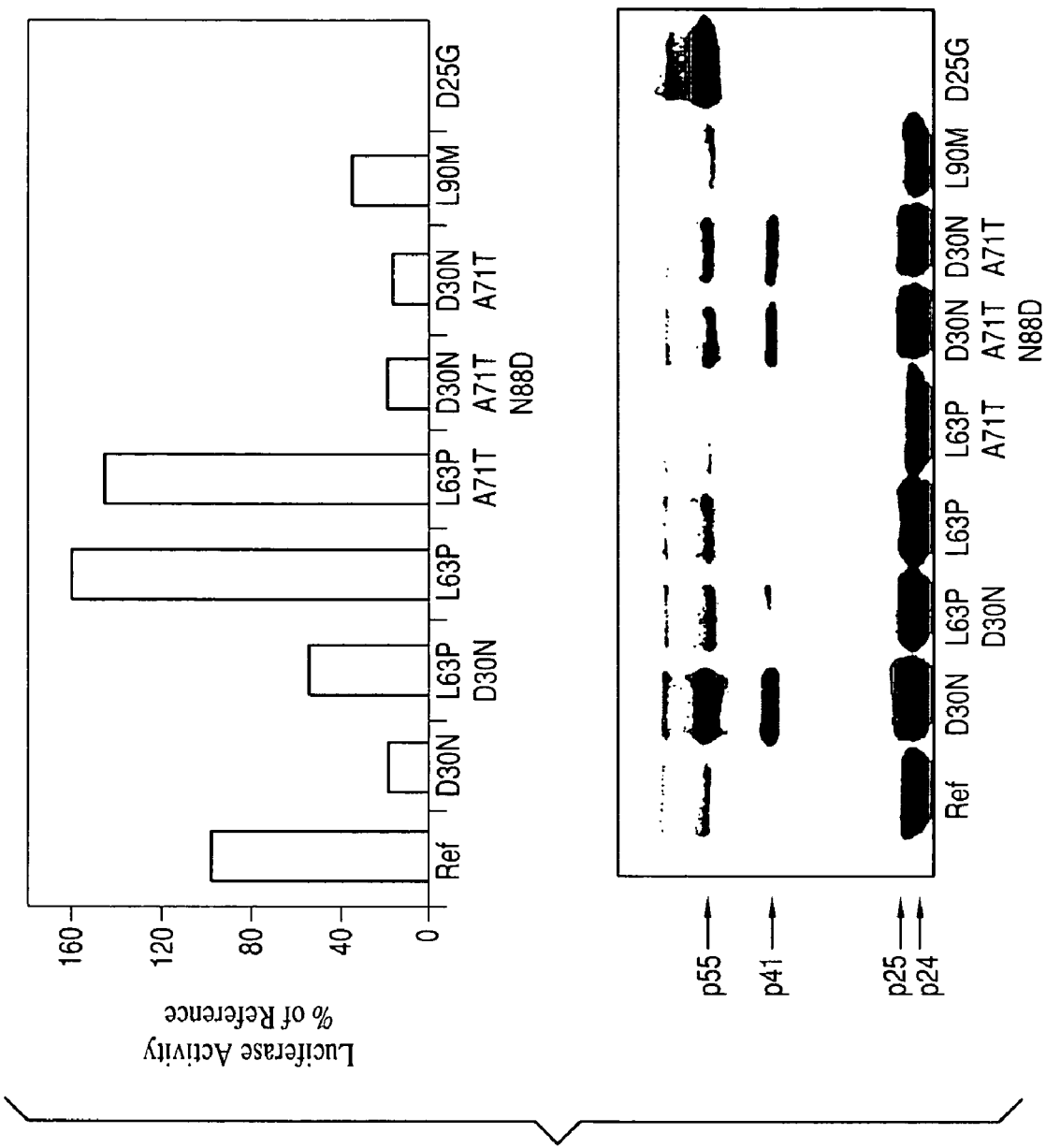

Genotypic changes that are observed to correlate with changes in fitness are evaluated by construction of fitness vectors containing the specific mutation on a defined, wild-type (drug susceptible) genetic background. Mutations may be incorporated alone and/or in combination with other mutations that are thought to modulate the fitness of a virus. Mutations are introduced into the fitness test vector through any of the widely known methods for site-directed mutagenesis. In one embodiment of this invention the mega-primer PCR method for site-directed mutagenesis is used. A fitness test vector containing the specific mutation or group of mutations are then tested using the fitness assay described in Example 10 and the fitness is compared to that of a genetically defined wild-type (drug susceptible) fitness test vector which lacks the specific mutations. Observed changes in fitness are attributed to the specific mutations introduced into the fitness test vector. In several related embodiments of the invention, fitness test vectors containing site directed mutations in reverse protease that result in amino acid substitutions at positions 30, 63, 77, 90 (list from FIG. 10) and that display different amounts of protease activity are constructed and tested for fitness (FIG. 10). The fitness results enable the correlation between specific protease amino acid substitutions and changes in viral fitness.

EXAMPLE 13

Measuring Replication Fitness and Drug Susceptibility in a Large Patient Population This example describes the high incidence of patient samples with reduced replication fitness. This example also describes the general correlation between reduced drug susceptibility and reduced replication fitness. This example further describes the occurrence of viruses with reduced fitness in patients receiving protease inhibitor and/or reverse transcriptase inhibitor treatment. This example further describes the incidence of patient samples with reduced replication fitness in which the reduction in fitness is due to altered protease processing of the gag polyprotein (p55). This example further describes the incidence of protease mutations in patient samples that exhibit low, moderate or normal (wildtype) replication fitness. This example further describes protease mutations that are frequently observed, either alone or in combination, in viruses that exhibit reduced replication capacity. This example also describes the incidence of patient samples with reduced replication fitness in which the reduction in fitness is due to altered reverse transcriptase activity. This example describes the occurrence of viruses with reduced replication fitness in patients failing antiretroviral drug treatment.

Fitness/resistance test vectors were constructed as described in example 10. Fitness and drug susceptibility was measured in 134 random patient samples that were received for routing phenotypic testing by the Virologic Clinical Reference Laboratory. Fitness assays were performed as described in Example 10. Drug susceptibility testing and genotyping of the protease region was performed as described in Example 1. Reverse transcriptase activity was measured as described in Example 11. Protease processing was measured as described in Example 12.

Drug Susceptibility of Patient Viruses

Reduced drug susceptibility was observed for a majority of the patient virus samples (Table A). 66 percent of the viruses exhibited large (define as >10X of the reference) reductions in susceptibility to one or more NRTI drugs. 52 percent of the viruses exhibited large reductions in susceptibility to one or more NNRTI drugs. 45 percent of the viruses exhibited large reductions in susceptibility to one or more PRI drugs.

Fitness of Patient Viruses

Reduced replication fitness was observed for a majority of the patient virus samples (Table A). Forty one percent of the viruses exhibited large reductions in replication fitness (<25% of the reference). Another 45% had moderate reductions (between 25–75% of the reference) in replication fitness. A minority of the patient samples (14%) displayed replication fitness that approached or exceeded "wildtype" levels (>75% of the reference). Viruses with reduced drug susceptibility, were much more likely to display reduced replication fitness (FIGS. 11,12,13, and 14).

Protease Mutations in Patient Viruses

Figure 14:
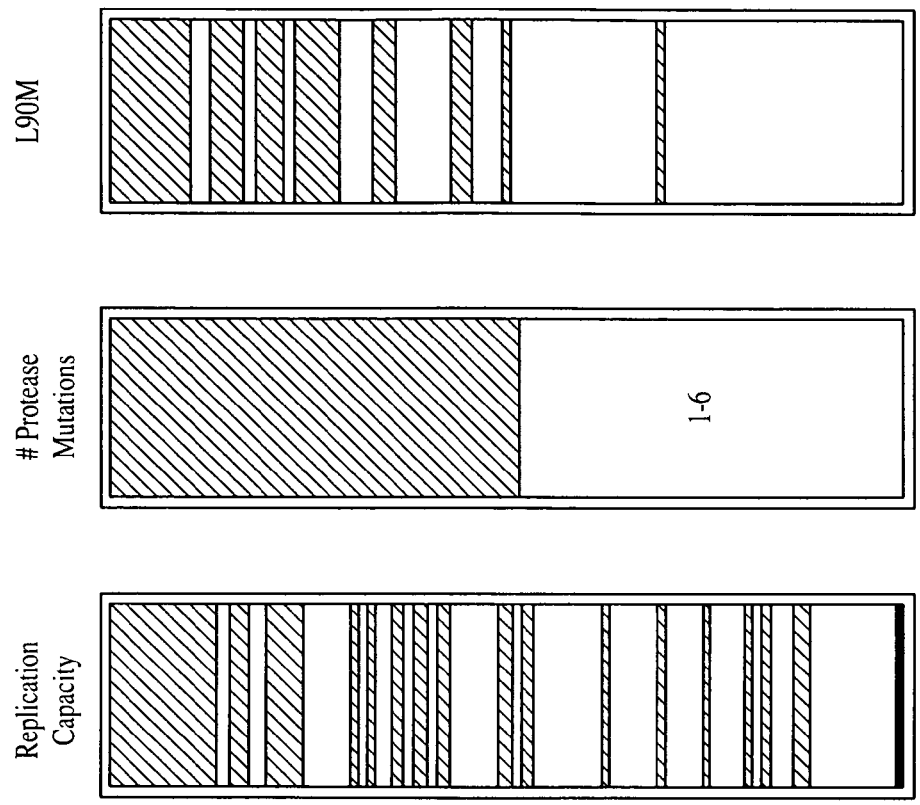
Figure 15:
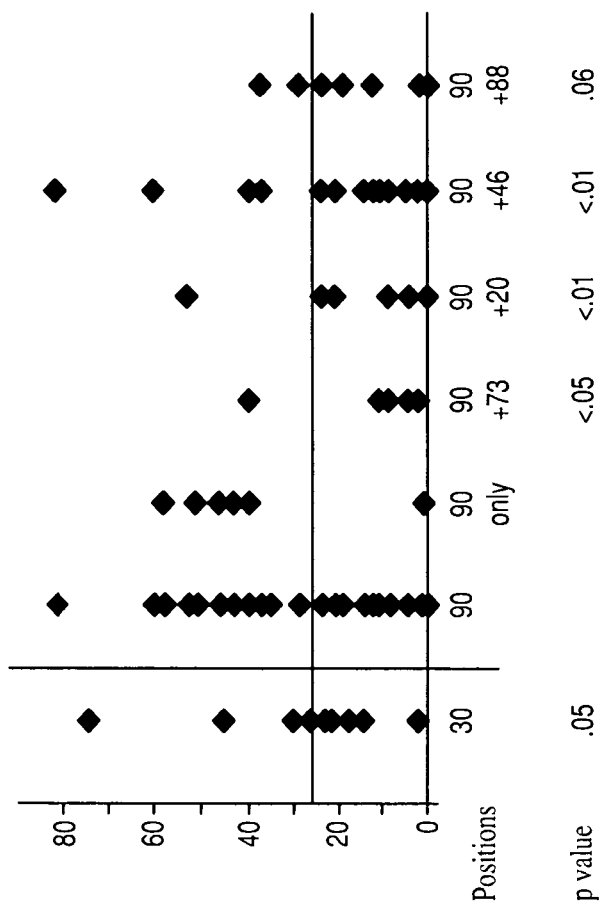

Greater than 10 mutations in protease were observed in a majority of the patient virus samples (Table A). Viruses with reduced fitness were much more likely to contain 10 or more protease mutations (FIG. 14). Sixty two percent of the viruses that exhibited large reductions in replication fitness (<25% of the reference) contained 10 or more protease mutations. Twenty two percent of the viruses with moderate reductions (between 25–75% of the reference) in fitness contained 10 or more protease mutations. Only 5% of the viruses that displayed replication fitness that approached or exceeded "wildtype" levels (>75% of the reference) contained 10 or more protease mutations (Table A). Certain protease mutations either alone (D30N) or in combination (L90M plus K20T, or M46I, or 73, or N88D) were observed at high incidences in viruses with reduced fitness (FIGS. 14 and 15).

Protease Processing of Patient Viruses

Figure 11:
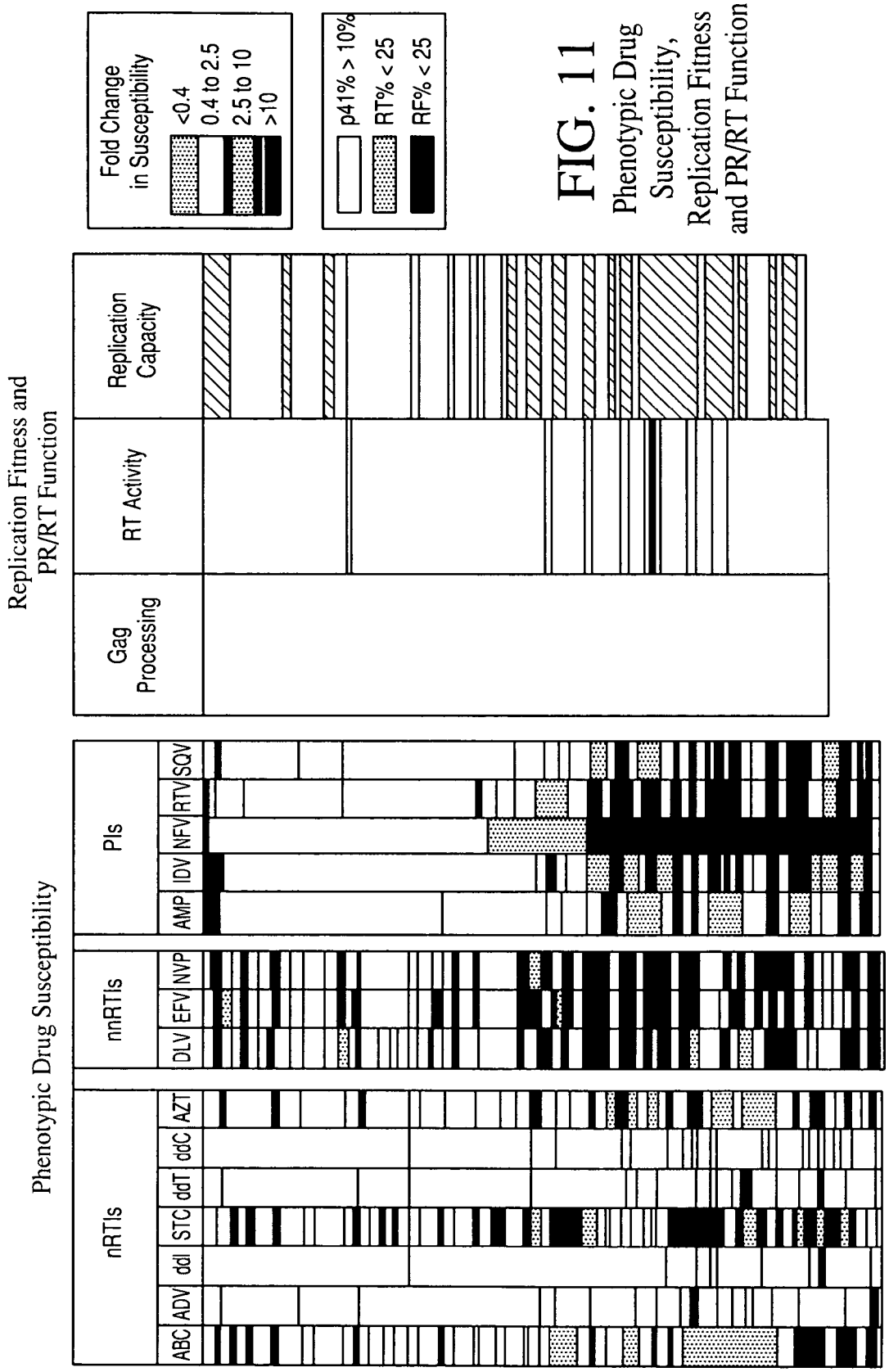
Figure 12:
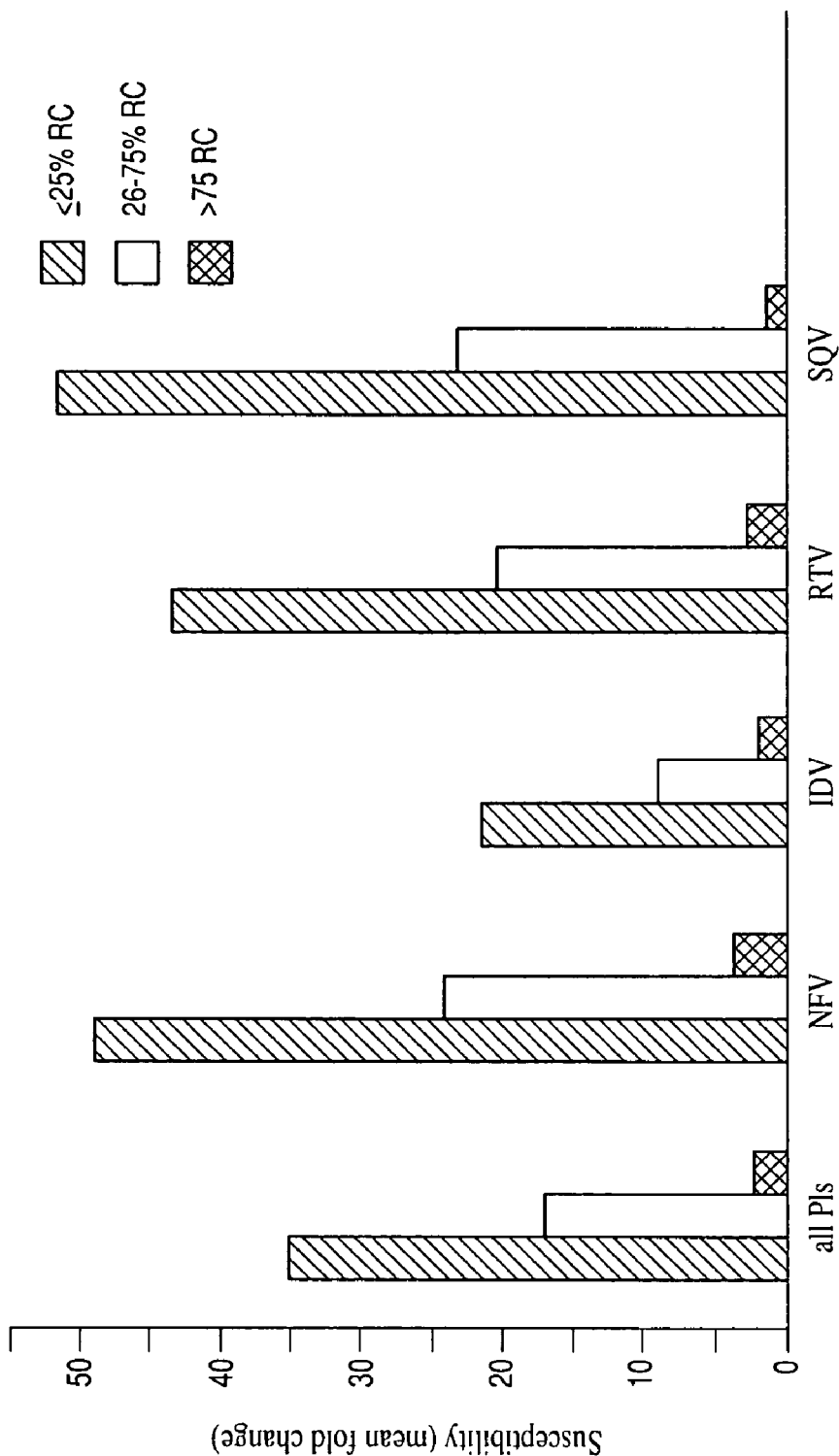
Figure 13:
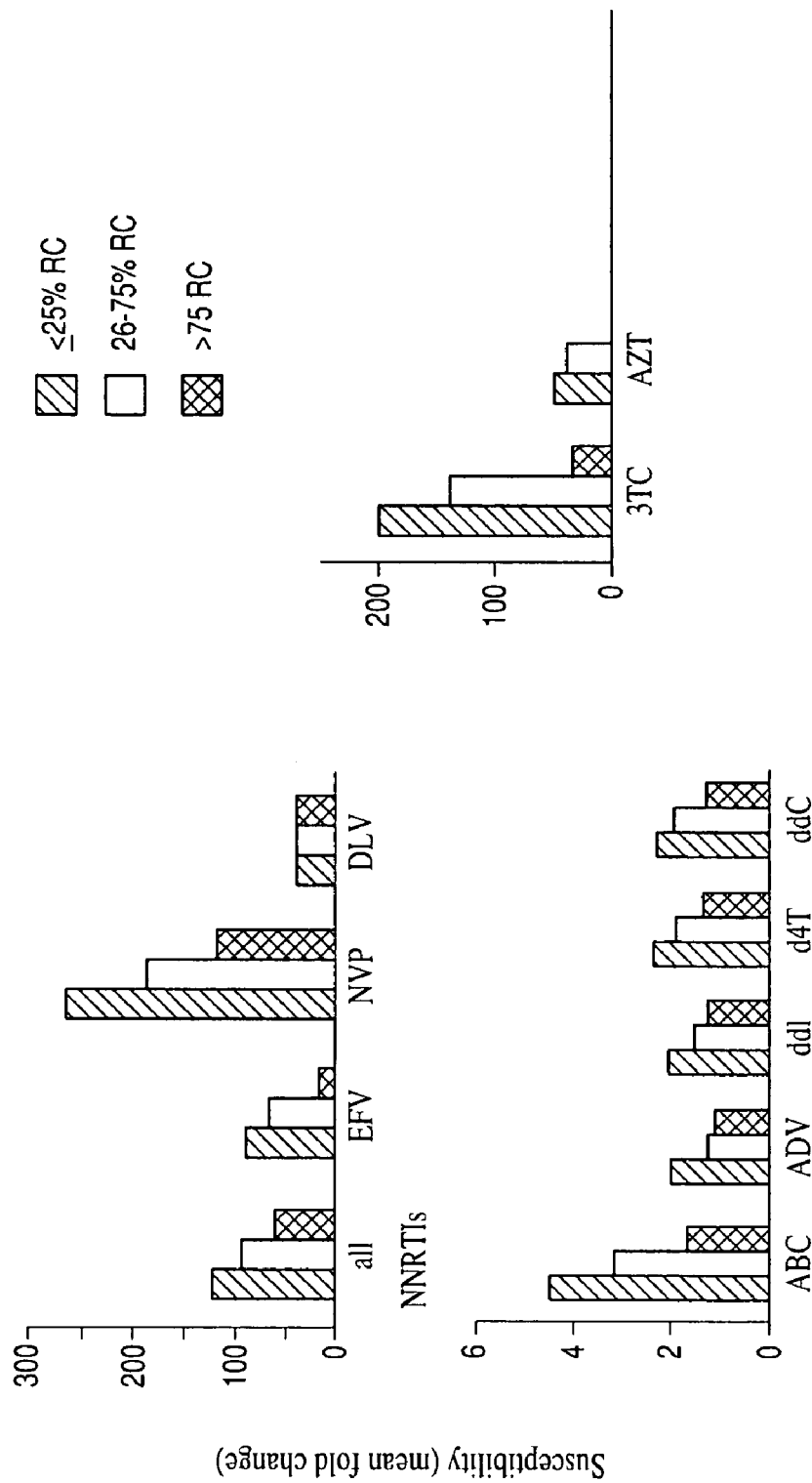
Figure 16:
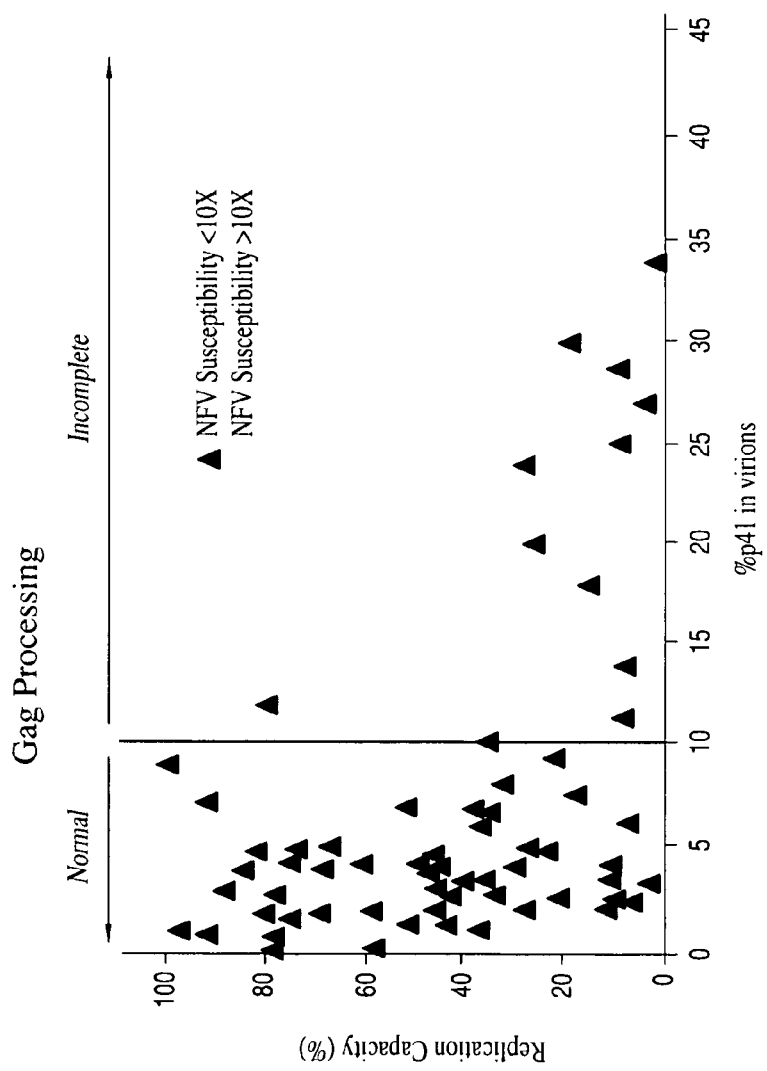

Reduced protease processing of the p55 gag polyprotein was observed in a majority of the patient virus samples (Table A). Viruses with reduced fitness were much more likely to display reduced protease processing; defined as having detectable amounts of the p41 intermediate cleavage product (FIGS. 11,14 and 16). Seventy one percent of the viruses that exhibited large reductions in replication fitness (<25% of the reference) displayed reduced protease processing. Eighteen percent of the viruses with moderate fitness reductions (between 25–75% of the reference) displayed reduced protease processing. Only 10% of the viruses that displayed replication fitness that approached or exceeded "wildtype" levels (>75% of the reference) exhibited reduced protease processing (Table A). Certain protease mutations (D30N, M46I/L, G48V, I54L/A/S/T/V, and I84V) were observed at high incidences in viruses with reduced protease processing of the p55 gag polyprotein (FIG. 17).

Reverse Transcriptase of Patient Viruses

Reduced reverse transcriptase activity processing was observed in a minority of the patient virus samples (Table A). Viruses with reduced fitness were much more likely to display reduced reverse transcriptase activity. Fourteen percent of the viruses that exhibited large reductions in replication fitness (<25% of the reference) displayed reduced reverse transcriptase activity. Only 2% of the viruses with moderate fitness reductions (between 25–75% of the reference) displayed reduced reverse transcriptase activity. None of the viruses that displayed replication fitness that approached or exceeded "wildtype" levels (>75% of the reference) exhibited reduced reverse transcriptase activity.

EXAMPLE 14

Measuring Replication Fitness to Guide Treatment Decisions

A means and method for using replication fitness measurements to guide the treatment of HIV-1 is provided. This example further provides a means and method for using replication fitness measurements to guide the treatment of patients failing antiretroviral drug treatment. This example further provides the means and methods for using replication fitness measurements to guide the treatment of patients newly infected with HIV-1.

Guiding treatment of patients with multi-drug resistant virus: Fitness/resistance test vectors were constructed as described in example 10. Fitness and drug susceptibility were measured on serial longitudinal samples collected weekly for 12 weeks from 18 patients. These patients were considered failing a protease inhibitor (typically indinavir) containing regimen and had incomplete suppression of virus replication based on routine viral load testing (>2,500 copies/mL). Phenotypic drug susceptibility testing indicated that these patient viruses were multi-drug resistant. Each patient agreed to interrupt therapy for a period of at least 12 weeks. Phenotypic drug susceptibility assays were performed as described in Example 1 on serial samples collected just prior to interrupting therapy and weekly during the period of interruption. Fitness assays were performed as described in Example 10 on serial samples collected just prior to interrupting therapy and weekly during the period of interruption. Protease processing was measured as described in Example 12.

Of the 18 patients that interrupted therapy, 16 patients had resistant viruses that regained susceptibility to antiretroviral drugs during the period of treatment interruption. The phenotypic test results of a representative patient are shown in FIG. 18. Typically, susceptibility returned to all drug classes simultaneously, consistent with the re-emergence of a minor population of drug sensitive virus. In the representative example shown in Figure M, drug sensitivity was abruptly restored between weeks 9 and 10. Genotypic analysis (DNA sequence of protease and reverse transcriptase) are also consistent with the re-emergence of a drug sensitive virus. These data show the loss of most or all drug resistance mutation simultaneously (data not shown). The data are not consistent with random back mutations. Back mutations would predict that restored susceptibility to drugs would occur unevenly for different drug classes and/or within a drugs within the same class.

Figure 19:
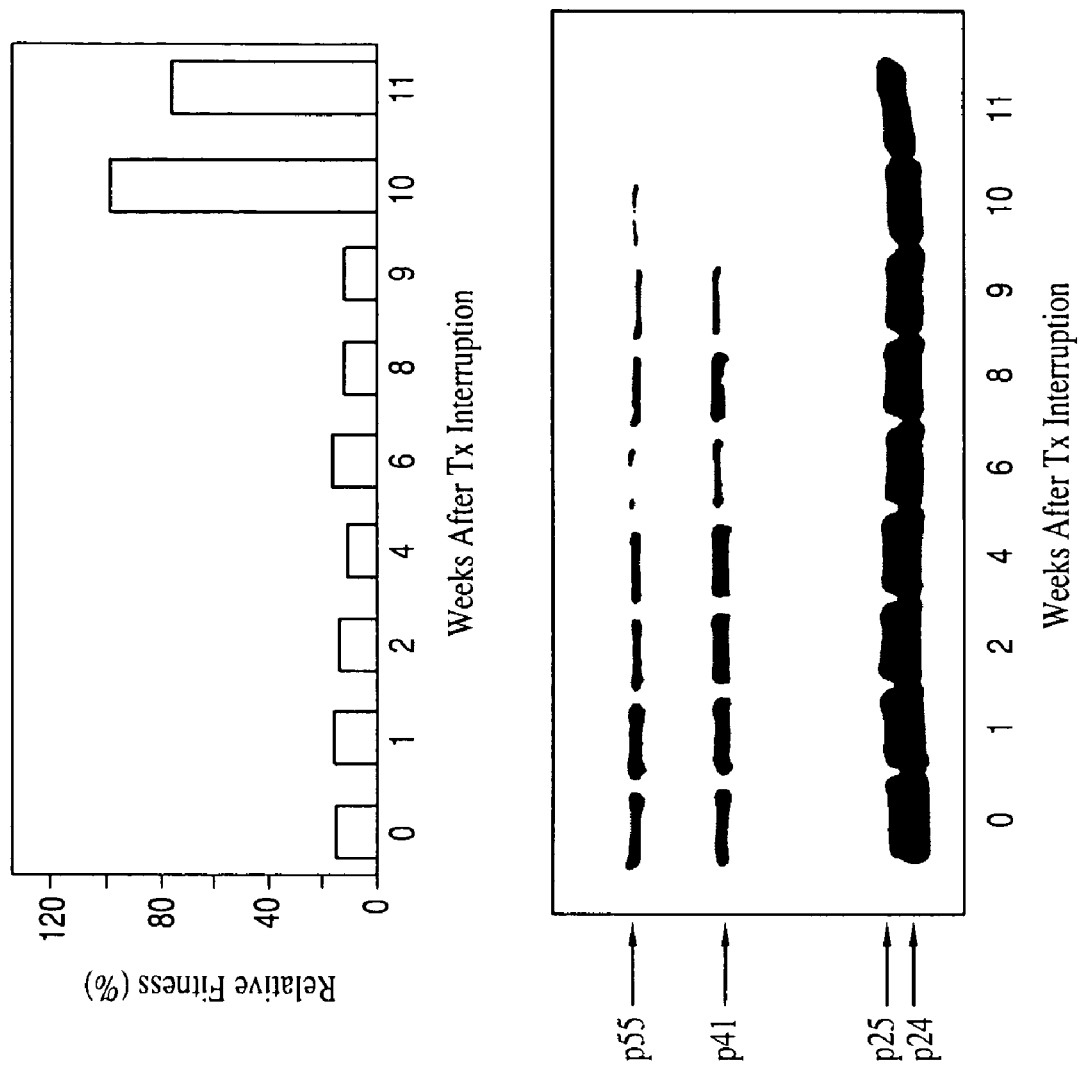
Figure 20:
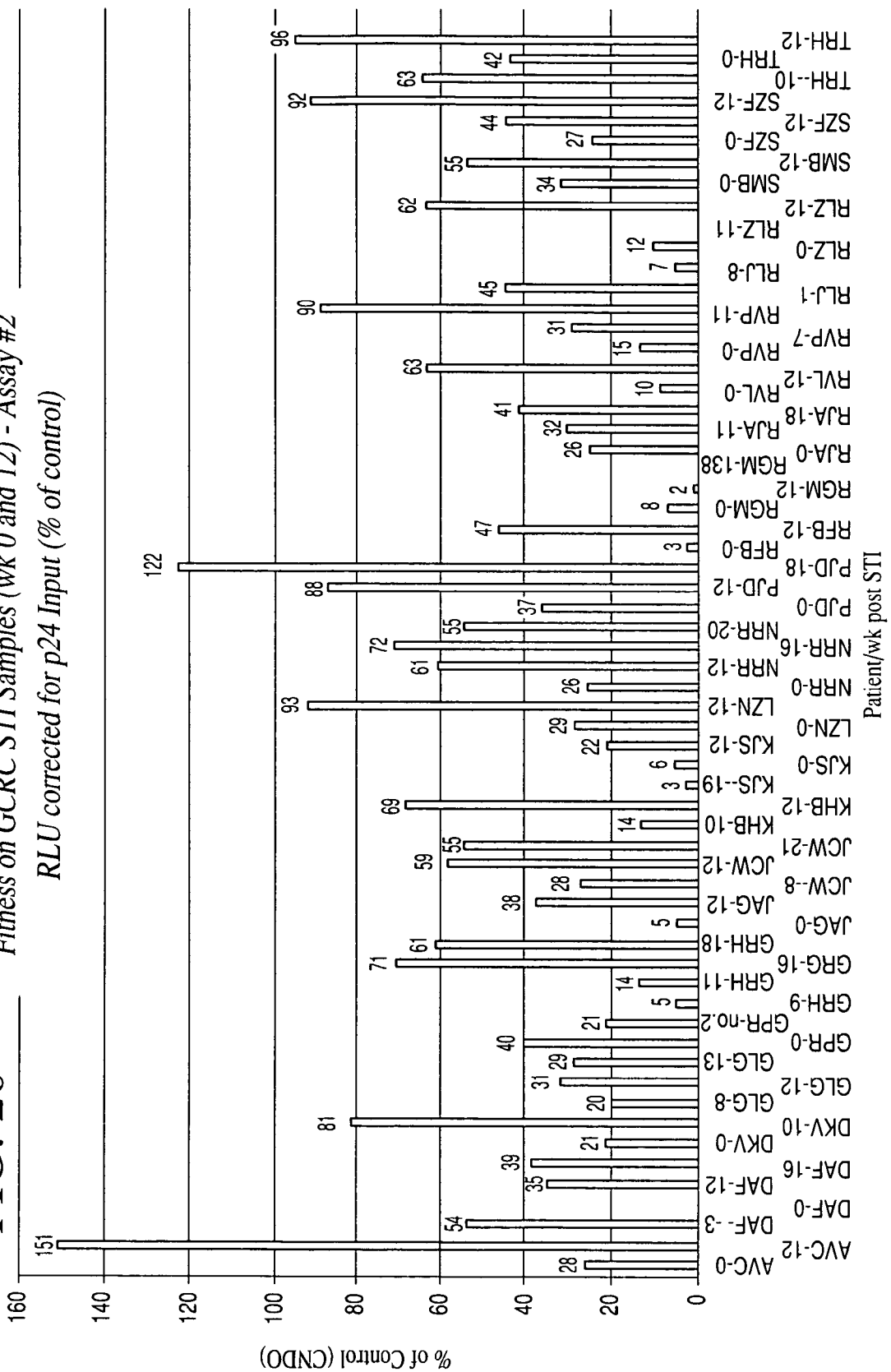

Generally, the re-emergence of the drug susceptible virus was also accompanied by a simultaneous increase in replication fitness. This relationship is clearly evident for the representative virus (FIG. 19). Several other examples with less frequent timepoints are shown in FIG. O. Virus from patients that did not revert to drug susceptibility after interruption generally did not exhibit an increase in replication fitness, nor did viruses from patients that did not interrupt treatment (FIG. 20). The data indicate that the drug sensitive virus that re-emerged after treatment interruption is able to replicate better than the drug resistant virus that was present before treatment was interrupted. The re-emergence of drug susceptible virus in this group of patients was also accompanied by an increase in viral load and a decrease in DC4 T-cells, indicators of disease progression. Thus, fitness information can be used to guide treatment of patients that harbor multi-drug resistant virus and are considering treatment interruption. If the patient virus is drug resistant but has low replication capacity, the patient and the physician should consider continuing drug treatment to prevent the re-emergence of a drug sensitive virus with higher replication capacity and greater pathogenecity. Alternatively, if the patient virus is drug resistant and has high replication capacity, the patient and the physician may consider interrupting treatment to spare the patient from the harmful and unpleasant side effects of antiretroviral drugs that are not providing clinical benefit.

Furthermore, physicians may choose to perform routine replication fitness assays for patients that have multi-drug resistant virus. This assay could be used to monitor the replication fitness of patient viruses when complete suppression of virus replication is not possible due to multi-drug resistance. The assay would be used to guide treatment decisions that prevent the drug resistant virus with low replication fitness from increasing its replication fitness. In this way, physicians may prolong the usefulness of antiretroviral drugs despite the presence of drug resistant virus in the patient.

Guiding Treatment of Newly Infected Patients:

Patients that maintain high virus loads (setpoint) after acute infection are more likely to exhibit accelerated disease progression. Therefore, it is advantageous for this class of patient to initiate antiretroviral drug treatment as soon as possible after diagnosis with HIV-1 infection. In conjunction with viral load, fitness measurements of viruses in newly infected patients may provide a useful measurement to identify those individuals that will develop elevated setpoints after primary infection and consequently are likely to exhibit accelerated disease progression. Fitness measurements may guide the decision to treat immediately after diagnosis or a some later time point.

EXAMPLE 15

Measuring Saquinavir Susceptibility of Viruses Containing Various Amino Acid Substitutions in Protease at Position 82

This example provides a means and method for identifying mutations in protease that affect susceptibility (increased or decreased) to saquinavir.

In one embodiment of this invention, the effects of combination of mutations at position 82 (for example, V82A, V82F, V82S, or V82T are evaluated using the following method comprising: (i) collecting a biological sample from an HIV-1 infected subject; (ii) evaluating whether the HIV-1 in the sample contains nucleic acid encoding protease having a valine to alanine (V82A), phenylalanine (V82F), serine (V82S), or threonine (V82T) substitution at position 82 or a leucine to methionine substitution at position 90 (L90M); and (iii) determining susceptibility to protease inhibitors (PRIs).

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 82 of the HIV-1 protease is mutated to alanine, phenylalanine, or threonine, can be performed using various methods, such as direct characterization of the viral nucleic acid encoding protease or direct characterization of the protease protein itself. Defining the amino acid at position 82 of protease can be performed by direct characterization of the protease protein by conventional or novel amino acid sequencing methodologies, epitope recognition by antibodies or other specific binding proteins or compounds. Alternatively, the amino acid at position 82 of the HIV-1 protease protein can be defined by characterizing amplified copies of HIV-1 nucleic acid encoding the protease protein. Amplification of the HIV-1 nucleic acid can be performed using a variety of methodologies including reverse transcription-polymerase chain reaction (RT-PCR), NASBA, SDA, RCR, or 3SR. The nucleic acid sequence encoding HIV protease at codon 82 can be determined by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid position 82 can be evaluated using a variety of probe hybridization methodologies, such as genechip hybridization sequencing (Affymetrix), line probe assay (LIPA; Murex), and differential hybridization (Chiron).

In a preferred embodiment of this invention, evaluation of the effects of mutations at amino acid position 82 of HIV-1 protease on protease inhibitor susceptibility, was carried out using a phenotypic susceptibility assay using resistance test vector DNA prepared from the biological sample. In one embodiment, plasma samples were collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, into an indicator gene viral vector thereby generating a resistance test vector. Resistance test vector DNA was isolated from the bacterial culture and the phenotypic susceptibility assay was carried out as described in Example 1. The genotype of the protease region was determined by dideoxy chain-termination sequencing of the resistance test vector DNA. Samples were categorized as having mutations in protease encoding alanine (A), phenylalanine (F), or threonine (T) at position 82, instead of the wild-type valine (V), and the percentage of samples in each category displaying hyper-sensitivity to saquinavir (i.e., fold-change vs. reference of 0.4 or less) was determined. Surprisingly, the percentage of saquinavir hyper-susceptible viruses was much higher amongst viruses containing V82F than those containing V82A or V82T. This observation implies that the detection of V82F in protease predicts a positive virological response to saquinavir treatment.

EXAMPLE 16

Measuring Replication Fitness of Viruses with Mutations in Integrase

This example provides a means and method for identifying mutations in integrase that alter replication fitness.

This example provides the means and methods for identifying mutations that alter replication fitness for various components of HIV-1 replication, including, but not limited to integration, virus assembly, and virus attachment and entry. This example also provides a means and method for quantifying the affect that specific mutations in protease, reverse transcriptase, or integrase have on replication fitness.

This method can be used for quantifying the effect that specific integrase mutations have on replication fitness and can be used to quantify the effect of other mutations in other viral genes involved in HIV-1 replication, including, but not limited to the gag, pol, and envelope genes.

Fitness test vectors engineered by site directed mutagenesis to contain specific mutations in integrase were tested in a fitness assay to determine accurately and quantitatively the relative fitness compared to a well-characterized reference standard.

Genotypic changes that are observed to correlate with resistance to integrase inhibitors are evaluated by construction of fitness vectors containing the specific mutation on a defined, wild-type (drug susceptible) genetic background. Mutations may be incorporated alone and/or in combination with other mutations that are thought to modulate the fitness of a virus. Mutations are introduced into the fitness test vector through any of the widely known methods for site-directed mutagenesis. In one embodiment of this invention the mega-primer PCR method for site-directed mutagenesis is used (Sarkar, G. and Sommar, S. S., 1994, Biotechniques 8, 404–407). A fitness test vector containing the specific mutation or group of mutations are then tested using the fitness assay described in Example 10 and the fitness is compared to that of a genetically defined wild-type (drug susceptible) fitness test vector which lacks the specific mutations. Observed changes in fitness are attributed to the specific mutations introduced into the fitness test vector. In several related embodiments of the invention, fitness test vectors containing site directed mutations in integrase that result in amino acid substitutions at positions 66, 154, 66 and 153, and 66 and 154 are constructed and tested for fitness. As controls, mutants with multiple changes conferring resistance to reverse transcriptase and protease inhibitors (MDRC4) and with a mutation in the integrase active site (D64V) were also tested. The fitness results enable the correlation between specific integrase amino acid substitutions and changes in viral fitness.

FIG. 6. Distribution of saquinavir hyper-susceptibility by amino acid change at position 82.

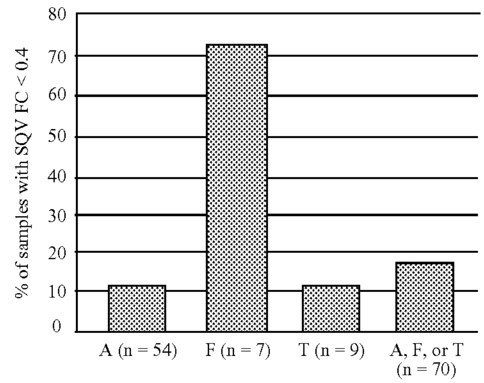

FIG. 7. Relative luciferase activity of integrase inhibitor-resistant site-directed mutants.

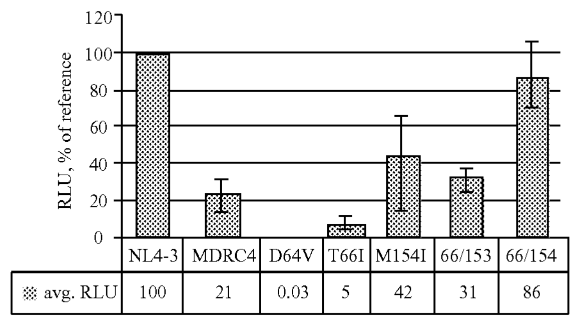

Table 1: PRI susceptibility of selected patent samples. Viruses displaying increased susceptibility to amprenavir (5-fold or greater) were genotyped and found to contain the N88S mutation in PR. Samples were listed in order of decreasing susceptibility.

TABLE 1

| Sample | Prior PRI | Fold Change vs. Reference | | | | | PR Mutations |
|---|---|---|---|---|---|---|---|
| ID | Experience | SQV | IDV | RTV | NFV | AMP | PR Mutations |
| 0732 | NFV | 0.73 | 2.11 | 1.72 | 8.92 | 0.08 | K14R, I15V, K20T, E35D, M361, R41K, I62V, L63Q, N88S |
| 627 | IDV | 0.26 | 6.16 | 1.50 | 21.06 | 0.09 | I13I/V, E35D, M46L, L63P, I64V, I73V, N88S |
| 1208 | NFV | 1.55 | 3.15 | 1.22 | 11.06 | 0.10 | I62V, L63P, V77I, N88S |
| 360 | IDV | 1.88 | 6.31 | 1.49 | 29.95 | 0.15 | I13V, K20M, M36V, N37A, M46I, I62V, L63P, N88S, I93L |
| 0910 | NFV | 1.41 | 5.17 | 1.85 | 16.76 | 0.16 | M46I, L63P, V77I, N88S, I93I/L |
| 3542 | IDV | 1.28 | 7.61 | 3.36 | 24.67 | 0.16 | I13V, K14R, N37D, M46, L63P, N88S, I93L |
| 3654 | | 1.80 | 7.56 | 1.95 | 18.61 | 0.20 | I13V, R41K, M46I, L63P, V77I, N88S, I93L |

Fold Change Limits: >2.5 < 0.4

TABLE 2

PRI susceptibility of site-directed mutants in PR. Mutations were introduced into the drug sensitive reference resistance test vector and the susceptibility to PRIs were determined.
Fold Change vs. reference

| Site-Directed Mutations | SQV | IDV | RTV | NFV | AMP |
|---|---|---|---|---|---|
| L63P | 1.04 | 1.12 | 1.27 | 1.43 | 1.06 |
| L63P, V77I | 1.24 | 1.72 | 1.73 | 2.49 | 0.91 |
| N88S | 0.47 | 1.56 | 0.36 | 2.39 | 0.04 |
| L63P, N88S | 1.44 | 2.56 | 0.77 | 5.20 | 0.11 |
| L63P, V77I, N88S | 1.24 | 3.09 | 1.39 | 12.89 | 0.08 |
| M46L, L63P, N88S | 1.15 | 2.30 | 0.85 | 6.18 | 0.12 |
| M46L, L63P, V77I, N88S | 1.45 | 2.97 | 1.33 | 12.24 | 0.14 |

Table 3: Relative luciferase activity levels for patient sample virus-derived resistance test vector pools. The luciferase activity (relative light units, RLU) measured in the absence of drug for the patient sample was compared to that of the drug sensitive reference control from the same assay run, and expressed as a percentage of control. These values are from one assay each. All the samples that contain the N88S mutations in PR were found to have reduced luciferase activity compared to control.

TABLE 3

| Sample ID | PR Mutations | Relative Luciferase Activity (% of control) |
|---|---|---|
| 0732 | K14R, I15V, K20T, E35D, M36I, R41K, I62V, L63Q, N88S | 8.5 |
| 627 | I131/V, E35D, M46L, L63P, I64V, I73V, N88S | 0.7 |
| 1208 | I62V, L63P, V77I, N88S | 14.2 |
| 360 | I13V, K20M, M36V, N37A, M46I, I62V, L63P, N88S, I93L | 2.2 |

TABLE 3-continued

| Sample ID | PR Mutations | Relative Luciferase Activity (% of control) |
|---|---|---|
| 0910 | M46I, L63P, V77I, N88S, I93I/L | 16.0 |
| 3542 | I13V, K14R, N37D, M46I, L63P, N88S, I93L | 4.6 |
| 3654 | I13V, R41K, M46I, L63P, V77I, N88S, I93L | 12.8 |

Table 4: Relative luciferase activity levels for resistance test vectors containing site-directed mutations. The luciferase activity (relative light units, RLU) measured in the absence of drug for the mutant was compared to that of the drug sensitive reference control from the same assay run, and expressed as a percentage of control. These values are from one to five assays each, and each value was obtained using an independent clone for mutants which were tested multiple times. All the constructs that contain the N88S mutations in PR were found to have reduced luciferase activity compared to control. All the constructs with the K20T mutation were essentially inactive in the assay.

TABLE 4

| Site-Directed Mutations | Average Luciferase Activity (% of control) | number of clones tested |
|---|---|---|
| L63P | 163.9 | 1 |
| L63P, V77I | 75.6 | 1 |
| N88S | 1.0 | 3 |
| L63P, N88S | 20.7 | 2 |
| L63P, V77I, N88S | 29.3 | 2 |
| M46L, L63P, N88S | 28.0 | 2 |
| M46L, L63P, V77I, N88S | 53.2 | 5 |
| K20T, N88S | <0.01 | 5 |
| K20T, L63P, N88S | <0.01 | 1 |

Table 5: Oligonucleotide primers used for PCR amplification and for generating site-directed mutants.

TABLE 5

| Primer name: | | | | |
|---|---|---|---|---|
| #1: PCR6 | 5' | CCAATTRYTGTGATATTTCTCATGNTCHTCTTGGG | 3' | (35-mer) |
| #2: PDS/Apa | 5' | CATGTTGCAGGGCCCCTAGGAAAAAGGGCTGTTGGAAATGTG | 3' | (42-mer) |
| #3: PDS/Age | 5' | CACTCCATGTACCGGTTCTTTTAGAATYTCYCTG | 3' | (34-mer) |
| #4: RsrII | 5' | ACTTTCGGACCGTCCATTCCTGGCTTTAATTTTACTGGTACAG | 3' | (43-mer) |
| #5: K20T | 5' | GGGGGGCAATTAACGGAACGTCTATTAG | 3' | (28-mer) |
| #6: M46L | 5' | GATGGAAACCAAAATTGATAGGGGAATTG | 3' | (30-mer) |
| #7: L63P | 5' | GTATGATCAGATACCCATAGAAATCTGC | 3' | (28-mer) |
| #8: N88S | 5' | CTGAGTCAACAGACTTCTTCCAATTATG | 3' | (28-mer) |

R = A or G
Y = C or T
N = A, C, G, or T
H = A, C, or T

TABLE 6

PRI Susceptibility (Fold Change <2.5) of Viruses with Mutations at 82 and/or 90

Percent of viruses with indicated primary mutation(s) which are drug sensitive (fold change in IC50 < 2.5)

| drug | V82A/F/S/T | L90M | V82A/F/S/T and L90M |
|---|---|---|---|
| RTV | 8.0 | 27.6 | 3.0 |
| NFV | 20.0 | 8.6 | 3.0 |
| IDV | 22.7 | 31.0 | 9.1 |
| AMP | 53.3 | 65.5 | 33.3 |
| SQV | 73.3 | 46.6 | 21.2 |

TABLE 7

Correlation Between 82A/F/S/T, Secondary Mutations, and IDV Susceptibility.

| position | n | % FC > 2.5 | chi square p |
|---|---|---|---|
| 24 | 20 | 100% | <0.005 |
| 71 | 27 | 100% | <0.0001 |
| 54 | 38 | 95% | <0.0001 |
| 46 | 35 | 89% | <0.01 |
| 10 | 47 | 83% | <0.05 |
| 63 | 72 | 79% | <0.05 |
| 82 | 75 | 77% | | all virus with V82A/F/S/T and no other primary mutations.

TABLE 8

Correlation Between 82A/F/S/T, Secondary Mutations, and SQV Susceptibility

| position | n | % FC > 2.5 | chi square p |
|---|---|---|---|
| 20 | 5 | 80% | <0.001 |
| 36 | 11 | 73% | <0.001 |
| 24 | 20 | 65% | <0.0001 |
| 71 | 27 | 52% | <0.0001 |
| 54 | 38 | 47% | <0.0001 |
| 10 | 47 | 40% | <0.001 |
| 82 | 75 | 27% | | all virus

TABLE 9

Association Between SQV and IDV Susceptibility, V82A/F/S/T, and Number of Resistance Associated Mutations

| Number of secondary mutations | Number of samples | % with IDV FC > 2.5 | % with SQV FC > 2.5 |
|---|---|---|---|
| 1 | 75 | 77 | 27 |
| 2 | 67 | 82 | 30 |
| 3 | 51 | 88 | 39 |
| 4 | 38 | 95 | 50 |
| 5 | 25 | 96 | 60 |
| 6 | 17 | 100 | 76 |
| 7 | 5 | 100 | 60 |

TABLE 10

Correlation Between L90M, Secondary Mutations, and IDV Susceptibility.

| position | n | % FC > 2.5 | chi square p |
|---|---|---|---|
| 73 | 19 | 89% | <0.01 |
| 71 | 18 | 89% | <0.001 |
| 46 | 25 | 88% | <0.05 |
| 90 | 58 | 69% | | all viruses with L90M and

TABLE 11

Correlation Between L90M, Secondary Mutations, and SQV Susceptibility.

| position | n | % FC > 2.5 | chi square p |
|---|---|---|---|
| 73 | 19 | 79% | <0.01 |
| 71 | 18 | 78% | <0.001 |
| 77 | 25 | 76% | <0.05 |
| 10 | 34 | 65% | <0.05 |
| 90 | 58 | 55% | | all viruses

TABLE 12

Association Between SQV and IDV Susceptibility, L90M, and Number of Resistance Associated Mutations.

| Number of secondary mutations | Number of samples | % w with IDV FC > 2.5 | % w with SQV FC > 2.5 |
|---|---|---|---|
| 0 | 58 | 69 | 53 |
| 1 | 57 | 70 | 47 |
| 2 | 56 | 70 | 48 |
| 3 | 41 | 80 | 68 |
| 4 | 31 | 87 | 77 |
| 5 | 14 | 100 | 100 |
| 6 | 6 | 100 | 100 |

What is claimed is:

1. A method for assessing the effectiveness of a candidate HIV antiretroviral compound, said method comprising:
   a) culturing a host cell in the presence of said candidate HIV antiretroviral compound, wherein said host cell comprises a test vector comprising (i) a nucleic acid segment encoding HIV protease having a mutation at codon 88 and (ii) an indicator gene, wherein expression of said indicator gene depends upon the activity of said HIV protease;
   b) measuring the amount of expression of said indicator gene in said host cell from step (a); and
   c) comparing the amount of expression of said indicator gene as measured in step (b) with an amount of expression of said indicator gene measured in said host cell of step (a) cultured in the absence of said candidate HIV antiretroviral compound, wherein the difference between the amount of expression of said indicator gene measured in step (c) relative to that measured in step (b) correlates with the effectiveness of said candidate HIV antiretroviral compound, thereby assessing the effectiveness of said candidate HIV antiretroviral compound.

2. The method of claim 1, wherein said a nucleic acid segment encoding HIV protease further comprises a mutation at codon(s) 63 and/or 77.

3. The method of claim 1, wherein said a nucleic acid segment encoding HIV protease further comprises a mutation at codon(s) 63, 77 and/or 46, or a combination thereof.

4. The method of claim 1, wherein said a nucleic acid segment encoding HIV protease further comprises a mutation at codon(s) 63, 77, 46, 10, 20 and/or 36, or a combination thereof.

5. A test vector comprising a nucleic acid segment encoding HIV protease having a mutation at codon 88, and an indicator gene, wherein expression of the indicator gene depends upon the activity of said HIV protease.

6. The test vector of claim 5, wherein said nucleic acid segment encoding HIV protease further comprises a mutation at codon(s) 63 and/or 77.

7. The test vector of claim 5, wherein said nucleic acid segment encoding HIV protease further comprises a mutation at codon(s) 63, 77 and/or 46, or a combination thereof.

8. The test vector of claim 5, wherein said nucleic acid segment encoding HIV protease further comprises a mutation at codon(s) 63, 77, 46, 10, 20 and/or 36, or a combination thereof.

* * * * *